US005846715A

United States Patent [19]

Purcell et al.

[11] Patent Number: 5,846,715

[45] Date of Patent: Dec. 8, 1998

[54] CD46 VARIANTS

[75] Inventors: Damian Francis John Purcell, South Gisborne; Sarah May Russell, North Fitzroy; Ian Farquar Campbell McKenzie, Brunswick West, all of Australia

[73] Assignee: The Austin Research Institute, Heidelberg, Australia

[21] Appl. No.: 528,057

[22] Filed: Sep. 14, 1995

Related U.S. Application Data

[63] Continuation-in-part of Ser. No. 961,686, Jan. 11, 1993, abandoned.

[30] Foreign Application Priority Data

May 11, 1990 [AU] Australia ................................ PK0133

[51] Int. Cl.[6] .............................. C12Q 1/68; C07H 21/04

[52] U.S. Cl. .......................... 435/6; 536/23.5; 536/24.31; 536/24.33

[58] Field of Search ................................ 435/6; 536/23.5, 536/24.31, 24.33

[56] References Cited

U.S. PATENT DOCUMENTS

| | | | |
|---|---|---|---|
| 5,514,787 | 5/1996 | Atkinson | 536/23.1 |
| 5,552,381 | 9/1996 | Atkinson | 514/8 |

FOREIGN PATENT DOCUMENTS

| | | |
|---|---|---|
| 91/02002 | 2/1991 | WIPO . |
| 91/05855 | 5/1991 | WIPO . |

OTHER PUBLICATIONS

Lublin, D. et al, "Molecular Cloning & Chromosomal Localization of Human Membrane Cofactor Protein (MCP)", *The Journal of Experimental Medicine*, vol. 168: pp. 181–194, (Jul. 1988).

Ballard, L. et al, "Biochemical Characterization of Membrane Cofactor Protein of the Complement System", *The Journal of Immunology*, vol. 141: No. 11, pp. 3923–3929 (Dec. 1, 1988).

Purcell et al, "The Human Non–lineage Antigen CD64 (HULY–M5) and Primate Retroviral gp70 Molecules Share Protein Defined Antigenic Determinants", *Immunology and Cell Biology*, vol. 67: No. 5, pp. 279–289 (1989).

Purcell et al, "Human Non–lineage Antigen, CD46, (HULY–M5): Purification and Partial Sequencing Demonstrates Structural Homology with Complement–regulating Glycoproteins", *Immunogenetics*, vol. 31: pp. 21–28 (1990).

Ballard et al, "A Polymorphism of the Complement Regulatory Protein MCP (Membrane Cofactor Protein or gp 45–70)", *Chemical Abstracts*, vol. 107: No. 9, pp. 3850–3855, (Aug. 31, 1987).

Bora, N.S. et al, "Structural Gene for Human Membrane Cofactor Protein (MCP) of Complement Maps to Within 100 Kb of the 3' End of the C3b/C4b Receptor Gene", *Chemical Abstracts*, vol. 110: pp. 597–602, (Apr. 24, 1989).

Seya, et al., Functional Properties of Membrane Cofactor Protein of Complement, *Biochem. J.*, vol. 264: pp. 581–588, (1989).

Ballard, L. et al, "A Polymorphism of the Complement Regulatory Protein MCP," *The Journal of Immunology*, vol. 138: No. 11, pp. 3850–3855 (Jun. 1, 1987).

Seya, et al., "Distribution of Membrane Cofactor Protein of Complement on Human Peripheral Blood Cells. An Altered Form is Found on Granulocytes," *Eur. J. Immunology*, vol. 18: pp. 1289–1294 (1988).

*Primary Examiner*—Kenneth R. Horlick
*Attorney, Agent, or Firm*—Foley & Lardner

[57] ABSTRACT

CD46 (membrane cofactor protein) is a family of human cell surface glycoprotein with cofactor activity for factor I mediated cleavage of complement components C3*b* and C4*b*. Disclosed are novel nucleic acid sequences arising from splice variants or derivatives thereof of the structural gene encoding the family of proteins. From these sequences recombinant derived proteins and antibodies thereto can be produced. The proteins can resemble native CD46 isoforms or comprise new permutations of exons within the structural gene. The nucleic acids, proteins and antibodies have utility as probes, diagnostic reagents and therapeutic agents.

13 Claims, 40 Drawing Sheets

FIG. 1a

TTTCCTGGGTTGCTTCTGGCGGCCATGGTGTTGCTGCTGTAC
F P G L L L A A M V L L L Y

ATTGGTGAACGAGTAGATTATAAGTGTAAAAAAGGATACTTC
I G E R V D Y K C K K G Y F

AGAGAAACATGTCCATATATACGGGATCCTTTAAATGGCCAA
R E T C P Y I R D P L N G Q

GAAGAAATTCTATATTGTGAACTTAAAGGATCAGTAGCAATT
E E I L Y C E L K G S V A I

AGTGAAGTAGAAGTATTTGAGTATCTTGATGCAGTAACTTAT
S E V E V F E Y L D A V T Y

TGGAGTCGTGCTGCTCCAGAGTGTAAAGTGGTCAAATGTCGA
W S R A A P E C K V V K C R

TGCGATAAGGGTTTTTACCTCGATGGCAGCGACACAATTGTC
C D K G F Y L D G S D T I V pm5.3

GCGTCCAGTGCCTCAGGTCCTAGGCCTACTTACAAGCCTCCA
A S S A S G P R P T Y K P P pm5.6

GTTATTGCCATAGTTGTTGGAGTTGCAGTAATTTGTGTTGTC
V I A I V V G V A V I C V V pm5.3, pm5.6, & pm5.10

TCTCTCTGAGAAGGAGAGATGAGAGAAAGGTTTGATTTTATC
S L ***

TGAATAGATTCCACAACCTGGTTTGCCAGTTCATCTTTTGAC
GTGGCTTGAATGTAGGTAGCATCCTTTGATGCTTCTTTGAAA
CATGCCTGGTTGTATTAAAGCAGGATATGCTGTATTTTATA
TGTTCAAAGATTAATGCCCCG

FIG. 1b

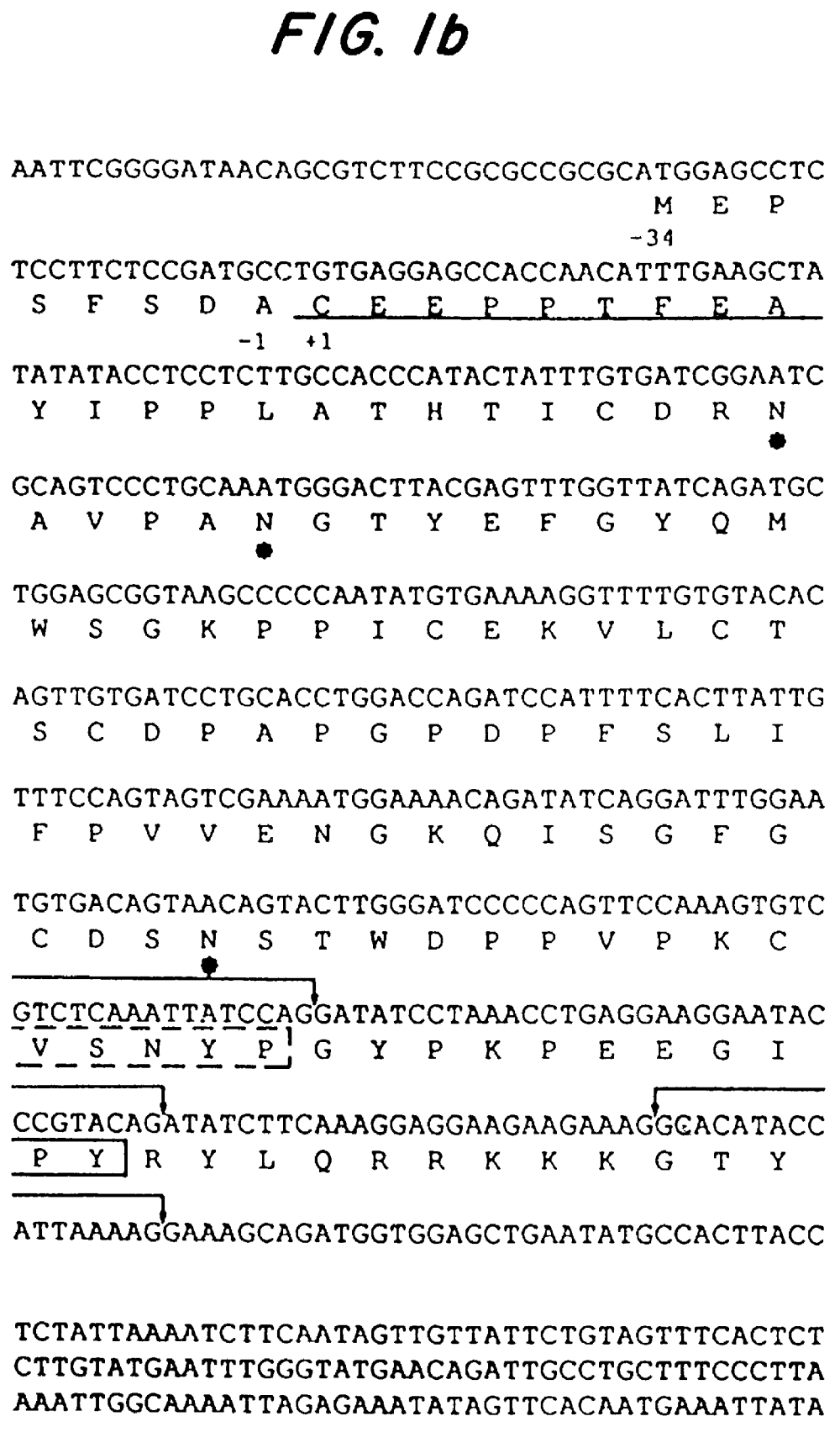

```
AATTCGGGGATAACAGCGTCTTCCGCGCCGCGCATGGAGCCTC
                                  M  E  P
                                -34
TCCTTCTCCGATGCCTGTGAGGAGCCACCAACATTTGAAGCTA
 S  F  S  D  A  C  E  E  P  P  T  F  E  A
            -1  +1
TATATACCTCCTCTTGCCACCCATACTATTTGTGATCGGAATC
 Y  I  P  P  L  A  T  H  T  I  C  D  R  N

GCAGTCCCTGCAAATGGGACTTACGAGTTTGGTTATCAGATGC
 A  V  P  A  N  G  T  Y  E  F  G  Y  Q  M

TGGAGCGGTAAGCCCCCAATATGTGAAAAGGTTTTGTGTACAC
 W  S  G  K  P  P  I  C  E  K  V  L  C  T

AGTTGTGATCCTGCACCTGGACCAGATCCATTTTCACTTATTG
 S  C  D  P  A  P  G  P  D  P  F  S  L  I

TTTCCAGTAGTCGAAAATGGAAAACAGATATCAGGATTTGGAA
 F  P  V  V  E  N  G  K  Q  I  S  G  F  G

TGTGACAGTAACAGTACTTGGGATCCCCCAGTTCCAAAGTGTC
 C  D  S  N  S  T  W  D  P  P  V  P  K  C

GTCTCAAATTATCCAGGATATCCTAAACCTGAGGAAGGAATAC
 V  S  N  Y  P  G  Y  P  K  P  E  E  G  I

CCGTACAGATATCTTCAAAGGAGGAAGAAGAAAGGCACATACC
 P  Y  R  Y  L  Q  R  R  K  K  K  G  T  Y

ATTAAAAGGAAAGCAGATGGTGGAGCTGAATATGCCACTTACC

TCTATTAAAATCTTCAATAGTTGTTATTCTGTAGTTTCACTCT
CTTGTATGAATTTGGGTATGAACAGATTGCCTGCTTTCCCTTA
AAATTGGCAAAATTAGAGAAATATAGTTCACAATGAAATTATA
```

FIG. 1c

```
CCGGCCGCCGCGAGTGTCCCTTTCCTTCCTGGCGC   78
P  G  R  R  E  C  P  F  P  S  W  R   -20

TGGAGCTCATTGGTAAACCAAAACCCTACTATGAG  198
M  E  L  I  G  K  P  K  P  Y  Y  E   21

ATACATGGCTACCTGTCTCAGATGACGCCTGTTAT  318
H  T  W  L  P  V  S  D  D  A  C  Y   61

ACTTTATTTGTAATGAGGGTTATTACTTAATTGGT  438
H  F  I  C  N  E  G  Y  Y  L  I  G  101

CACCTCCAAAAATAAAAAATGGAAAACACACCTTT  558
P  P  P  K  I  K  N  G  K  H  T  F  141

GAGAGAGCACGATTTATTGTGGTGACAATTCAGTG  678
G  E  S  T  I  Y  C  G  D  N  S  V  181

AAAAATTTTACTACAAAGCAACAGTTATGTTTGAA  798
K  K  F  Y  Y  K  A  T  V  M  F  E  221
         pm5.8
TTAAAGTGTCGACTTCTTCCACTACAAAATCTCCA  918
L  K  V  S  T  S  S  T  T  K  S  P  261

TTGACAGTTTGGATGTTTGGGTCATTGCTGTGATT 1038
L  D  S  L  D  V  W  V  I  A  V  I  301
pm5.3, pm5.6, & pm5.10
TAACTGATGAGACCCACAGAGAAGTAAAATTTACT 1158
L  T  D  E  T  H  R  E  V  K  F  T  341

AGACTAAATCAACCACTCCAGCAGAGCAGAGAGGC 1278
                                     343

CATGAGTGCAACTGTGGCTTAGCTAATATTGCAAT 1398
AATAACACTTAGATTTATTGGACCAGTCAGCACAG 1518
TTTTCTTTGTAAAGAAAGTGGCTTGAAATCTTTTT 1638
                                    1659
```

FIG. 1d

```
TGTTCAAAGATTAATGCCAACTCTTAAGATTATTCTTTCACCAACTATAGAATGTATTTTATA
ATAAAAACAAGAACACTGAAAATTGGGAATATGCACAAACTTGGCTTCTTTAACCAAGAATAT
TCGGTGATTTCAGAAAGCTAGAAAGTGTATGTGTGGCATTTGTTTTCACTTTTTAAAACATCC
GAGAGGACTCTGACAGCCATAACAGGAGTGCCACTTCATGGTGCGAAGTGAACACTGTAGTCT
CCG

TATCGTTCATTGTAAAAAGCCCTTAAAAATATGTGTATACTACTTTGGCTCTTGTGC 1758
TATTGGAAAAGTTCTCTAAAAGTTAATAGGGTAAATTCTCTATTTTTTGTAATGTGT 1878
CTAACTGATCGAATATATCAGTAATTTCAGAATCAGATGCATCCTTTCATAAGAAGT 1998
TGTTGTTTTCCCAAAGAGAACTCCGTATGTTCTCTTAGGTTGAGTAACCCACTCTGC 2118
                                                          2121
```

FIG. 3b

```
        GATGAGACCCACAGAGAAGTAAAATTTACTTCTCTCTGAGAAGGAGAGATGAGAGAAAGG 1188
pm5.1    D  E  T  H  R  E  V  K  F  T  S  L ***
pm5.6     -  -  -  -  -  -  -  -  -  -  -  -  -  -  -  -  -  -  -  -
pm5.10   -  -  -  -  -  -  -  -  -  -  -  -  -  -  -  -  -  -  -  -
pm5.3    -  -  -  -  -  -  -  -  -  -  -  -  -  -  -  -  -  -  -  -

        TTTGATTTTATCATTAAAAGGAAAGCAGATGGTGGAGCTGAATATGCCACTTACCAGACT 1248
pm5.6     -  -  -  -  -  -< G  K  Q  M  V  E  L  N  M  P  L  T  R  L
pm5.10   -  -  -  -  -  -  -< K  A  D  G  G  A  E  Y  A  T  Y  Q  T
pm5.3    -  -  -  -  -  -  -< K  A  D  G  G  A  E  Y  A  T  Y  Q  T

        AAATCAACCACTCCAGCAGAGCAGAGAGGCTGAATAGATTCCACAACCTGGTTTGCCAGT 1308
pm5.6     N  Q  P  L  Q  Q  S  R  E  A  E ***
pm5.10   K  S  T  T  P  A  E  Q  R  G ***
pm5.3    K  S  T  T  P  A  E  Q  R  G ***
```

FIG. 3c

```
cDNA    GGTACAAAGGTTATCTTTTTTCTGTCTTGGTTTGTTATTGTTGTTGCTGTTCATTTTAGA   948
pm5.8    G  T  K [V  I  F  F  L  S  W  F  V  I  V  V  A  V  H  F] R

        CTTTATTTCTTTGATATTAACTATCAGTCATACAAAATAACTGAAAAGAAACAATTTTAG  1008
pm5.8    L  Y  F  F  D  I  N  Y  Q  S  Y  K  I  T  E  K  K  Q  F ***

pm5.8   TATTTAACTCTGTCTTGTATTCATTTCTATGCCAGATGAATGACACGAAATTCACATAAA  1068
        ATTCTGCTGTTGTGATTTTTTGTGCTTTTCCAGGGTTCTTAGCACGTTATGTACATTGCA  1128
        TGGGTATATGCTTTTAATATTTTTATGTATAAAAAGTGAATTACAACAACTTTTTGGAAT  1188
        TGAAACATGGGCATTTTTATCTAAGTAAGTCAACAATGGCATAATTCATATACCCG      1244
```

Ethidium bromide stained gel

On63 (spans 93bp deletion)

On46 (within 93bp deletion)

C TGCTGCCTCCATCTAGTACAAAACCTCCAGCTTTGAGTCATTCAG

ValLeuProProSerSerThrLysProProAlaSerSerHisSerVal

D 12 13 14

1) VVGVAVICVVPYRYLQRRKKKG TYLTDETHREVKFTSL*
2) VVGVAVICVVPYRYLQRRKKKG .................. KADGGAEYATYQTKSTTPAEQRG*
3) .............DIFKGGRRK .................. GKQMVELNMPLTRLNQPLQQSREAE*
4) ...................... .................. GKQMVELNMPLTRLNQPLQQSREAE*

FIG. 12

| | TRANSCRIPT NAME | TRANSCRIPT STRUCTURE | Mr (kDa) | ISOFORM | DISTRIBUTION |
|---|---|---|---|---|---|
| a | CD46 (no del) | | 74 | $\gamma$ | PREFERENTIALLY IN EBV-B CELLS & LEUKEMIC CELLS |
| b | CD46 (del 13) | | | | |
| c | CD46 (del 7) | | 66 | $\alpha$ | ALL ISSUES EXCEPT SPERM (UPPER FORM) |
| d | CD46 (del 7, 13) | | | | |
| e | CD46 (del 7, 8) | | 56 | $\beta$ | ALL ISSUES EXCEPT SPERM (LOWER FORM) |
| f | CD46 (del 7, 8, 13) | | | | |
| g | CD46 (del 9) | | 70 | ? | SOME PLACENTAE |
| h | CD46 (del 9, 13) | | | | |
| i | CD46 (del 7, 9) | | 63 | $\varepsilon$ | |
| j | CD46 (del 7, 9, 13) | | | | |
| k | CD46 (del 7, 8, 9) | | ? | ? | SOME PLACENTAE (OBSCURED IN FIG. 1) |
| l | CD46 (del 7, 8, 9, 13) | | | | |
| m | CD46 (del 7, 12a, 13) | | ? | ? | PLACENTAL cDNA CLONES |
| n | CD46 (del 7, 8, 12, 13) | | 35 | $\delta$ | SPERM |

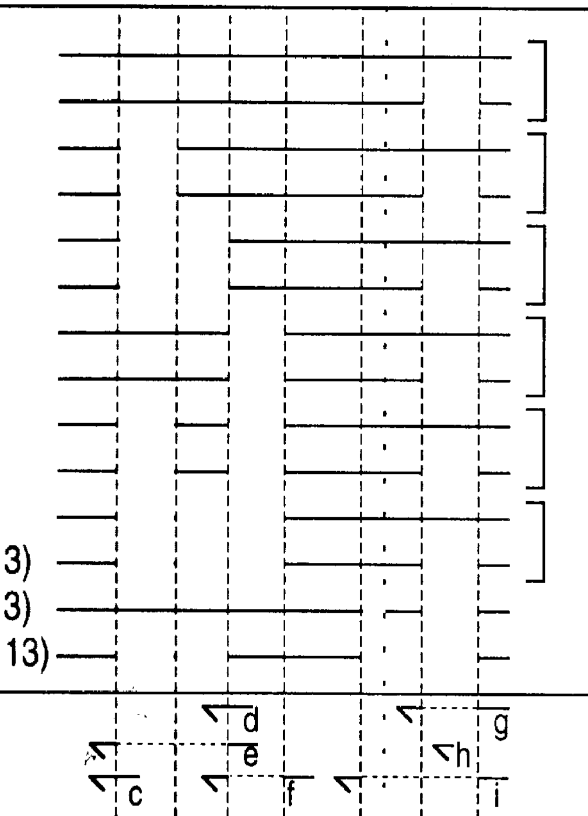

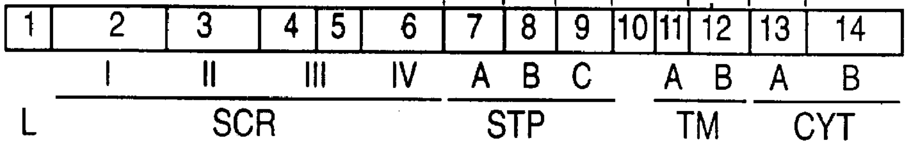

FIG. 13a

Exon 7 (STP A)

TGCTGCCTCCATCTAGTACAAAACCTCCAGCTTTGAGTCATTCAG

| | | | | | | | | | | | | | | | |
|---|---|---|---|---|---|---|---|---|---|---|---|---|---|---|---|
| a | V | L | P | P | S | S | T | K | P | P | A | S | S | H | S |
| b | V | L | P | P | S | S | T | K | P | P | A | S | S | H | S |
| c | . | . | . | . | . | . | . | . | . | . | . | . | . | . | . |
| d | . | . | . | . | . | . | . | . | . | . | . | . | . | . | . |
| e | . | . | . | . | . | . | . | . | . | . | . | . | . | . | . |
| f | . | . | . | . | . | . | . | . | . | . | . | . | . | . | . |
| g | V | L | P | P | S | S | T | K | P | P | A | S | S | H | S |
| h | V | L | P | P | S | S | T | K | P | P | A | S | S | H | S |
| i | . | . | . | . | . | . | . | . | . | . | . | . | . | . | . |
| j | . | . | . | . | . | . | . | . | . | . | . | . | . | . | . |
| k | . | . | . | . | . | . | . | . | . | . | . | . | . | . | . |
| l | . | . | . | . | . | . | . | . | . | . | . | . | . | . | . |
| m | . | . | . | . | . | . | . | . | . | . | . | . | . | . | . |
| n | . | . | . | . | . | . | . | . | . | . | . | . | . | . | . |

FIG. 13b

Exon 8 (STP B)

| | TGTCGACTTCTTCCACTACAAAATCTCCAGCGTCCAGTGCCTCAG | | | | | | | | | | | | | | |
|---|---|---|---|---|---|---|---|---|---|---|---|---|---|---|---|
| a | V | S | T | S | S | T | T | K | S | P | A | S | S | A | S |
| b | V | S | T | S | S | T | T | K | S | P | A | S | S | A | S |
| c | V | S | T | S | S | T | T | K | S | P | A | S | S | A | S |
| d | V | S | T | S | S | T | T | K | S | P | A | S | S | A | S |
| e | . | . | . | . | . | . | . | . | . | . | . | . | . | . | . |
| f | . | . | . | . | . | . | . | . | . | . | . | . | . | . | . |
| g | V | S | T | S | S | T | T | K | S | P | A | S | S | A | S |
| h | V | S | T | S | S | T | T | K | S | P | A | S | S | A | S |
| i | . | . | . | . | . | . | . | . | . | . | . | . | . | . | . |
| j | . | . | . | . | . | . | . | . | . | . | . | . | . | . | . |
| k | V | S | T | S | S | T | T | K | S | P | A | S | S | A | S |
| l | V | S | T | S | S | T | T | K | S | P | A | S | S | A | S |
| m | V | S | T | S | S | T | T | K | S | P | A | S | S | A | S |
| n | . | . | . | . | . | . | . | . | . | . | . | . | . | . | . |

FIG. 13c

Exon 9 (STP C)

GTCCTAGGCCTACTTACAAGCCTCCAGTCTCAAATTATCCAG

| | | | | | | | | | | | | | |
|---|---|---|---|---|---|---|---|---|---|---|---|---|---|
| G | P | R | P | T | Y | K | P | P | V | S | N | Y | P |
| G | P | R | P | T | Y | K | P | P | V | S | N | Y | P |
| G | P | R | P | T | Y | K | P | P | V | S | N | Y | P |
| G | P | R | P | T | Y | K | P | P | V | S | N | Y | P |
| G | P | R | P | T | Y | K | P | P | V | S | N | Y | P |
| G | P | R | P | T | Y | K | P | P | V | S | N | Y | P |
| . | . | . | . | . | . | . | . | . | . | . | . | . | . |
| . | . | . | . | . | . | . | . | . | . | . | . | . | . |
| . | . | . | . | . | . | . | . | . | . | . | . | . | . |
| . | . | . | . | . | . | . | . | . | . | . | . | . | . |
| . | . | . | . | . | . | . | . | . | . | . | . | . | . |
| . | . | . | . | . | . | . | . | . | . | . | . | . | . |
| G | P | R | P | T | Y | K | P | P | V | S | N | Y | P |
| G | P | R | P | T | Y | K | P | P | V | S | N | Y | P |

FIG. 13d

Exons 10/11 (UK / TM A)

GATATCCTAAACCTGAGGAAGGAATACTTGACAGTTTGGATGTTTGGGTCATTGCTGTGATTGTTATTGCCATA

| | | | | | | | | | | | | | | | | | | | | | | | | | |
|---|---|---|---|---|---|---|---|---|---|---|---|---|---|---|---|---|---|---|---|---|---|---|---|---|---|
| a | G | Y | P | K | P | E | E | G | I | L | D | S | L | D | V | W | V | I | A | V | I | V | I | A | I |
| b | G | Y | P | K | P | E | E | G | I | L | D | S | L | D | V | W | V | I | A | V | I | V | I | A | I |
| c | G | Y | P | K | P | E | E | G | I | L | D | S | L | D | V | W | V | I | A | V | I | V | I | A | I |
| d | G | Y | P | K | P | E | E | G | I | L | D | S | L | D | V | W | V | I | A | V | I | V | I | A | I |
| e | G | Y | P | K | P | E | E | G | I | L | D | S | L | D | V | W | V | I | A | V | I | V | I | A | I |
| f | G | Y | P | K | P | E | E | G | I | L | D | S | L | D | V | W | V | I | A | V | I | V | I | A | I |
| g | G | Y | P | K | P | E | E | G | I | L | D | S | L | D | V | W | V | I | A | V | I | V | I | A | I |
| h | G | Y | P | K | P | E | E | G | I | L | D | S | L | D | V | W | V | I | A | V | I | V | I | A | I |
| i | G | Y | P | K | P | E | E | G | I | L | D | S | L | D | V | W | V | I | A | V | I | V | I | A | I |
| j | G | Y | P | K | P | E | E | G | I | L | D | S | L | D | V | W | V | I | A | V | I | V | I | A | I |
| k | G | Y | P | K | P | E | E | G | I | L | D | S | L | D | V | W | V | I | A | V | I | V | I | A | I |
| l | G | Y | P | K | P | E | E | G | I | L | D | S | L | D | V | W | V | I | A | V | I | V | I | A | I |
| m | G | Y | P | K | P | E | E | G | I | L | D | S | L | D | V | W | V | I | A | V | I | V | I | A | I |
| n | G | Y | P | K | P | E | E | G | I | L | D | S | L | D | V | W | V | I | A | V | I | V | I | A | I |

FIG. 13e

Exon 12 (TM B)

GTTGTTGGAGTTGCAGTAATTTGTGTTGTCCCGTACAGATATCTTCAAAGGAGGAAGAAGAAAGG

| | | | | | | | | | | | | | | | | | | | | | |
|---|---|---|---|---|---|---|---|---|---|---|---|---|---|---|---|---|---|---|---|---|---|
| a | V | V | G | V | A | V | I | C | V | V | P | Y | R | Y | L | Q | R | R | K | K | K | G |
| b | V | V | G | V | A | V | I | C | V | V | P | Y | R | Y | L | Q | R | R | K | K | K | G |
| c | V | V | G | V | A | V | I | C | V | V | P | Y | R | Y | L | Q | R | R | K | K | K | G |
| d | V | V | G | V | A | V | I | C | V | V | P | Y | R | Y | L | Q | R | R | K | K | K | G |
| e | V | V | G | V | A | V | I | C | V | V | P | Y | R | Y | L | Q | R | R | K | K | K | G |
| f | V | V | G | V | A | V | I | C | V | V | P | Y | R | Y | L | Q | R | R | K | K | K | G |
| g | V | V | G | V | A | V | I | C | V | V | P | Y | R | Y | L | Q | R | R | K | K | K | G |
| h | V | V | G | V | A | V | I | C | V | V | P | Y | R | Y | L | Q | R | R | K | K | K | G |
| i | V | V | G | V | A | V | I | C | V | V | P | Y | R | Y | L | Q | R | R | K | K | K | G |
| j | V | V | G | V | A | V | I | C | V | V | P | Y | R | Y | L | Q | R | R | K | K | K | G |
| k | V | V | G | V | A | V | I | C | V | V | P | Y | R | Y | L | Q | R | R | K | K | K | G |
| l | V | V | G | V | A | V | I | C | V | V | P | Y | R | Y | L | Q | R | R | K | K | K | G |
| m | . | . | . | . | . | . | . | . | . | . | . | . | . | . | . | . | . | . | . | . | . | . |
| n | . | . | . | . | . | . | . | . | . | . | . | . | D | I | F | K | G | G | R | R | K | |

FIG. 13f

Exon 13 (CYT A)

CACATACCTAACTGATGAGACCCACAGAGAAGTAAAATTTACTTCTCTCTGAGAAGGA...

| | | | | | | | | | | | | | | | | | | | | |
|---|---|---|---|---|---|---|---|---|---|---|---|---|---|---|---|---|---|---|---|---|
| a | T | Y | L | T | D | E | T | H | R | E | V | K | F | T | S | L | *** | | | |
| b | . | . | . | . | . | . | . | . | . | . | . | . | . | . | . | . | . | . | . | . |
| c | T | Y | L | T | D | E | T | H | R | E | V | K | F | T | S | L | *** | | | |
| d | . | . | . | . | . | . | . | . | . | . | . | . | . | . | . | . | . | . | . | . |
| e | T | Y | L | T | D | E | T | H | R | E | V | K | F | T | S | L | *** | | | |
| f | . | . | . | . | . | . | . | . | . | . | . | . | . | . | . | . | . | . | . | . |
| g | T | Y | L | T | D | E | T | H | R | E | V | K | F | T | S | L | *** | | | |
| h | . | . | . | . | . | . | . | . | . | . | . | . | . | . | . | . | . | . | . | . |
| i | T | Y | L | T | D | E | T | H | R | E | V | K | F | T | S | L | *** | | | |
| j | . | . | . | . | . | . | . | . | . | . | . | . | . | . | . | . | . | . | . | . |
| k | T | Y | L | T | D | E | T | H | R | E | V | K | F | T | S | L | *** | | | |
| l | . | . | . | . | . | . | . | . | . | . | . | . | . | . | . | . | . | . | . | . |
| m | . | . | . | . | . | . | . | . | . | . | . | . | . | . | . | . | . | . | . | . |
| n | . | . | . | . | . | . | . | . | . | . | . | . | . | . | . | . | . | . | . | . |

FIG. 13g

Exon 14 (CYT B)

```
   GAAAGCAGATGGTGGAGCTGAATATGCCACTTACCAGACTAAATCAACCACTCCAGCAGAGCAGAGAGGCTGAATAGATTCCAC...
a
b    K  A  D  G  G  A  E  Y  A  T  Y  Q  T  K  S  T  T  P  A  E  Q  R  G ***
c
d    K  A  D  G  G  A  E  Y  A  T  Y  Q  T  K  S  T  T  P  A  E  Q  R  G ***
e
f    K  A  D  G  G  A  E  Y  A  T  Y  Q  T  K  S  T  T  P  A  E  Q  R  G ***
g
h    K  A  D  G  G  A  E  Y  A  T  Y  Q  T  K  S  T  T  P  A  E  Q  R  G ***
i
j    K  A  D  G  G  A  E  Y  A  T  Y  Q  T  K  S  T  T  P  A  E  Q  R  G ***
k
l    K  A  D  G  G  A  E  Y  A  T  Y  Q  T  K  S  T  T  P  A  E  Q  R  G ***
m  G  K  Q  M  V  E  L  N  M  P  L  T  R  L  N  Q  P  L  Q  Q  S  R  E  A  E ***
n  G  K  Q  M  V  E  L  N  M  P  L  T  R  L  N  Q  P  L  Q  Q  S  R  E  A  E ***
```

```
  AATTCGGGGG ACTTCCCTGC TCGGCTGGCT CTCGGTTTCT

 TCCGCGCCGC GC ATG GAG CCT CCC GGC CGC CGC GAG
               Met glu pro pro gly arg arg glu
               -34             -30

CCT GGG TTG CTT CTG GCG GCC ATG GTG TTG CTG CTG
pro gly leu leu leu ala ala met val leu leu leu
            -15                 -10

GAG CCA CCA ACA TTT GAA GCT ATG GAG CTC ATT GGT
glu pro pro thr phe glu ala met glu leu ile gly
         5                   10

GGT GAA CGA GTA GAT TAT AAG TGT AAA AAA GGA TAC
gly glu arg val asp tyr lys cys lys lys gly tyr
        25                   30

CAT ACT ATT TGT GAT CGG AAT CAT ACA TGG CTA CCT
his thr ile cys asp arg asn his thr trp leu pro
        45                   50

GAA ACA TGT CCA TAT ATA CGG GAT CCT TTA AAT GGC
glu thr cys pro tyr ile arg asp pro leu asn gly
        65                   70

TAC GAG TTT GGT TAT CAG ATG CAC TTT ATT TGT AAT
tyr glu phe gly tyr gln met his phe ile cys asn
        85                   90

GAA ATT CTA TAT TGT GAA CTT AAA GGA TCA GTA GCA
glu ile leu tyr cys glu leu lys gly ser val ala
        105                 110

TGT GAA AAG GTT TTG TGT ACA CCA CCT CCA AAA ATA
cys glu lys val leu cys thr pro pro pro lys ile
        125                 130
```

FIG. 14b

```
CTGCTTTCCT CCGGAGAAAT AACAGCGTCT          70

TGT CCC TTT CCT TCC TGG CGC TTT          130
cys pro phe pro ser trp arg phe
    -25                 -20

TAC TCC TTC TCC GAT GCC TGT GAG          190
tyr ser phe ser asp ala cys glu
     -5                   1

AAA CCA AAA CCC TAC TAT GAG ATT          250
lys pro lys pro tyr tyr glu ile
 15                  20

TTC TAT ATA CCT CCT CTT GCC ACC          310
phe tyr ile pro pro leu ala thr
 35                  40

GTC TCA GAT GAC GCC TGT TAT AGA          370
val ser asp asp ala cys tyr arg
 55                  60

CAA GCA GTC CCT GCA AAT GGG ACT          430
gln ala val pro ala asn gly thr
 75                  80

GAG GGT TAT TAC TTA ATT GGT GAA          490
glu gly tyr tyr leu ile gly glu
 95                 100

ATT TGG AGC GGT AAG CCC CCA ATA          550
ile trp ser gly lys pro pro ile
115                 120

AAA AAT GGA AAA CAC ACC TTT AGT          610
lys asn gly lys his thr phe ser
135                 140
```

FIG. 14c

```
GAA GTA GAA GTA TTT GAG TAT CTT GAT GCA GTA
glu val glu val phe glu tyr leu asp ala val
        145                 150

CCA GAT CCA TTT TCA CTT ATT GGA GAG AGC ACG
pro asp pro phe ser leu ile gly glu ser thr
        165                 170

AGT CGT GCT GCT CCA GAG TGT AAA GTG GTC AAA
ser arg ala ala pro glu cys lys val val lys
        185                 190

AAA CAG ATA TCA GGA TTT GGA AAA AAA TTT TAC
lys gln ile ser gly phe gly lys lys phe tyr
        205                 210

GAT AAG GGT TTT TAC CTC GAT GGC AGC GAC ACA
asp lys gly phe tyr leu asp gly ser asp thr
        225                 230

GAT CCC CCA GTT CCA AAG TGT CTT AAA GTG TCG
asp pro pro val pro lys cys leu lys val ser
        245                 250

TCC AGT GCC TCA GGA TAT CCT AAA CCT GAG GAA
ser ser ala ser gly tyr pro lys pro glu glu
        265                 270

GTC ATT GCT GTG ATT GTT ATT GCC ATA GTT GTT
val ile ala val ile val ile ala ile val val
        285                 290

TAC AGA TAT CTT CAA AGG AGG AAG AAG AAA GGG
tyr arg tyr leu gln arg arg lys lys lys gly
        305                 310

ACT TAC CAG ACT AAA TCA ACC ACT CCA GCA GAG
thr tyr gln thr lys ser thr thr pro ala glu
        325                 330

GTTTGCCAGT TCATCTTTTG ACTCTATCCC GCCCG  1247
```

FIG. 14d

```
ACT TAT AGT TGT GAT CCT GCA CCT GGA      670
thr tyr ser cys asp pro ala pro gly
    155                 160

ATT TAT TGT GGT GAC AAT TCA GTG TGG      730
ile tyr cys gly asp asn ser val trp
    175                 180

TGT CGA TTT CCA GTA GTC GAA AAT GGA      790
cys arg phe pro val val glu asn gly
    195                 200

TAC AAA GCA ACA GTT ATG TTT GAA TGC      850
tyr lys ala thr val met phe glu cys
    215                 220

ATT GTC TGT GAC AGT AAC AGT ACT TGG      910
ile val cys asp ser asn ser thr trp
    235                 240

ACT TCT TCC ACT ACA AAA TCT CCA GCG      970
thr ser ser thr thr lys ser pro ala
    255                 260

GGA ATA CTT GAC AGT TTG GAT GTT TGG     1030
gly ile leu asp ser leu asp val trp
    275                 280

GGA GTT GCA GTA ATT TGT GTT GTC CCG     1090
gly val ala val ile cys val val pro
    295                 300

AAA GCA GAT GGT GGA GCT GAA TAT GCC     1150
lys ala asp gly gly ala glu tyr ala
    315                 320

CAG AGA GGC TGAATAGATT CCACAACCTG       1212
gln arg gly
    335
```

FIG. 15a

```
AATTCGGGCG GGGTCTTCCG CGCCGCGC ATG GAG CCT
                               Met glu pro
                               -34

TCC TGG CGC TTT CCT GGG TTG CTT CTG GCG GCC
ser trp arg phe pro gly leu leu leu ala ala
        -20                 -15

GAT GCC TGT GAG GAG CCA CCA ACA TTT GAA GCT
asp ala cys glu glu pro pro thr phe glu ala
          1               5

TAC TAT GAG ATT GGT GAA CGA GTA GAT TAT AAG
tyr tyr glu ile gly glu arg val asp tyr lys
     20                 25

CCT CTT GCC ACC CAT ACT ATT TGT GAT CGG AAT
pro leu ala thr his thr ile cys asp arg asn
     40                 45

GCC TGT TAT AGA GAA ACA TGT CCA TAT ATA CGG
ala cys tyr arg glu thr cys pro tyr ile arg
     60                 65

GCA AAT GGG ACT TAC GAG TTT GGT TAT CAG ATG
ala asn gly thr tyr glu phe gly tyr gln met
     80                 85

TTA ATT GGT GAA GAA ATT CTA TAT TGT GAA CTT
leu ile gly glu glu ile leu tyr cys glu leu
    100                105

AAG CCC CCA ATA TGT GAA AAG GTT TTG TGT ACA
lys pro pro ile cys glu lys val leu cys thr
    120                125

CAC ACC TTT AGT GAA GTA GAA GTA TTT GAG TAT
his thr phe ser glu val glu val phe glu tyr
    140                145
```

```
CCC GGC CGC CGC GAG TGT CCC TTT CCT    64
pro gly arg arg glu cys pro phe pro
    -30                 -25

ATG GTG TTG CTG CTG TAC TCC TTC TCC   124
met val leu leu leu tyr ser phe ser
    -10                  -5

ATG GAG CTC ATT GGT AAA CCA AAA CCC   184
met glu leu ile gly lys pro lys pro
 10                  15

TGT AAA AAA GGA TAC TTC TAT ATA CCT   244
cys lys lys gly tyr phe tyr ile pro
 30                  35

CAT ACA TGG CTA CCT GTC TCA GAT GAC   304
his thr trp leu pro val ser asp asp
 50                  55

GAT CCT TTA AAT GGC CAA GCA GTC CCT   364
asp pro leu asn gly gln ala val pro
 70                  75

CAC TTT ATT TGT AAT GAG GGT TAT TAC   424
his phe ile cys asn glu gly tyr tyr
 90                  95

AAA GGA TCA GTA GCA ATT TGG AGC GGT   484
lys gly ser val ala ile trp ser gly
110                 115

CCA CCT CCA AAA ATA AAA AAT GGA AAA   544
pro pro pro lys ile lys asn gly lys
130                 135

CTT GAT GCA GTA ACT TAT AGT TGT GAT   604
leu asp ala val thr tyr ser cys asp
150                 155
```

FIG. 15c

```
CCT GCA CCT GGA CCA GAT CCA TTT TCA CTT ATT
pro ala pro gly pro asp pro phe ser leu ile
    160                 165

AAT TCA GTG TGG AGT CGT GCT GCT CCA GAG TGT
asn ser val trp ser arg ala ala pro glu cys
    180                 185

GTC GAA AAT GGA AAA CAG ATA TCA GGA TTT GGA
val glu asn gly lys gln ile ser gly phe gly
    200                 205

ATG TTT GAA TGC GAT AAG GGT TTT TAC CTC GAT
met phe glu cys asp lys gly phe tyr leu asp
    220                 225

AAC AGT ACT TGG GAT CCC CCA GTT CCA AAG TGT
asn ser thr trp asp pro pro val pro lys cys
    240                 245

AAA TCT CCA GCG TCC AGT GCC TCA GGT CCT AGG
lys ser pro ala ser ser ala ser gly pro arg
    260                 265

TAT CCA GGA TAT CCT AAA CCT GAG GAA GGA ATA
tyr pro gly tyr pro lys pro glu glu gly ile
    280                 285

GCT GTG ATT GTT ATT GCC ATA GAT ATC TTC AAA
ala val ile val ile ala ile asp ile phe lys
    300                 305

GTG GAG CTG AAT ATG CCA CTT ACC AGA CTA AAT
val glu leu asn met pro leu thr arg leu asn
    320                 325

GAA TAGATTCCAC AACCTGGTTT GCCAGTTCAT CTTTTG
glu ***
```

FIG. 15d

| | | | | | | | | | |
|---|---|---|---|---|---|---|---|---|---|
| GGA | GAG | AGC | ACG | ATT | TAT | TGT | GGT | GAC | 664 |
| gly | glu | ser | thr | ile | tyr | cys | gly | asp | |
| 170 | | | | | 175 | | | | |
| AAA | GTG | GTC | AAA | TGT | CGA | TTT | CCA | GTA | 724 |
| lys | val | val | lys | cys | arg | phe | pro | val | |
| 190 | | | | | 195 | | | | |
| AAA | AAA | TTT | TAC | TAC | AAA | GCA | ACA | GTT | 784 |
| lys | lys | phe | tyr | tyr | lys | ala | thr | val | |
| 210 | | | | | 215 | | | | |
| GGC | AGC | GAC | ACA | ATT | GTC | TGT | GAC | AGT | 844 |
| gly | ser | asp | thr | ile | val | cys | asp | ser | |
| 230 | | | | | 235 | | | | |
| CTT | AAA | GTG | TCG | ACT | TCT | TCC | ACT | ACA | 904 |
| leu | lys | val | ser | thr | ser | ser | thr | thr | |
| 250 | | | | | 255 | | | | |
| CCT | ACT | TAC | AAG | CCT | CCA | GTC | TCA | AAT | 964 |
| pro | thr | tyr | lys | pro | pro | val | ser | asn | |
| 270 | | | | | 275 | | | | |
| CTT | GAC | AGT | TTG | GAT | GTT | TGG | GTC | ATT | 1024 |
| leu | asp | ser | leu | asp | val | trp | val | ile | |
| 290 | | | | | 295 | | | | |
| GGA | GGA | AGA | AGA | AAG | GGA | AAG | CAG | ATG | 1084 |
| gly | gly | arg | arg | lys | gly | lys | gln | met | |
| 310 | | | | | 315 | | | | |
| CAA | CCA | CTC | CAG | CAG | AGC | AGA | GAG | GCT | 1144 |
| gln | pro | leu | gln | gln | ser | arg | glu | ala | |
| 330 | | | | | 335 | | | | |

ACTC TATTAAAATC TTCAATAGTT GTTATTCTGT 1217

FIG. 15e

AGTTTCACTC TCATGAGTGC AACTGTGGCT TAGCTAATAT TGCAATGTGG CTTGAATGTA GGTAGCATCC
TTTGATGCTT CTTTGAAACT TGTATGAATT TGGGTATGAA CAGATTGCCT GCTTTCCCTT AAATAACACT
TAGATTTATT GGACCAGTCA GCACAGCATG CCTGGTTGTA TTAAAGCAGG GATATGCTGT ATTTTATAAA
ATTGGCAAAA TTAGAGAAAT ATAGTTCACA ATGAAATTAT ATTTTCTTTG TAAAGAAAGT GGCTTGAAAT
CTTTTTTGTT CAAAGATTAA TGCCAACTCT TAAGATTATT CTTTCACCAA CTATAGAATG TATTTTATAT
ATCGTTCATT GTAAAAAGCC CTTAAAAATA TGTGTATACT ACTTTGGCTC TTGTGCATAA AAACAAGAAC
ACTGAAAATT GGGAATATGC ACAAACTTGG CTTCTTTAAC CAAGAATATT ATTGGAAAAG TTCTCTAAAA
GTTAATAGGG TAAATTCTCT ATTTTTTGTA ATGTGTTCGG TGATTTCAGA AAGCTAGAAA GTGTATGTGT
GGCATTTGTT TTCACTTTTT AAAACATCCC TAACTGATCG AATATATCAG TAATTTCAGA ATCAGATGCA
TCCTTTCATA AGAAGTGAGA GGACTCTGAC AGCCATAACA GGAGTGCCAC TTCATGGTGC GAAGTGAACA
CTGTAGTCTT GTTGTTTTCC CAAAGAGAAC TCCGTATGTT CTCTTAGGTT GAGTAACCCA CTCTGCCCG

FIG. 16a

```
    AATTCGGTGG ACCCAGAAGG GACTTCCCTG CTCGGCT

   TAACAGCGTC TTCCGCGCCG CGC ATG GAG CCT CCC
                             Met glu pro pro
                             -34

TGG CGC TTT CCT GGG TTG CTT CTG GCG GCC ATG
trp arg phe pro gly leu leu leu ala ala met
    -20                 -15

GCC TGT GAG GAG CCA CCA ACA TTT GAA GCT ATG
ala cys glu glu pro pro thr phe glu ala met
      1               5                  10

TAT GAG ATT GGT GAA CGA GTA GAT TAT AAG TGT
tyr glu ile gly glu arg val asp tyr lys cys
 20                  25                  30

CTT GCC ACC CAT ACT ATT TGT GAT CGG AAT CAT
leu ala thr his thr ile cys asp arg asn his
 40                  45                  50

TGT TAT AGA GAA ACA TGT CCA TAT ATA CGG GAT
cys tyr arg glu thr cys pro tyr ile arg asp
 60                  65                  70

AAT GGG ACT TAC GAG TTT GGT TAT CAG ATG CAC
asn gly thr tyr glu phe gly tyr gln met his
 80                  85                  90

ATT GGT GAA GAA ATT CTA TAT TGT GAA CTT AAA
ile gly glu glu ile leu tyr cys glu leu lys
100                 105                 110

CCC CCA ATA TGT GAA AAG GTT TTG TGT ACA CCA
pro pro ile cys glu lys val leu cys thr pro
120                 125                 130
```

```
GGC TCTCGGTTTC TCTGCTTTCC TCCGGAGAAA          70

 GGC CGC CGC GAG TGT CCC TTT CCT TCC         132
 gly arg arg glu cys pro phe pro ser
 -30                 -25

 GTG TTG CTG CTG TAC TCC TTC TCC GAT         192
 val leu leu leu tyr ser phe ser asp
 -10                  -5

 GAG CTC ATT GGT AAA CCA AAA CCC TAC         252
 glu leu ile gly lys pro lys pro tyr
                  15

 AAA AAA GGA TAC TTC TAT ATA CCT CCT         312
 lys lys gly tyr phe tyr ile pro pro
                  35

 ACA TGG CTA CCT GTC TCA GAT GAC GCC         372
 thr trp leu pro val ser asp asp ala
                  55

 CCT TTA AAT GGC CAA GCA GTC CCT GCA         432
 pro leu asn gly gln ala val pro ala
                  75

 TTT ATT TGT AAT GAG GGT TAT TAC TTA         492
 phe ile cys asn glu gly tyr tyr leu
                  95

 GGA TCA GTA GCA ATT TGG AGC GGT AAG         552
 gly ser val ala ile trp ser gly lys
                 115

 CCT CCA AAA ATA AAA AAT GGA AAA CAC         612
 pro pro lys ile lys asn gly lys his
                 135
```

FIG. 16c

| | | | | | | | | | | |
|---|---|---|---|---|---|---|---|---|---|---|
| ACC | TTT | AGT | GAA | GTA | GAA | GTA | TTT | GAG | TAT | CTT |
| thr | phe | ser | glu | val | glu | val | phe | glu | tyr | leu |
| 140 | | | | | 145 | | | | | 150 |
| GCA | CCT | GGA | CCA | GAT | CCA | TTT | TCA | CTT | ATT | GGA |
| ala | pro | gly | pro | asp | pro | phe | ser | leu | ile | gly |
| 160 | | | | | 165 | | | | | 170 |
| TCA | GTG | TGG | AGT | CGT | GCT | GCT | CCA | GAG | TGT | AAA |
| ser | val | trp | ser | arg | ala | ala | pro | glu | cys | lys |
| 180 | | | | | 185 | | | | | 190 |
| GAA | AAT | GGA | AAA | CAG | ATA | TCA | GGA | TTT | GGA | AAA |
| glu | asn | gly | lys | gln | ile | ser | gly | phe | gly | lys |
| 200 | | | | | 205 | | | | | 210 |
| TTT | GAA | TGC | GAT | AAG | GGT | TTT | TAC | CTC | GAT | GGC |
| phe | glu | cys | asp | lys | gly | phe | tyr | leu | asp | gly |
| 220 | | | | | 225 | | | | | 230 |
| AGT | ACT | TGG | GAT | CCC | CCA | GTT | CCA | AAG | TGT | CTT |
| ser | thr | trp | asp | pro | pro | val | pro | lys | cys | leu |
| 240 | | | | | 245 | | | | | 250 |
| TCT | TGG | TTT | GTT | ATT | GTT | GTT | GCT | GTT | CAT | TTT |
| ser | trp | phe | val | ile | val | val | ala | val | his | phe |
| 260 | | | | | 265 | | | | | 270 |
| CAG | TCA | TAC | AAA | ATA | ACT | GAA | AAG | AAA | CAA | TTT |
| gln | ser | tyr | lys | ile | thr | glu | lys | lys | gln | phe |
| 280 | | | | | 285 | | | | | 290 |

TATGCCAGAT GAATGACACG AAATTCACAT AAAATTCTGC

CTTAGCACGT TATGTACATT GCATGGGTAT ATGCTTTTAA

AACTTTTTGG AATTGAAACA TGGGCATTTT TATCTAAGTA

FIG. 16d

```
GAT GCA GTA ACT TAT AGT TGT GAT CCT      672
asp ala val thr tyr ser cys asp pro
                155

GAG AGC ACG ATT TAT TGT GGT GAC AAT      732
glu ser thr ile tyr cys gly asp asn
                175

GTG GTC AAA TGT CGA TTT CCA GTA GTC      792
val val lys cys arg phe pro val val
                195

AAA TTT TAC TAC AAA GCA ACA GTT ATG      852
lys phe tyr tyr lys ala thr val met
                215

AGC GAC ACA ATT GTC TGT GAC AGT AAC      912
ser asp thr ile val cys asp ser asn
                235

AAA GGT ACA AAG GTT ATC TTT TTT CTG      972
lys gly thr lys val ile phe phe leu
                255

AGA CTT TAT TTC TTT GAT ATT AAC TAT     1032
arg leu tyr phe phe asp ile asn tyr
                275

TAGTATTTAA CTCTGTCTTG TATTCATTTC        1095

TGTTGTGATT TTTTGTGCTT TTCCAGGGTT        1165

TATTTTTATG TATAAAAAGT GAATTACAAC        1235

AGTCAACAAT GGCATAATTC ATATACCCG         1304
```

CD46 VARIANTS

This application is a continuation-in-part of application Ser. No. 07/961,686, filed Jan. 11, 1993, abandoned (which is the National Phase of PCT/AU91/00199 filed on May 10, 1991.

BACKGROUND OF THE INVENTION

This invention generally relates to the protein CD46, a molecule that exists on the surface of almost all human cells to protect them from destruction by the normal immune processes. The invention also relates to nucleic acid encoding CD46, and vectors and cells containing such nucleic acid.

SUMMARY OF THE INVENTION

The human immune system operates on several levels of specificity and efficiency to identify and eliminate foreign organisms and substances without damaging or destroying normal (or autologous) cells. The complement proteins in serum form a relatively non-specific arm of immunity that plays a leading role in the initial detection, destruction and removal of foreign substances, and in triggering the specific arms of the immune response; formation of antibody and cell-mediated immunity and inflammation mediated responses. The complement proteins also play an important role in the later phases of an immune response by facilitating the phagocytosis of debris and the transport of immune-complexes and macromolecular debris to the liver or spleen for further processing and destruction. The central molecule in the complement system is C3b which aggregates in increasing amounts on foreign substances or organisms tagging them for removal. The complement precursor proteins are activated to form C3b in two ways: (i) by interacting with antibody bound to the foreign target (the classical pathway) or (ii) non-specifically, by progressive and rapidly increasing accumulation on foreign surfaces (the alternative pathway). In order to control this process of complement activation and protect normal cells and tissues from indiscriminate destruction, a family of cell-surface molecules have evolved that interact with C3b molecules; these are:

(i) CD46 (also known as membrane cofactor protein [MCP]) which exists on all normal human cells, except red blood cells, and binds to C3b and activates molecules that cleave C3b into inactive fragments before it can accumulate sufficiently to destroy the cell.

(ii) CD55 (also known as decay accelerating factor [DAF]) which exists on all cells, including red blood cells, and prevents C3b from reacting with other complement components preventing the destructive processes, however, unlike CD46, this does not destroy C3b.

(iii) CD35 (or complement receptor 1 [CR1]) which exists on a select group of leukocytes and causes the degradation of C3b molecules adhering to neighbouring cells.

CD46 and CD55 (MCP and DAF) are the predominant molecules protecting normal autologous tissues from complement-mediated destruction. The absence of these C3b receptors on foreign cells or substances labels them as foreign and promotes their destruction.

Leukaemia cells and other malignant tumour cells express a greatly elevated level of CD46 at their surface which is biochemically and structurally different (but still related to CD46) on the corresponding non-malignant cell. The surface molecules of primate retroviruses that cause leukaemia and AIDS, the gibbon ape leukaemia (GaLV) and Mason-Pfizer monkey (MPMV) viruses, have a structural-protein component that resembles CD46 as demonstrated by the binding of the monoclonal antibody E4.3 (the benchmark reagent defining CD46) to these viral molecules. The existence of these altered (or mimicked) versions of CD46 in high levels on tumour cells and viruses is likely to enhance their evasion of complement-mediated immunity.

CD46 also appears to play an important role in human reproduction as human spermatozoa express high levels of a novel form of CD46 at the surface after the acrosome reaction. This occurs prior to fusion of sperm with the oocyte. CD46 molecules are also secreted extracellularly from the spermatozoa after the acrosome reaction. These findings suggest that CD46 plays an important role in the process of fertilization and recombinant (synthetic) CD46 may facilitate the process of fertilization.

The layer of syncytiotrophoblast cells in the placenta, the interface between the mother and the antigenically different fetus, expresses higher levels of CD46 than any other tissue. CD46 is the same as the TLX molecule identified by reproductive immunologists as a crucial molecule protecting the non-identical fetus tissues from immune-rejection by the mother. It is possible that in addition to the ability to regulate the activation of complement, CD46 dampens the specific immune responses, even the strong response to genetically different cells.

CD46 is thus an important molecule regulating the immune response and may have a role in preventing complement-mediated tissue damage, to enhance immunity to tumours and viruses, to control the process of fertilization, to prevent recurrent spontaneous abortion of the fetus during pregnancy, and to facilitate the engrafting of transplanted tissues.

The CD46 polypeptide has been identified by gel electrophoresis as a heterogenous group of glycoproteins resolving in two diffuse bands known as the α and β chains, having molecular weight of 56,000 and 60,000 daltons respectively, which are not linked by disulphide bonds. The α and β chains of CD46 have been shown to have the same N-terminal amino acid sequence. It has previously been thought that the differences between the α and β chain may be due to glycosylation differences.

This invention arises from the surprising discovery that there are at least fourteen RNA splice variants encoding CD46 molecules. As will be hereinafter described, the various CD46 splice variants have a conserved N-terminus but different protein sequences at the carboxyl-terminal end.

Broadly speaking, the invention encompasses a recombinant nucleic acid encoding a CD46 isoform, the nucleic acid comprising a splice variant of the structural gene encoding the CD46 family of proteins with the proviso that the splice variant does not consist of exons 1 to 6, 8 to 12 and 14 (as herein defined) of the structural gene. The invention thus excludes the published sequence of MCP appearing in Lublin et al. (1988) J. Exp. Med., 168, 181–184.

In accordance with one aspect of this invention there is provided a recombinant nucleic acid encoding a CD46 isoform or derivative, wherein the nucleic acid;

(a) comprises a portion of the sequence depicted in FIGS. 1*a*–1*d* (SEQ ID NO:1), including addition, substitution and deletion derivatives of the sequence not deleteriously affecting the CD46 character of the sequence;

(b) comprises at least one exon or a substantial portion of at least one exon from amongst exon numbers 7 to 14 of FIG. 1; with the proviso that (c) the nucleic acid does not consist of the combination of exons 1 to 6, 8 to 12 and 14.

The exon structure and assignment of the sequence of FIGS. 1*a*–1*d* is discussed in more detail in Examples 4 to 7 which follow. Briefly, the sequence depicted in FIGS. 1*a*–1*d*

(SEQ ID NO:1) corresponds to a leader peptide encoded by a single exon (exon 1), four extracellular short consensus repeat (SCR) domains (characteristic of the family of complement regulating proteins as described by Lublin et al. (1988) J. Exp. Med. 168, 181–194) encoded by exons 2–6, an extracellular region rich in Ser Thr and Pro residues (STP) encoded by exons 7 to 9, a short region of unknown significance (exon 10), a hydrophobic membrane spanning region (TM) encoded by exons 11 and 12 and a short cytoplasmic tail (CYT) encoded either by exon 13 or exon 14, each of which contain a stop codon.

Some embodiments of nucleic acid in accordance with this invention correspond to spliced variants of mRNA encoded by the structural gene-encoding CD46. The term "nucleic acid" as used herein generally refers to DNA, such as cDNA. However, this term also embraces mRNA. Nucleic acid encoding CD46 isoforms or derivatives specifically excludes the known nucleotide sequence encoding the protein known as MCP, which we have now found corresponds to nucleic acid encoding a specific CD46 variant referred to herein as pm5.10 (see FIG. 3, SEQ ID NO:7). Nucleic acid encoding CD46 may refer only to those sequences which encode amino-acids of a CD46 isoform or derivative, or may refer to a nucleic acid containing both coding and non-coding sequences, such as 3' and 5' untranslated sequences.

The nucleic acid of the invention is however not limited to sequences which are alternatively spliced to encode whole native CD46 proteins. Smaller nucleic acid sequences produced by deletion of further exons during RNA splicing or by alternative truncating techniques within exons (such as with stop codons introduced by site directed mutagenesis or with restriction endonucleases) will also be useful as will variants in which native splicing boundaries are overrun allowing expression of intron sequences to be appended to the CD46 isoform. Generally, however, at least a substantial portion (i.e. 50% of the bases) of one or more of exons 7 to 14 is present.

In particular a sequence coding for one or more of the SCR regions but not including, or with much truncated, transmembrane or cytoplasmic domains may produce a soluble CD46, analogous to the soluble CR1 proteins described in Weisman et al, Science 249 146–151 (1990). It should be noted that soluble CD46 variants have been observed in seminal fluid, saliva and serum and these isoforms appear to have a role in fertilization at least, perhaps by mopping up free complement thereby preventing sperm lysis. Relatively short CD46 derivatives, even those having the SCR regions deleted, may be useful to raise antibodies against particular native CD46 variants, thus creating the basis for tissue specific "magic bullets".

Alternatively a nucleic acid somewhat shorter than those encoding native CD46 variants will find utility as probes or as antisense therapeutic agents to disrupt expression of particular CD46 variants. Useful nucleic acid fragments of the sequence of FIG. 1 will generally contain 10 or more nucleotides but will be longer depending on the degree of homology and stringency conditions desired. A probe will typically comprise a segment of the nucleic acid sequence of FIGS. 1*a*–1*d* (SEQ ID NO:1) (including variants not deleteriously affecting the CD46 character of the relevant segment) and a detectable marker such as a fluorophore, radioisotope, gold, biotin etc. A representative use for such a probe is the diagnosis of leukaemia. As can be seen in the following examples we have shown that exon 7 may be uniquely expressed in leukaemia and Epstein Barr virus transformed cells, providing a distinctive target for diagnosis or therapy.

For example, antibodies whose specificity was directed to exon 7 gene products would react preferentially with leukaemic cells rather than normal tissues which have a lower expression of this site. In a similar way reagents could diagnose the presence of either the cells or secreted products from these cells which could be used in diagnostic procedures. This unique sequence could be used for both diagnosis and therapy. In addition, antisense oligonucleotides directed selectively to this exon could inhibit the production not only of this exon but of the whole molecule. Such cells would then not express CD46 and could be susceptible to lysis by complement and lead to selective destruction of tumours.

The polynucleotides, including DNA and RNA, and polypeptides of the present invention are preferably isolated. The term "isolated" in the context of the present invention denotes a separation of the polynucleotides and polypeptides from its original source or surroundings.

Preferably, the polynucleotides and polypeptides are brought to a more purified state. That is, the polynucleotides and polypeptides are substantially free of contaminants that otherwise would be present. Typically, the presence of contaminating nucleic acids and proteins are eliminated or greatly reduced.

The polynucleotides and polypeptides of the present invention can be purified by a variety of techniques, including gel electrophoresis (agarose or SDS-PAGE), isoelectric focusing, ion exchange chromatography, gel exclusion chromatography, affinity chromatography, immunoprecipitation, and combinations thereof.

The present invention is not limited to the exact nucleotide and amino acid sequences set forth herein. For example, the skilled artisan relying upon this specification can make changes in nucleotide sequences based upon the degeneracy of the genetic code. Furthermore, other changes in the amino acid sequence of the CD46 molecule and variants are contemplated in the present invention. The CD46 molecule and variants can be altered by changing the DNA encoding the protein. Preferably, only conservative amino acid alterations, using amino acids that have the same or similar properties, are undertaken. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of the CD46 molecule can be made according to the present invention. These variants include analogs, homologs, derivatives, muteins and mimetics of the CD46 protein that retain the ability to cause the beneficial results described herein. Fragments of the CD46 molecule refer to portions of the amino acid sequence of the CD46 molecule that also retain this ability. Other CD46 variants and fragments can be generated directly from the CD46 molecule, or variants described herein, by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of the CD46 molecule and variants, referred to as "mimetics," can be produced by the approach outlined in Saragovi et al., *Science* 253: 792–95 (1991). Mimetics are molecules which mimic elements of protein secondary structure. See, for example, Johnson et al., "Peptide Turn Mimetics" in BIOTECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of the CD46 molecule and variants thereof.

Nucleic acid falling within the invention include those encoding a CD46 C-terminal variant and include the following:

PM5.1—a nucleic acid encoding a protein of about 377 amino acids, and being characterised by having:

(i) a first region encoding four contiguous substantially homologous units of approximately 60 amino acids and referred to as SCR (short consensus repeats);

(ii) a second region encoding a serine-threonine rich sequence of approximately 45 amino acids;

(iii) a third region encoding a transmembrane domain of approximately 23 amino acids; and (iv) a fourth region encoding a 26 amino acid cytoplasmic domain containing predominantly charged amino acids.

The complete nucleotide sequence of PM5.1 is given in FIGS. 1*a*–1*d* (SEQ ID NO:1).

PM5.3—A nucleic acid corresponding to PM5.1 with the exception that:

(i) a 42 base pair fragment encoding 14 amino acids is deleted from the second, serine-threonine rich, region; and (ii) a 93 base pair fragment is deleted from the fourth region encoding the cytoplasmic tail.

Due to the loss of a termination codon this encodes a variant cytoplasmic tail having the first seven amino acids of the PM5.1 cytoplasmic tail, and then a further 23 amino acids arising from 3' untranslated sequences of PM5.1.

The variant C-terminus of PM5.3 is shown in FIGS. 3*a*–3*c* (SEQ ID NO:4).

PM5.6—A nucleic acid corresponding to PM5.1 with the exception that as for PM5.3, a 93 base pair fragment is deleted from the fourth region encoding the cytoplasmic tail. Additionally, a 37 base pair fragment is deleted from the transmembrane region (encoding the last 12 amino acids thereof) due to the use of a cryptic splice acceptor signal. The absence of this fragment changes the reading frame of the carboxy terminal end of CD46 to encode a peptide having 34 amino acids distinct from those encoded by other CD46 nucleic acids.

The C-terminal sequence of PM5.6 is shown in FIGS. 3*a*–3*c* (SEQ ID NO:4).

PM5.8—A nucleic acid corresponding in part to 5.1 with the exception that those regions after the first region encoding the contiguous SCR regions are replaced with an intron sequence encoding 16 hydrophobic amino acids.

The C-terminal nucleotide sequence of PM5.8 is also given in FIGS. 3*a*–3*c* depict (SEQ ID NO:9).

Further representative sequences are depicted in FIG. 12 (with the exception of transcript d which corresponds to the prior art sequence of MCP).

Transcript a. This sequence was derived by PCR and contains all exons. It encodes a high $M_r$ protein 74 kDa) known as the γ isoform and is preferentially expressed in EBV transformed cells and leukaemic cells. It contains the new sequence of STP A encoded by exon 7.

Transcript b is similar to transcript a but exon 13 has been deleted which gives rise to a new cytoplasmic tail. This form also has a high molecular weight and is found in EBV transformed and leukaemic cells.

Transcript c. This transcript was identified by clone pm5.1 and has exon 7 deleted. It gives rise to the α chain ($M_r$ 66 kDa) which is found in all tissues except sperm.

Transcript d. This transcript has exons 7 and 13 deleted and gives rise to the 66 kDa α chain found in all tissues except sperm. It is probably the commonest form identified and corresponds to clone pm5.10/MCP although the published sequence of MCP is missing the 3' untranslated region and pm5.10 is missing the 5' untranslated region and leader sequence and first three SCR amino acids. It should be noted that transcripts c and d give rise to the same sized protein on gels as the deletions do not give rise to a large difference in molecular weight.

Transcript e has deletions of exons 7 and 8 and is found in all tissues except sperm and gives rise to 56 kDa β isoform of CD46.

Transcript f is similar to transcript e, but with a different cytoplasmic tail due to the deletion of exon 13. It should be noted that the polymorphism effecting the differential expression of exon 8 gives rise to the major changes in molecular weight found in the α and β chain. Thus there are individuals who are α:α; α:β; and β:β.

Transcript g has deleted exon 9 and gives rise to an isoform of 70 kDa and is found in some placentae.

Transcript h is similar to transcript g but with the alternative cytoplasmic tail.

Transcript i has exons 7 and 9 deleted giving rise to 63 kDa isoform (ξ) found in some placenta.

Transcript j is similar with the alternative cytoplasmic tail.

Transcript k has deletions of exons 7, 8 and 9.

Transcript l—the same exons are deleted in addition as an alternative cytoplasmic tail due to the deletion of exon 13.

Transcript m has deletion of exons 7 and 13 and part of exon 12. This arises from the use of an alternative cryptic splice acceptor sequence so that part of exon 12 can be used. This was identified originally by a clone pm5.6.

Transcript n has exons 7, 8, 12 and 13 deleted giving rise to low molecular weight form of 35 kDa (the δ isoform found in the sperm).

The nucleic acid sequence according to the present invention, such as those described above may be modified by the substitution, deletion or insertion of one or more nucleotides. Such variants would include naturally occurring allelic variants, as well as variants produced artificially by well known techniques, such as site directed mutagenesis. CD46 proteins encoded by such derivative nucleotide sequences may have activity characteristic of CD46 or the corresponding portion thereof as described herein or conceivably result in enhanced CD46 activity, particularly as regards solubility, half-life, potency, specificity or localisation.

The discovery underlying this invention, that the family of CD46 proteins appear to arise as splice variants of a stuctural gene allows the identification and isolation of additional splice variants not specifically set forth herein. Such additional variants may arise from further splicing permutations of the exons described herein and/or incorporate additional exons. To isolate such additional variants, a nucleic acid probe comprising say 10 or more bases from the sequence of FIG. 1 could be used to probe preparations of tissues or body fluids to detect members of the CD 46 family sharing exon usages. The preparation probed may comprise a nucleic acid preparation isolated from the tissue, a fixed tissue section or an homogenate of the tissue and use probing techniques and assays known in the art.

The probing techniques described immediately above may also find utility in diagnosis of aberrant isoforms or particular isoforms implicated in the susceptibility, severity or prognosis of diseases. Preliminary indications suggest that CD46 structure may be significant in systemic lupus erythematosis.

In a further aspect, this invention extends to a transfer or expression vector which encodes a nucleic acid in accordance with this invention. Transfer or expression vectors include plasmid and viral DNAs, or viral RNA, but are not limited thereto. Any vehicle capable of replication in a host cell, whether prokaryotic or eukaryotic, is within the scope of this invention. Generally, but without limitation, a transfer or expression vector in accordance with this invention will include an origin of replication, promoter, selective marker (such as antibiotic resistance), and a nucleic acid sequence encoding CD46 as herein described, under the control of a promoter.

In another aspect, the invention relates to a cell containing a transfer or expression vector in accordance with this invention and CD46 produced by such a cell. Suitable cells may be prokaryotic or eukaryotic. The nature of the cell is generally unimportant as long as the transfer vector is capable of replication and desirably expressing therein. Eukaryotic cells are generally used when CD46 is to be post-translationally modified by the addition of carbohydrate, etc. Prokaryotic cells, such as bacterial strains, are preferred when post translational modification is not desired or is considered unimportant. For instance, vectors pAV009/$A^+$, pKC3 and pEE6/hCMV/GSCDM8 and other vectors are appropriate for expression in Cos and Chinese hamster ovary cells. pGEX-3X is useful for prokaryotic expression in *E. coli*. We have observed that sequences encoding CD46 isoforms contain two possible translational start sites (rather than the single site originally reported). Although the 5'-most ATG is preferred this site does not appear to be in the optimal sequence context in the CD46 family of proteins. Accordingly to improve expression PCR can be used to amend the 5' ATG to the consensus sequence or the 5' ATG removed to allow more effective translation from the distal ATG. Similarly, as untranslated regions of some RNAs may effect stability of the RNA and translation efficiency, removal of 3' and 5' untranslated regions, for instance by PCR may be desirable.

Vectors containing CD46 nucleic acid sequences may be introduced into cells by well known methods such as electroporation, conjugation, calcium phosphate precipitation, transformation of competent cells (such as bacterial cells after treatment with $CaCl_2$) and the like. In an alternative aspect, this invention includes cells having nucleic acid encoding CD46 as described herein integrated into the host chromosome.

CD46 produced by host cells may be isolated by protein purification techniques such as chromatography on size-exclusion or ion exchange matrices, HPLC, protein precipitation, affinity chromatography (using, for example, antibodies directed against CD46) and like techniques which are well known in the art. A further aspect of this invention provides essentially pure CD46 isoforms or derivatives translated from a nucleic acid in accordance with this invention.

CD46 isoforms or derivatives may be varied relative to native isoforms by the deletion, insertion or addition of one or more amino acids. Variations may be naturally occurring such as allelic variants or may be produced by well known techniques such as site directed mutagenesis or solid phase peptide synthesis or the like. Such variants are included within this invention as are fragments of the CD46 protein sequence. CD46 variants may possess biological or immunological activity the same or similar to that of CD46.

The CD46 protein sequence may be subject to side chain modifications such as:

Modifications of amino groups including

- Reductive alkylation by Schiff's base formation by an aldehyde followed by reduction with $NaBH_4$.
- Amidination with methylacetimidate.
- Acylation with acetic anhydride.
- Carbamoylation of amino groups with cyanate.
- Trinitrobenzylation of amino groups with 2,4,6, trinitrobenzene sulphonic acid (TNBS).
- Acylation of amino groups with succinic anhydride and tetrahydrophthalic anhydride.
- Pyridoxylation of lysine with pyridoxal-5'-phosphate followed by reduction with $NaBH_4$.

Modification of the guanidino group of Arg by the formation of heterocyclic condensation products with reagents such as 2,3 butanedione, phenylglyoxal and glyoxal.

Modification of carboxyl groups by carbodiimide activation via O-acylisourea formation followed by subsequent derivitisation e.g. to a corresponding amide.

Modification of sulphydryl groups including

- Carboxymethylation with iodoacetic acid or iodoacetamide.
- Performic acid oxidation to cysteic acid.
- Formation of a mixed disulphide with 5,5' dithiobis(2-nitrobenzoic acid) (DTNB).
- Reaction with maleimide, maleic anhydride or other substituted maleimide. Formation of mercurial derivatives using 4-chloromercuribenzoate, 4-chloromercuriphenylsulphinic acid, phenylmercury chloride, 2-chloromercuri-4-nitrophenol and other mercurials.
- Carbamoylation with cyanate at alkaline pH.

Modification of imidazole ring of histidine including

- Alkylation with iodoacetic acid derivatives and
- N-carbethoxylation with diethylpyrocarbonate.

Modification of tryptophan residues including

- Oxidation of N-bromosuccinimide.
- Alkylation of the indole ring with 2-hydroxy-5-nitrobenzyl bromide or sulphenyl halides.

Modification of the tyrosine residues

- Nitration with tetranitromethane to form 3-nitrotyrosine derivatives. Modifications as set out above may be produced according to standard chemical reactions well known in the art.

CD46 and variants and fragments thereof as herein described may be provided in the form of therapeutic compositions in association with one or more pharmaceutically acceptable carriers or excipients. Examples of carriers or excipients which may be utilized in this invention are provided in Remington's Pharmaceutical Sciences 16th Ed, 1980, Mack Publishing Company, Osoll et al, which is incorporated herein by reference. By way of example only, CD46 and variants and fragments thereof may be in association with saline, albumin, water, dextrose or the like. The invention thus extends to the use of the CD46 isoform or derivative produced in accordance with the invention in the manufacture of a medicament. Furthermore, as foreshadowed above, antibodies directed against epitopes encoded by the STP, UK, TM and CYT regions will also have utility in diagnosis and therapy. Therefore CD46 derivatives presenting such epitopes, typically somewhat truncated relative to native proteins, as well as mono or polyclonal antibody preparations directed thereto form a still further aspect of the invention. Epitopes to raise such antibodies may be constructed as synthetic oligonucleotides following the sequences herein or alternatively be expressed from a recombinant nucleic acid of the invention. Technology for raising antibodies to such epitopes including providing haptens or adjuvants and for immortalizing cell lines to produce monoclonal cell lines are well known and need not be described here.

CD46 isoforms or derivatives in accordance with this invention may be utilised to prevent complement-mediated or inflammation mediated tissue damage, to enhance immunity to tumours and viruses, to control the process of fertilization, to prevent recurrent spontaneous abortion of the fetus during pregnancy and to facilitate the engrafting of transplanted tissue.

For example inhibition reactions of complement activation in the classical pathway are initiated by antibody binding to antigen and examples are blood transfusion reactions, glomerulonephritis, Goodpasture's syndrome, systemic lupus erythematosis, rheumatoid arthritis, graft rejection and other diseases where antibody interact with antigen. In addition, certain aspects of cellular immunity are mediated by the complement pathway such as complement receptor on macrophages, polymorphs and other cells binding to antigen-antibody-complement complexes, CD46 isoforms or derivatives in accordance with the invention could inhibit such reactions. In addition, CD46 isoforms or derivatives would be expected to inhibit the alternative pathway activated by inflammatory mediators, bacteria and other substances. Such activation occurs in most inflammatory conditions not necessarily of antibody, i.e. immunological, origin. For example, inflammation which occurs in myocardial infarction, hepatitis, pneumonia, gastroenteritis; indeed inflammation of any organ. Certain aspects of the inflammation are beneficial, i.e. to eradicate bacteria, viruses and the like. However, certain aspects of inflammation are non-specific and cause tissue damage. Soluble CD46 could inhibit such non-specific reactions.

An example of the diagnostic and therapeutic utility of the CD46 isoform or derivative nucleic acids or proteins is described above with regard to exon 7 expression in leukaemic cells. Additionally, in placenta there are clear differences in placental tissue of some individuals compared to others. For example, it is clear that some individuals have deletions found in transcripts g, h, i, j, k and l discussed above. These members of the CD46 family of proteins which are apparently synonymous with the TLX antigen (trophoblast leukocyte cross-reactive antigen) have been associated with habitual abortion in certain individuals. Some of these polymorphisms defined in the present invention may be associated with habitual abortion. It is, therefore, not unlikely that the presence or absence of exons found in certain sequences falling within the broad scope of the invention are responsible for retention/rejection of the fetus in pregnancy. From this, diagnostic tests, for instance nucleic acid probing of maternal or fetal tissue or fluids could be performed to determine which individuals are likely to abort. Administration of a soluble CD46 may serve to mop up surrounding complement to maintain a pregnancy in an habitually aborting mother. Antibodies or antisense oligonucleotides in accordance with the invention will be useful to cause or prevent the expression of these exons and thus overcome the problem of habitual abortion.

A further utility of nucleic acids and CD46 or derivative proteins in accordance with the invention lies in the field of male infertility and encouraging fertilization. It has been observed above that certain of the CD46 family are uniquely expressed on sperm cells, presumably to inhibit complement activated lysis. Individuals with azospermia may be diagnosed with antibodies or probes in accordance with the invention, directed to the unique structure of the sperm CD46. As mentioned above soluble CD46 promises to be useful in mopping up complement to facilitate survival of otherwise vulnerable sperm or to otherwise prevent inhibition of sperm function i.e. migration, penetration, motility or fertilization. It is also likely that CD46 on the sperm is part of a receptor complex responsible for sperm binding to oocytes prior to fertilization. It will be apparent that nucleic acids or CD46 proteins or derivatives will be useful in fertility control.

Nucleic acids and CD46 proteins or derivatives in accordance with the invention also find utility in transplantation. In the rejection of allografts, i.e. from one human to another, T cells are involved and establish inflammatory mechanisms. CD46 could inhibit such non-specific inflammatory reactions occurring after the specific event. In addition, allo-antibodies are involved either in hyperacute rejection or in the late phase of rejection and these act using complement. CD46 may also inhibit this procedure. With regard to xenotransplantation, i.e. form one species to another, it is possible that CD46 could have several actions. In the first soluble material could inhibit the action of complement which is involved in rejection. In the second, transgenic animals could be made expressing CD46 on the cell surface and any or all of the variants could be used for such a procedure. In this setting, one could envisage such species as pigs, sheep or other species expressing human CD46 being used for transplantation experiments. The human CD46 in these organs would break down complement as it was deposited and make the tissues resistance to complement mediated lysis. It is possible that such xenografts could become universal donors for transplants to humans. The pm5.1 clone, containing the CYT 1 tail, is the most likely candidate for this function as it has been shown to have increased cell surface expression compared to clones with the CYT 2 tail as for instance expressed in MCP or pm5.3, pm5.10.

Specific embodiments of the present invention will now be described by way of example only, with reference to the following non-limiting Figures and Examples.

BRIEF DESCRIPTION OF THE FIGURES

FIG. 1A shows the complete nucleotide sequence and predicted amino acid sequence of the pm5.1 cDNA clone of CD46 (SEQ ID NOS:1 and 2, respectively). The $NH_2$-terminal amino acid sequence obtained from purified CD46 glycoprotein is underlined; potential addition sites for N-linked carbohydrate are marked with an asterisk; the region boxed with a hashed line is rich in Ser/Thr residues—potential O-linked glycosylation sites; the region boxed with a solid line is the hydrophobic transmembrane domain. The regions within the labelled arrows are the segments of DNA deleted by the other clones, all of the sequence beyond the arrow labelled pm5.8 has been exchanged for new sequence in the pm5.1 clone.

FIG. 1B shows the sequence (SEQ ID NO:3) of additional nucleotides in the 3' untranslated region of the pm5.6 clone, which is longer than the pm5.1 sequence shown in FIG. 1A. The numbering corresponds to the position relative to the pm5.1 clone and does not take account of the 130 bp deleted from the coding sequence of pm5.6.

FIGS. 3*a*–3*c* depict the alternate carboxyl-terminal protein sequences deduced from the nucleotide sequences of the different cDNA clones for CD46 commencing from amino acid 252. The amino acid sequences encoded by the pm5.1 (SEQ ID NO:5), pm5.6 (SEQ ID NO:6), pm5.10 (SEQ ID NO:7), and pm5.3 (SEQ ID NO:8) clones are shown in (A) the regions of DNA deleted in these clone is denoted by the arrows above the pm5.1 DNA sequence (SEQ ID NO:4) and the dashes (-) in the protein sequence. The DNA and amino acid sequence of pm5.8 (SEQ ID NOS:9 and 10, respectively) that differs to that of the other clones is shown in (B) but is numbered relative to the pm5.1 clone. The regions of hydrophobic amino acids are shown with a solid box and regions rich in Ser and Thr residues are shown with a hatched box.

Figure 2:
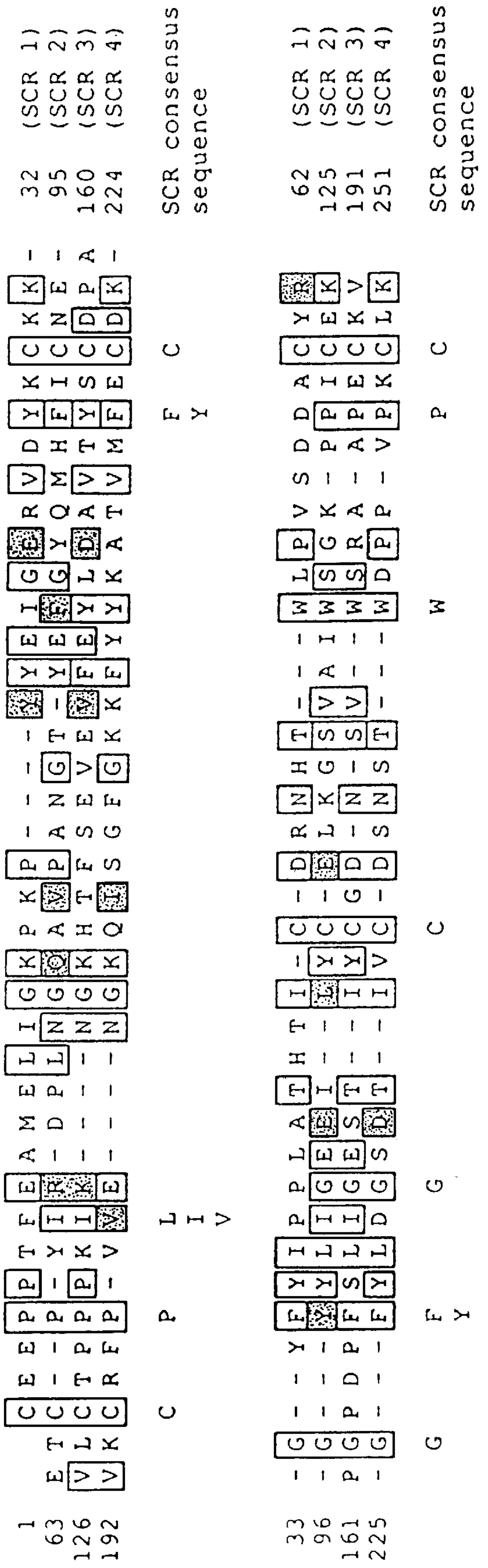
FIG. 2 shows the alignment of the $NH_2$-terminal 251 amino acids of the mature CD46 protein (residues of 1–251 of SEQ ID NO:2) showing the four domains of internal homology, indicated by the boxes. Conservative substitutions are shaded. Spaces (-) have been introduced to maximise alignment. The alignment of these internally conserved residues with the consensus sequence of the 60- amino acid short consensus repeats of the complement regulatory proteins is shown at the bottom.

FIGS. 11C–11I Tissue distribution of individual exon combinations. Unlabelled, amplified cDNA from the same samples as 11B were electrophoresed, electroblotted and probed with oligonucleotides specific for different exons or exon combinations (see FIG. 12 for locations of probes).

C) exons 6–7 (SEQ ID NO:33): 5'-CTAGATGGAGGCA GCACTTTAAGACACTTTGG-3'

D) exons 8–9 (SEQ ID NO:34): 5'-AAGTAGGCCTAG GACCTGAGGCACTGGACG-3'

E) exons 6–9 (SEQ ID NO:35): 5'-TAAGTAGGCCTA GGACCTTTAAGACACTTTG-3'

F) exons 8–10 (SEQ ID NO:36): 5'-CAGGTTTAGG ATATCCTGAGGCACTGGACG-3'

G) exon 13 (SEQ ID NO:37): 5'-CCTTCTCAGAGA GAAGTAAATTTTACTTCTCTGTGG-3'

H) exons 12–14 (SEQ ID NO:38): 5'-CCACCATCTGC TTTCCCTTTCTTCTTCCTCC-3'

I) exons 11–14 (SEQ ID NO:39): 5'-CCACCATCTG CTTTCCTATGGCAATAACAATC-3'

FIG. 12 Correlation of CD46 RNA transcripts with protein isoforms. The transcript name indicates exons which have been deleted, 12a indicates the first part of exon 12. Breaks in the solid black lines under "Transcript structure" indicate the deletion of exons corresponding to the diagram of exon structure shown below. Boxes indicate exons and the dashed line through exon 12 shows the position of the cryptic splice acceptor site. Arrow indicate positions of oligonucleotide probes used in FIG. 3 and letters denote the panel in which they were used. The protein $M_r$ and name of the correlating protein isoform are shown; question marks indicate that the protein isoform was not discernible in the western blot of FIG. 1. The tissue distribution of RNA transcripts and protein isoforms is indicated in the right hand column.

FIGS. 13*a*–13*g* A summary of nucleic acid sequence and amino acid allocation for exons 7 to 14 of transcripts a to n of FIG. 12.

FIGS. 16*a*–16*d* depict a cDNA sequence and amino acid sequence for CD46 isoform PM5.8 (SEQ ID NO:45).

FIG. 13-*a* includes SEQ ID NOS 11 and 12; FIG. 13-*b* includes SEQ ID NOS 17 and 18; FIG. 13-*c* includes SEQ ID NOS 19 and 20; FIG. 13-*d* includes SEQ ID NOS 21 and 22; FIG. 13-*e* includes SEQ ID NOS 23, 24 and 25; FIG. 13-*f* includes SEQ ID NOS 26 and 27; and FIG. 13-*g* includes SEQ ID NOS 28, 29 and 30.

FIGS. 14*a*–14*d* depict a cDNA sequence and amino acid sequence for CD46 isoform PM5.3 (SEQ ID NO:41).

FIGS. 15*a*–15*e* depict a cDNA sequence and amino acid sequence for CD46 isoform PM5.6 (SEQ ID NO:43).

DETAILED DESCRIPTION OF PREFERRED EMBODIMENTS

EXAMPLE 1

Isolation of cDNA Clones

Using the sequence of the 23 N-terminal amino acids previously obtained from the 66 and 56 kDa α and β chains of CD46 (Purcell et al. (1989) Immunol. Cell Biol. 67, 279–389), five oligonucleotide probes were synthesized (Table 1) using an Applied Biosystems 380A DNA Synthesizer (Applied Biosystems Inc.). Short oligonucleotides containing either the full component of redundant codons, or longer oligonucleotides selected to have the most likely codon using the algorithm of Lathe et al. (1985) J. Mol. Biol. 183, 1–12, were end-labelled with $\gamma^{32}$ dATP using T4 polynucleotide kinase (Maxam and Gilbert (1977) Methods in Enzymology 65, 499–560) and unincorporated label removed with a Sepharose G-25 spun column.

A human placental cDNA library containing $5\times10^6$ independent clones in the λgt11 vector (Clonetech) was plated at a density of $5\times10^4$p.f.u. per 15 cm plate and plaque DNA transferred in triplicate and covalently linked to nylon membranes (Hybond-N, Amersham; Huynh et al. (1988) DNA Cloning I, A Practical Approach, Glover (Ed), Oxford pp 47–48. Filters were probed with three pools of oligonucleotides in hybridization buffer containing 5×PE (1×PE= 0.133 m phosphate/1 mM EDTA buffer, pH 6.9). 7% SDS, 0.5% BLOTTO (dried skim milk powder), 1 polyethylene glycol 2000 at 42° C. and washed with 2×SSC (0.3M, Nacl, 0.03M Sodium Citrate pH 7.0), 0.1% SDS at 2° C. below the lowest melting temperature of the oligonucleotides in the pool (Reed and Mann, 1985). Clones hybridizing with two or more of the pools were selected for further screening with both pools and individual oligonucleotides. After four rounds of screening, six clones (pm5.1, 0.2, 0.3, 0.6, 0.8 and 0.10), were isolated and phage DNA prepared by the DE52-Sepharose method (Benson and Taylor (1984) Bio Techniques, 2, 126–127). Inserts from cDNA clones were prepared by digesting with EcoRI and isolating insert bands by electrophoresis on an 0.8% agarose gel and subcloning into the pVZ plasmid vector for sequencing and other analyses.

DNA analysis. The nucleotide sequences of the CD46 cDNA clones were determined by the dideoxynucleotide chain termination method using the T4 polymerase, Sequenase II (Tabors and Richardson (1987) Proc. Natl. Acad. Sci. U.S.A., 84, 4767–4777) (United States Biochemical Corporation) from double and single stranded templates of cDNA clone in the pVZ vector. Products were analyzed on denaturing acrylamide gels containing urea. The sequencing strategy included using internal oligonucleotide primers, and using clones containing cDNA inserts truncated by the Mung bean exonuclease III method (Sambrook et al. (1989) Molecular Cloning, A Laboratory Manual (2nd Ed), Cold Spring Harbour Laboratory) to sequence both strands of each clone. Sequences were collated and corrected and sequence searches performed with the aid of a VAX computer using the MELBSYS and DBQUERY suite of programs.

The nucleotide sequences of these clones were mostly identical, having a single open reading frame, however five of the six clones differed at the 3' end of the long open reading frame. Clone pm5.2 had a shorter 3' untranslated region than clone pm5.6 but was otherwise identical.

The complete nucleotide sequence of the pm5.1 clone, which had the longest contiguous coding sequence, is shown in FIGS. 1*a*–1*d* (SEQ ID NO:1). The pm5.1 clone encodes a protein of 377 amino acids from the single long open reading frame, commencing from an initiation codon (ATG) at nucleotide position 33 or at position 102. The amino acid sequence commencing from the Cys at amino acid position 35 is identical to that obtained experimentally from purified CD46 (Purcell et al. (1990) Immunogenetics, 31, 21–28) and the sequence of the first 34 amino acids corresponds with that predicted for a typical leader peptide that is cleaved to generate the mature protein (von Heijne (1986) Nucleic Acids Res., 14, 4683–4690). The molecular weight calculated for the mature protein is 38,353 Da, which correlates well with earlier analyses of deglycosylated CD46 (Purcell et al. (1989) Immunol. Cell Biol., 67, 279–281) and biosynthetically labelled MCP precursor (Ballard et al. (1988) J. Immunol., 141, 3923–3929). There are three potential N-linked glycosylation sites (FIGS. 1*a*–1*d*) and multiple potential O-linked glycosylation sites, many of which exist in a region between amino acids 253 and 280. The addition of carbohydrate at these sites would account for the increased molecular weight of the mature protein. A stretch of 23 hydrophobic amino acids from position 295 to 317 are consistent with a membrane spanning domain (Kyte and Doolittle (1982) J. Mol. Biol., 157, 105–132). The rest of the open reading frame encodes a cytoplasmic tail of 26 mostly charged amino acids. Four regions of approximately 60 amino acids were identified at the $NH_2$-terminal end of the mature protein that have between 18–35% amino acid identity (FIG. 2), and these each contain the consensus of the family of complement regulatory molecules and can therefore be considered as short consensus sequence repeat (SCR) units of this family of molecules (Reid et al. (1986) Immunol. Today, 7, 230–234).

The pm5.3, pm5.6 and pm5.10 clones each have segments of coding sequence deleted at regions 3' to the segment encoding the four SCR units of the prototype pm5.1 clone (FIGS. 1*a*–1*d*). The pm5.10 clone lacks 93 bp of nucleotide sequence that encodes 16 of the 23 amino acids of the cytoplasmic tail and a portion of the 3' untranslated sequence of the pm5.1 clone (FIG. 1, FIGS. 3*a*–3*c*, SEQ ID NOS:4–10). Since this 93 bp fragment contains the termination codon ending the open reading frame of pm5.1, the new reading frame of pm5.10 includes a segment of sequence that forms the initial portion of the 3' untranslated sequence in pm5.1. Therefore, the CD46 molecule encoded by pm5.10 has a cytoplasmic tail of 33 amino acids, 23 of which differ from those encoded by pm5.1 (SEQ ID NO:7) (FIGS. 3*a*–3*d*). This new tail would be longer by 7 amino acids, but would also have a high proportion of charged amino acids. The pm5.10 clone is not full-length and lacks the sequence at the 5' end that would encode the leader peptide (FIGS. 4*a*–4*e*), however the remainder of the nucleotide sequence is identical to pm5.1. The nucleotide sequence of the pm5.10 clone perfectly matches within that of a MCP cDNA clone isolated independently, without a single nucleotide different (Lublin et al. (1988) J. Exp. Med., 168, 181–194).

Figure 3A:
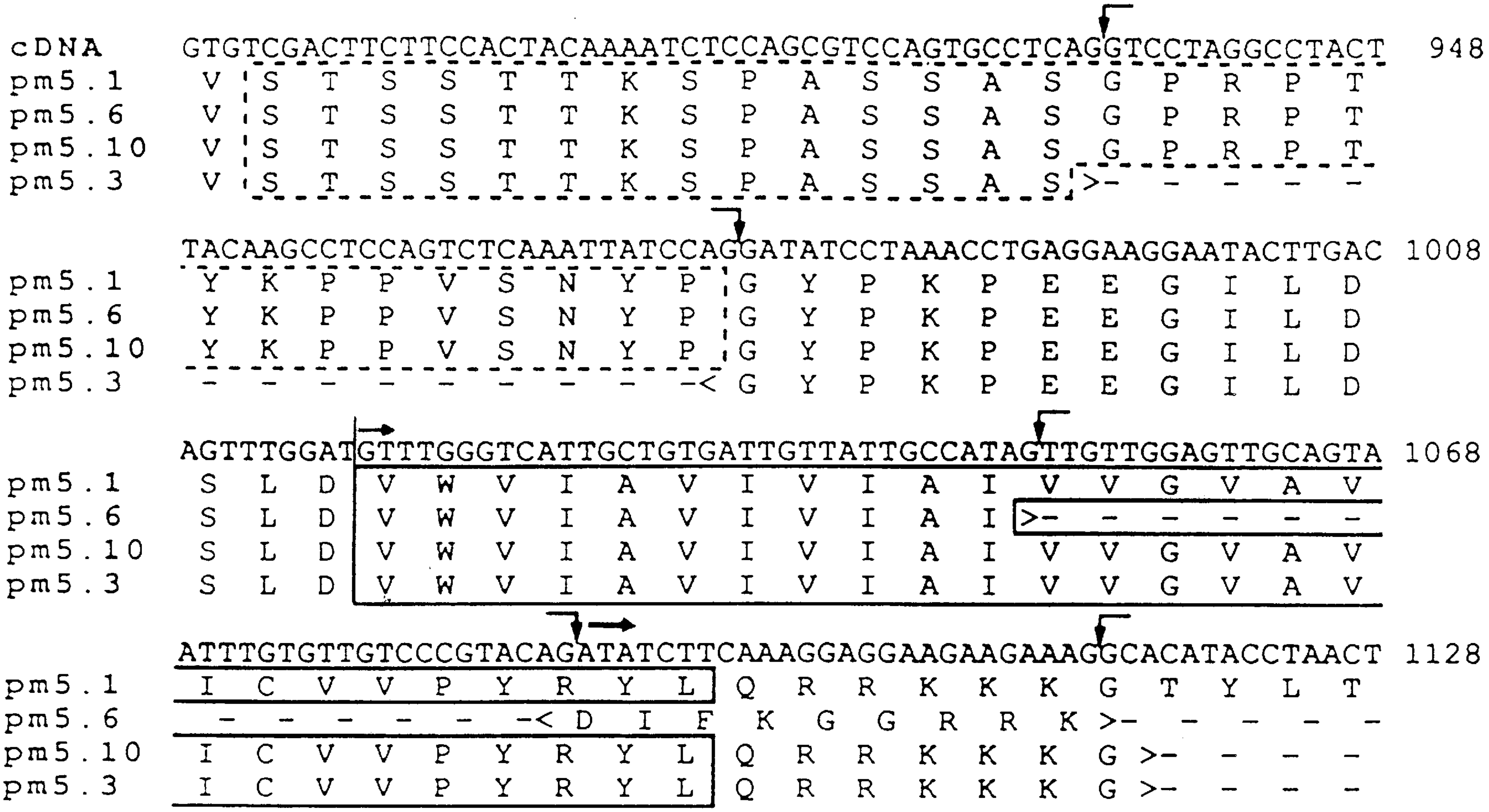
Figures 4A, 4B, 4C, 4D, 4E:
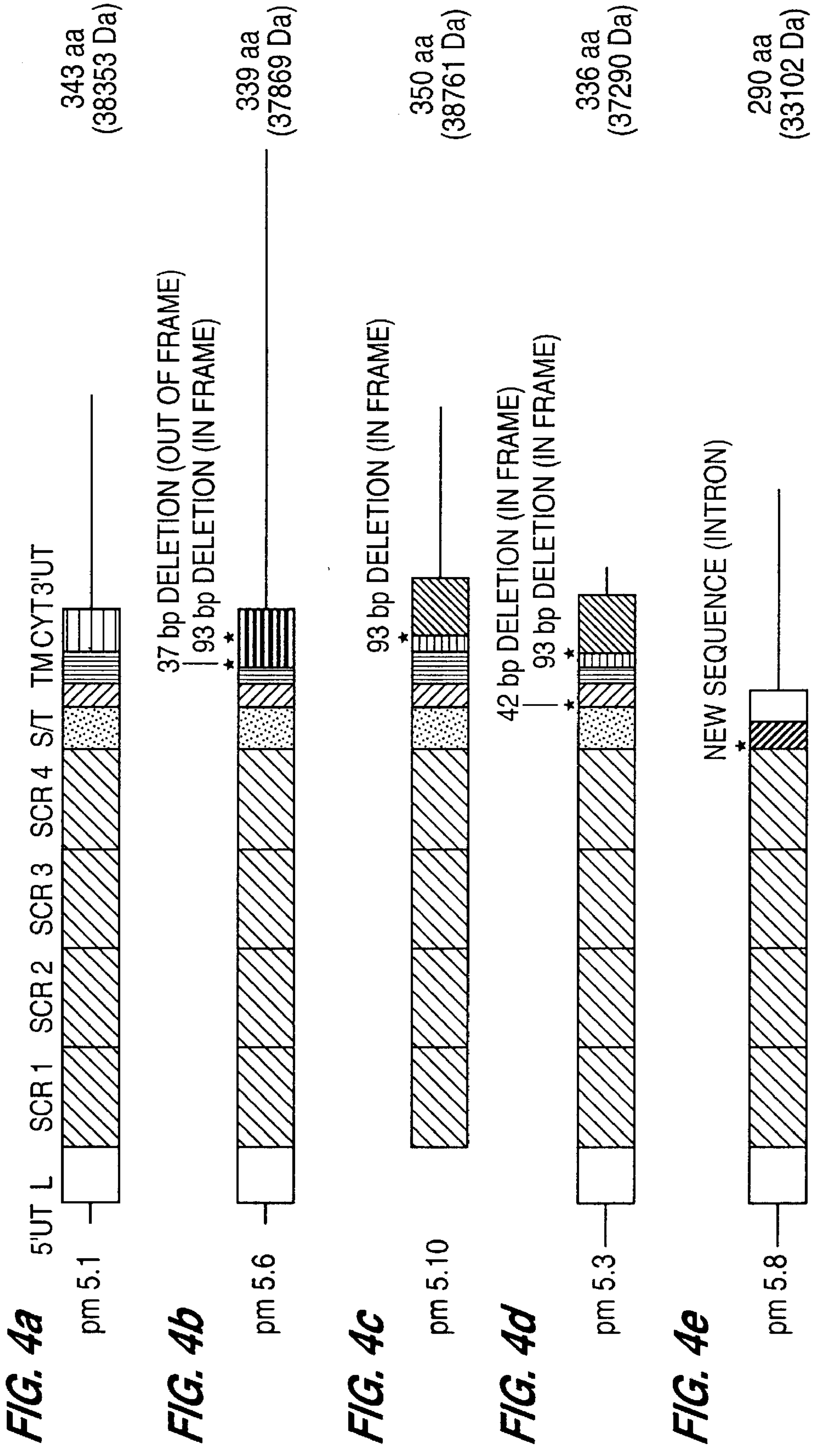
FIGS. 4*a*–4*e* show a summary of the structure of the five alternate cDNA clones for CD46 showing the positions where differences in sequence occur relative to the pm5.1 clone. The location of the 5' untranslated (5' UT), leader peptide (L), short consensus repeat (SCR), serine/threonine rich (S/T), hydrophobic transmembrane (TM), cytoplasmic tail (CYT), and 3' untranslated (3' UT) regions are labelled above the pm5.1 clone. The number of amino acids and calculated molecular weight of each version of CD46 potentially encoded by these is shown at the right.

The pm5.3 clone also lacks the 93 bp fragment absent in pm5.10, but has an additional deletion of 42 bp from a region encoding the second half (14 amino acids) of the Ser/Thr rich region (FIGS. 3*a*–3*c* (SEQ ID NO:8), FIGS. 4*a*–4*e*) removing two potential O-linked carbohydrate addition sites and five kink forming Pro residues. Since loss of this segment of DNA does not change the reading frame the remainder of the CD46 protein encoded by this clone would have the same amino acid sequence as that encoded by pm5.10.

The pm5.6 clone also lacks the 93 bp fragment absent in pm5.10, but has an additional deletion of 37 bp from a region encoding the second half (12 amino acids) of the hydrophobic transmembrane domain resulting from the use of a cryptic splice acceptor sequence (TGTTGTCCCGTACAG, SEQ ID NO:4) at the 3' and of this deleted segment (FIGS. 3*a*–3*c*, FIGS. 4*a*–4*e*). The absence of this fragment changes the reading frame and the CD46 protein encoded by the pm5.6 clone would have 34 different amino acids at the carboxyl-terminus compared to CD46 protein from the other clones. Subsequently, the resulting CD46 molecule (SEQ ID NO:6) would have hydrophilic and predominantly charged amino acids substituting for half of the transmembrane domain, and this may lead to secretion of this version of CD46 from the cell. The pm5.6 clone had a 3' untranslated region that was 465 bp longer than the pm5.1 clone (FIG. 1B). A second independent clone, pm5.2, had the same set of deletions as pm5.6, but was 286 bp shorter than pm5.6 in the 3' untranslated region. Neither a poly(A) signal sequence (AATAAA) nor a poly(A) tail was found in the 3' untranslated sequences of any of the clones.

The sequence of the pm5.8 clone was identical to the pm5.1 clone in the portion encoding the $NH^2$ leader and four SCR regions, however the sequence after nucleotide 890 of pm5.1 was different to any sequence derived from all the other clones, (FIG. 3B) SEQ ID NO:9 and 10) and results from reading through of the cDNA into an intron sequence after the fourth SCR (see below). If protein were encoded by this new sequence it would contain a stretch of 16 hydrophobic amino acids possibly serving as a membrane spanning sequence, although this is a little shorter than typically found (Kyte and Doolittle (1982) J. Mol. Biol., 157, 105–132). The putative cytoplasmic tail of this version of CD46 would also contain a high proportion of charged amino acids. The structure of the proteins derived from the 5 alternative versions of CD46 cDNA clones isolated from the human placental cDNA library are summarized in FIG. 4.

EXAMPLE 2

Northern Blot Analysis of CD46 mRNA

RNA was prepared from fresh human placental tissue using guanidinium isothiocyanate method (Chirgwin et al. (1979) Biochem., 18, 5294–5299) and poly(A)+ RNA isolated by chromatography on oligo (dT) cellulose (Aviv and Leder, (1972) Proc. Natl. Acad. Sci. U.S.A., 69, 1408–1412). RNA was denatured and size fractionated on a 1% agarose gel in the presence of 0.8% formaldehyde and blotted onto nylon membranes using 0.1M NaOH transfer buffer. Filters were prehybridized with 4×PE defined earlier, 50% formamide, 7% SDS, 0.5% BLOTTO (skim milk powder), 1% polyethylene glycol at 42° C. then hybridized with either pm5.1 cDNA insert labelled with 32Pα-ATP by nick transplantation, or with oligonucleotides complimentary to sequence spania the splice site or to or deleted segments of the cDNA clones (Table 2). Oligonucleotides were end-labelled using T4 polynucleotide kinase as before. Filters were washed in 1×SSC at 60° C. for the cDNA probes or 1×SSC at 1° C. below the Tdmin for the oligonucleotides.

Figure 5A:
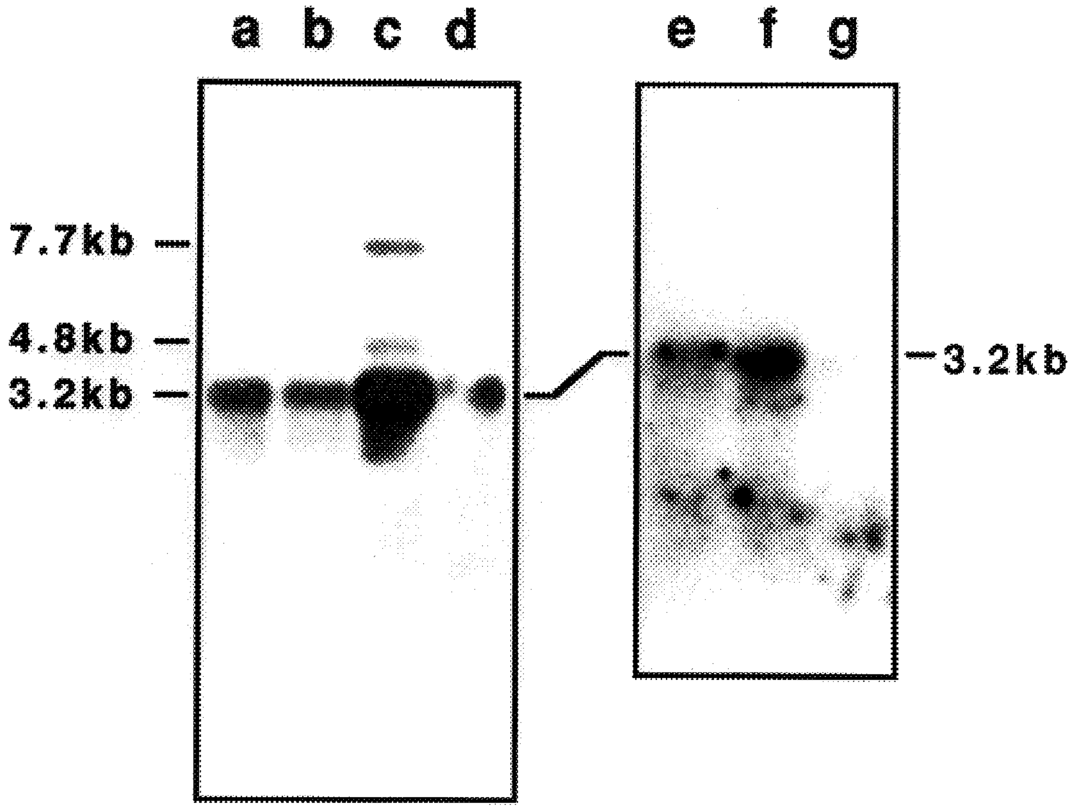
FIGS. 5*a*–5*b* are is a northern blot analysis of 2 $\mu$g of poly$(A)^+$ RNA separated under denaturing conditions by electrophoresis on 1.2% agarose gels containing formaldehyde, transferred to Nylon membrane and hybridized with $^{32}$P-labelled CD46 cDNA from the pm5.1 clone. The autoradiograph shows RNA from human spleen tissue from patients with non-Hodgkins lymphoma (lane a), polycythemia vera (lane b), hairy cell leukaemia (lane c), physical trauma (normal) (lane g) and from the human T-lymphoblastoid cell line PEER (lane c), the myelomonocytic cell line U937 (lane f), and the gibbon ape T-lymphoblastoid cell-line UCD-144-MLA (lane d). Each sample had a predominant band of 3.2 kb and the spleen tissue infiltrated with hairy cell leukaemia cell had two minor bands at 4.8 kb and 7.7 kb.
Figure 5B:
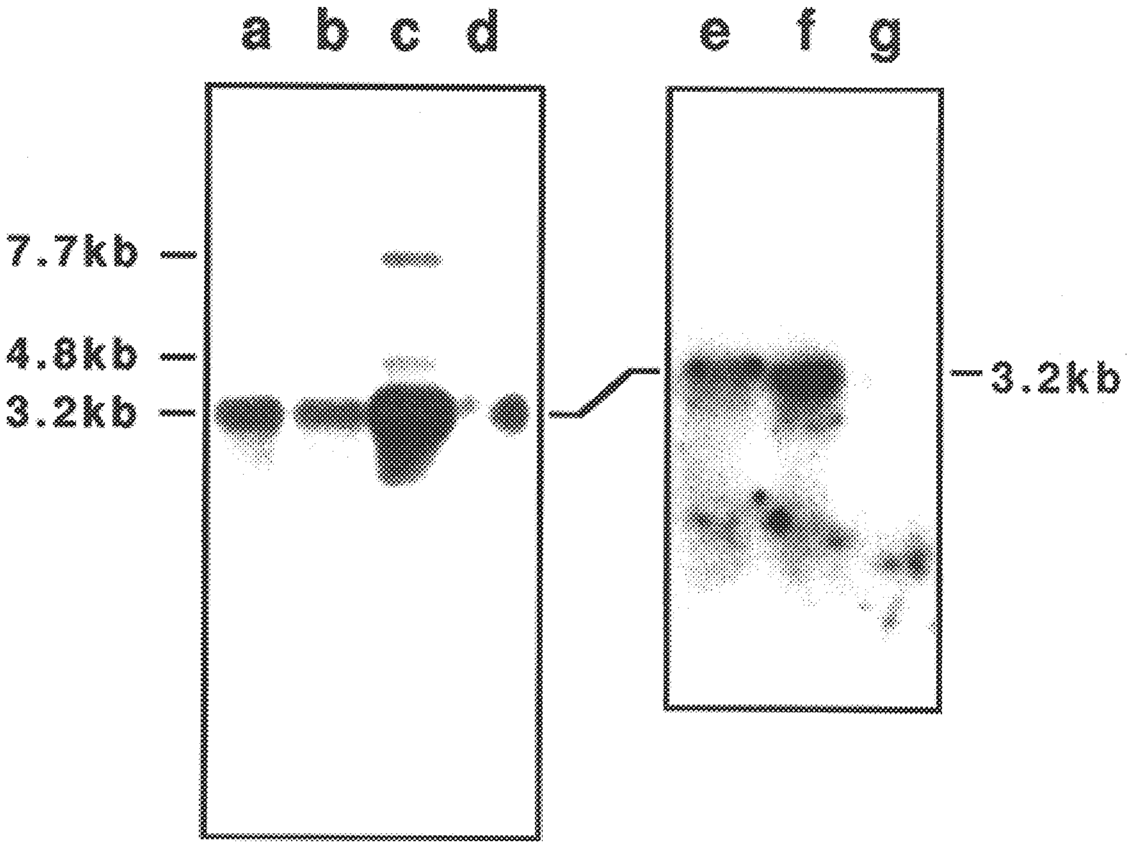
Figure 6:
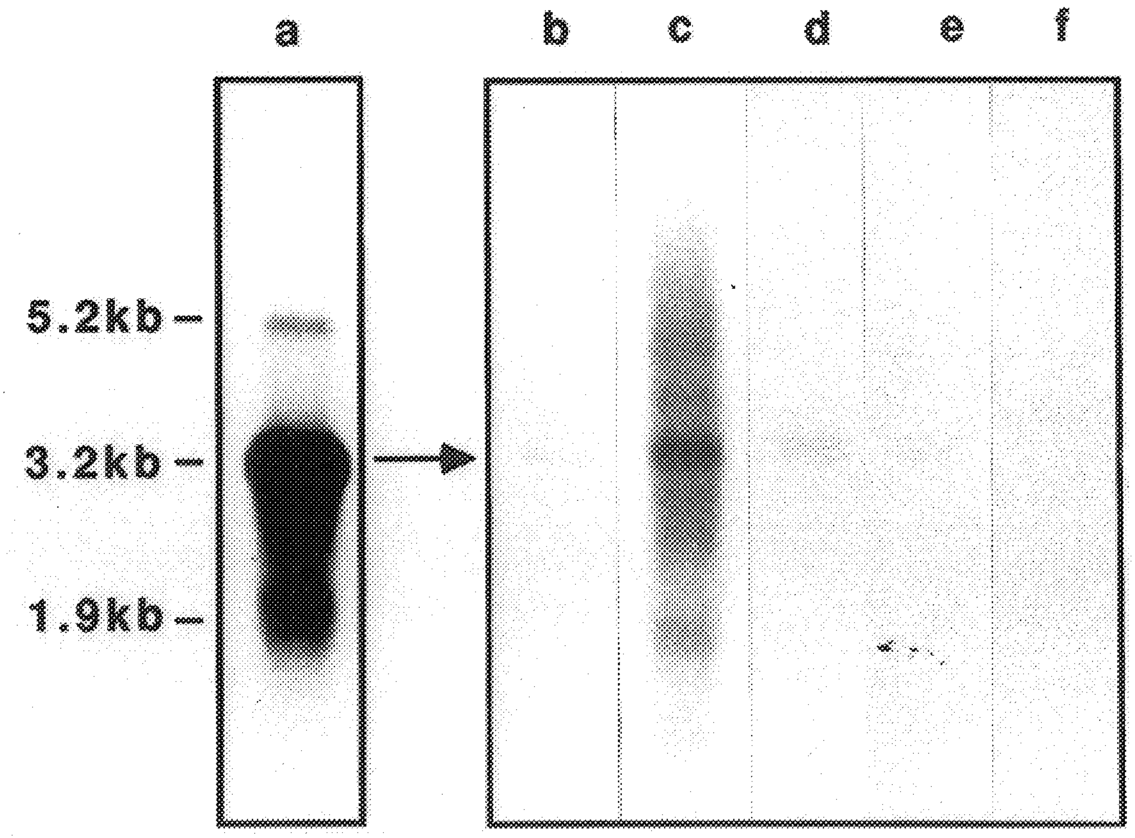
FIG. 6 is a northern blot analysis of 2 $\mu$g of poly$(A)^+$ from human placenta separated under denaturing conditions by electrophoresis on 1.2% agarose gels containing formaldehyde, transferred to strips of Nylon membrane that were hybridized with either $^{32}$P-labelled CD46 cDNA from the pm5.1 clone (lane a), or the oligonucleotides; On63 which spans the site of the 93 bp deleted from the pm5.1 sequence and therefore specific for RNA corresponding to the pm5.3, pm5.6 and pm5.10 clones (lane b), On46 which is within this 93 bp segment of pm5.1 and therefore specific for RNA corresponding to the pm5.1 clone (lane c), On35 which spans the site of the 42 bp segment deleted by the pm5.3 clone and therefore specific for RNA corresponding to the pm5.3 clone (lane d), On44 which is within the 42 bp segment deleted by the pm5.3 clone and therefore specific for RNA corresponding to the pm5.3 clone (lane c), or the On68 which is within the new (intron) sequence of the pm5.8 clone (lane f). Details of these oligonucleotides are shown in Table 2.

The size and number of CD46 mRNA species was determined in samples of spleen from human and gibbonape cell lines (FIGS. 5*a*–5*b*). Each of the samples tested had a dominant band at 3.2 kb and the spleen infiltrated with hairy cell leukaemia (FIG. 5*c*) had two other fainter bands of 4.8 and 7.7 kb. Using densitometric scanning equivalent levels of the 3.2 kb CD46 mRNA were observed in spleen from patients with non-Hodgkins lymphoma and polycythemia vera and in the human cell-lines PEER and U937 and in the gibbon ape cell line 144-MLA. The 144-MLA line is chronically infected with the gibbon ape leukaemia virus which encodes a virion surface glycoprotein (SU70) that bears a cross-reactive antigenic epitope of CD46 recognised by the E4.3 mAb (Purcell et al. (1989) Leukocyte Typing IV White Cell Differentiation Antigens, pp 653–655, Oxford University Press). The E4.3 mAb to CD46 recognised thirty fold more protein at the surface of 144-MLA cells than other human cell lines, however the equivalent levels of CD46 mRNA supports the earlier finding that the E4.3 mAb predominantly reacts with the gibbon ape leukaemia virus surface gp70 molecules on the 144-MLA cell. The spleen sample infiltrated with hairy cell leukaemia showed a ten fold greater level of the 3.2 kb CD46 mRNA than the other spleen samples and the histopathologically normal spleen from a trauma patient had twenty fold less CD46 mRNA than the spleen samples infiltrated by neoplastic cells. This again showed that malignant tissue samples and cell-lines contain ten to twenty fold more CD46 than the corresponding non-malignant cell and shows that this is due to elevated transcription of CD46 RNA. Size variations of around 100 bp in the 3.2 kb band, as predicted from the sequence of the clones, were beyond the resolution capability of these gels. To verify the existence of, and examine the relative proportion of, the alternatively spliced CD46 RNA species predicted from the clones, a series of antisense oligonucleotides were constructed that would differentially hybridize with alternately spliced CD46 mRNA (Table 2). These were used to probe Northern blots of poly(A)$^+$ RNA from human placenta (FIG. 6). When a CD46 cDNA insert from the pm5.1 clone was used as a probe three bands were noted, a broad band at 3.2 kb as with the other human cells, a band of 1.9 kb and a fainter band of 5.2 kb. The 1.9 kb band probably relates to the use of cryptic polyadenylation signals (AATATA or AATGAA) found at positions 1579 and 1592 of the pm5.1 clone. These sequences were apparently used by the clone of MCP isolated by Lublin et al. (1988) J. Exp. Med., 168, 181–194. Hybridization with the On63 oligonucleotide, specific for RNA lacking the 93 bp segment of the pm5.1 clone between positions 1115 and 1208 (i.e., corresponding to the pm5.3, pm5.6 and pm5.10 clones), yielded a faint band of 3.2 kb (arrowed in FIG. 6, lane D) showing that RNA lacking the 93 bp segments is a genuine component of the pool of CD46 mRNA. Hybridization with the On46 oligonucleotide, specific for RNA containing the 93 bp segment (pm5.1) yielded a predominant 3.2 kb CD46 band (FIG. 6, lane c). Hybridization with the On35 oligonucleotide, which is specific for RNA containing pm5.3 type of deletion of 42 bp, also yielded the 3.2 kb CD46 RNA band verifying that a subpool of CD46 RNA contains this deletion (FIG. 6, lane d). Hybridization of the On44 oligonucleotide, which is specific for RNA retaining the 42 bp deletion yielded a very faint 3.2 kb CD46 RNA band showing that a subpool of CD46 RNA retains this deleted segment (FIG. 6, lane e). Hybridization with the On68 oligonucleotide, which is specific for the new (intron) sequence of the pm5.8 clone, did not result in the detection of any RNA bands (FIG. 6, lane f). The results show that the pm5.1, pm5.3, pm5.6 and pm5.10 cDNA clones of CD46 isolated from the placental cDNA library result from the presence of corresponding alternative RNA species for CD46 and are not a result of rearrangements during the construction of the library or other manipulations.

EXAMPLE 3

Analysis of CD46 mRNA by Polymerase Chain Reaction (PCR)

Placental poly(A)$^+$ RNA and total RNA was treated with RNase-free DNase and used as a template for the synthesis of cDNA with 100 U Molony murine leukemia virus reverse transcriptase. Reactions of 5 $\mu$g poly(A)$^+$ RNA or 50 $\mu$g total RNA; 12.5 $\mu$M (each) dNTPs, 0.25 $\mu$M On24, and oligo (dT) 16–20 mer or random hexamers as primers were incubated at 37° C. for 1 hour, then DNA was amplified by Polymerase Chain Reaction (PCR) in 0.5 mM $MgCl_2$, 10 mM Tris HCl (pH 8.3), 50 mM KCl, 200 mM (each) dNTPs, 4UTaq DNA polymerase (Amersham). Pairs of oligonucleotides were added to a final concentration of 1 $\mu$M and template was added at 2 $\mu$l, 1 $\mu$g, or 1 ng per 50 $\mu$l reaction for first strand cDNA, genomic DNA and cDNA clones respectively. To label the product the dCTP concentration was reduced to 100 mM and 0.5 $\mu$l $\alpha^{32}$P-dCTP was added. After 3 min. at 95° C. reactions were subjected to 30 cycles of denaturation (93° C., 1 min.) annealing (see Table 2, 2 min.), and elongation, (72° C., 1 min). Unlabelled PCR products were size fractionated on a 1.5% agarose gel transferred to Hybond N$^+$ in 0.5M NaOH, 1.5M NaCl for probing with oligonucleotides.

Radiolabelled PCR samples were analyzed by electrophoresis on 6% acrylamide gels containing urea with sequencing reactions as size markers and autoradiographed at −70° C. on XAR-5 or XRP film.

Figure 7A:
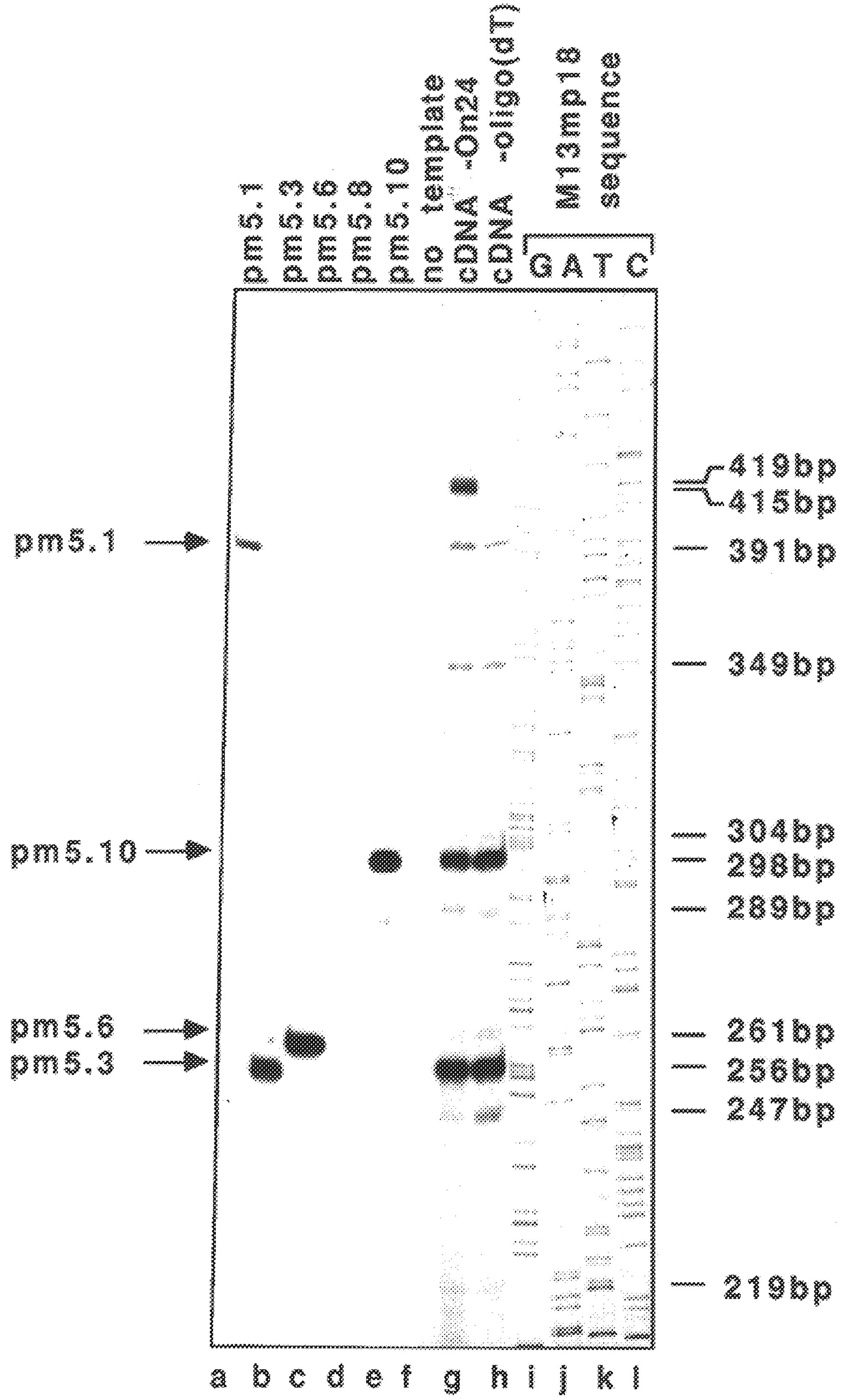
FIGS. 7*a*–7*g* Expression of CD46 transcripts in human placenta. The variable region of CD46 was amplified by PCR using primers On37 and On24. Templates for the PCR reaction were the clones pm5.1, pm5.3, pm5.6, pm5.8 and pm5.10 (lanes a to e respectively), no template (lane f), and cDNA produced from placental poly $(A)^+$ cytoplasmic RNA primed with On24 (lane g) and oligo(dT) (lane h). $^{32}$P-labelled samples were electrophoresed on a 6% acrylamide gel containing urea with the M13mp18 sequence ladder as a size marker. Sizes of the PCR products are indicated on the right and the position of the PCR products corresponding to the clones are arrowed on the left. Unlabelled products were electrophoresed on a 1.5% agarose gel (Panel 1), transferred onto nylon and probed with oligonucleotides specific for different CD46 transcripts (Panels 2 to 6). Details of the oligonucleotides are shown in Table 2.
Figure 7B:
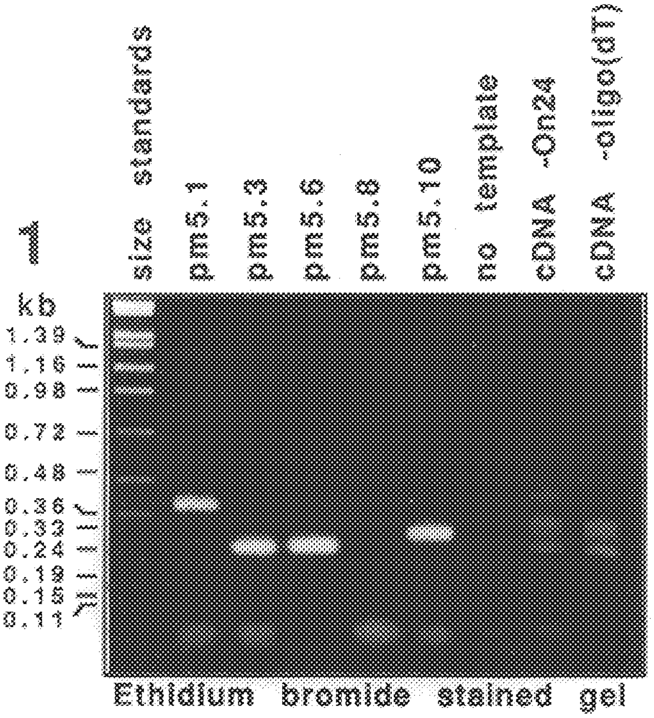
Figure 7D:
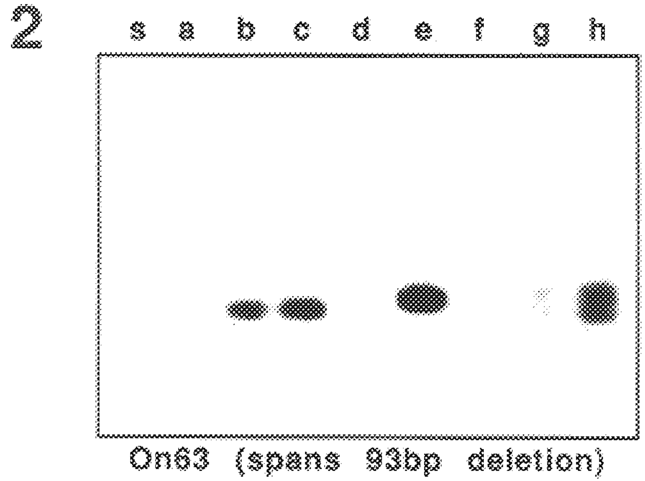
Figure 7F:
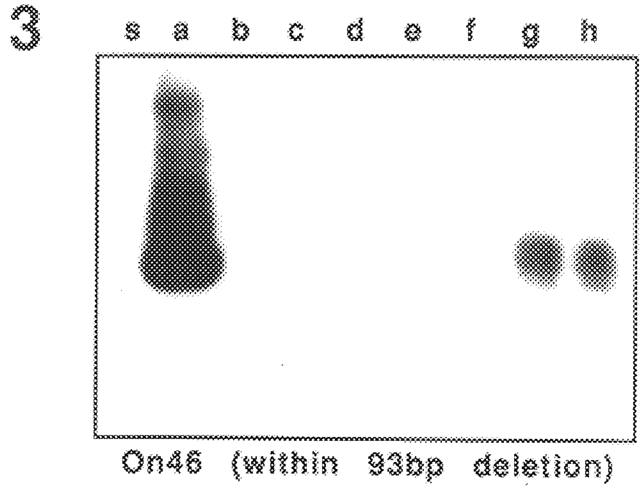
Figure 7C:
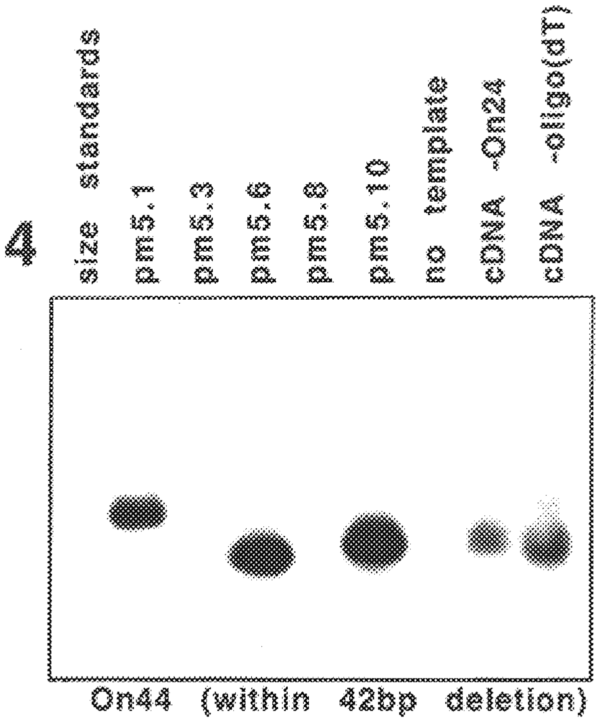
Figure 7E:
Figure 7G:
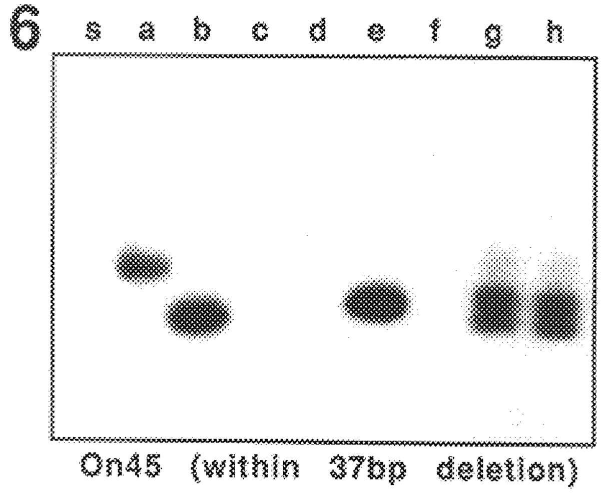

To overcome the weak hybridization signals obtained in Northern blots using the type specific oligonucleotide probes, placental poly(A)+ cytoplasmic RNA was converted to cDNA with reverse transcriptase by priming with On24 or with oligo(dT) and alternate cDNAs for CD46 amplified by polymerase chain reaction (PCR) using CD46 primers On57 and On24 that hybridize outside the region of alternative splicing. Electrophoresis of labelled amplification products from the different CD46 clones and from placental cDNA on 6% acrylamide gels revealed a number of different sized bands (FIG. 7A), including bands corresponding in size to those amplified from the pm5.1, pm5.3, pm5.6 and pm5.10 clones on (391, 256, 261 and 298 bp respectively). Several additional bands (219, 247, 289, 304 and 349 bp) were observed from placental cDNA samples primed with both On24 and oligo(dT). While several of these extra bands differ from the 391 bp pm5.1—type band by sizes that may correspond to the deletion of different sets of the 37, 42 and 93 bp segments (eg. 349=391-42, or 219=391-37-42-93) or of the 27 and 75 bp segments between the 42, 37 and 93 bp regions (eg. 289=391-75-27, or 249=391-42-75-27) the structure of these and their significance requires further investigation. A doublet of 415 and 419 bp which is larger than the PCR products from any of the clones was also produced from cDNA primed with On24 but not with oligo(dT). The RNA molecules giving rise to these bands either lack a poly(A) tail or exist in the 5.2 kb poly (A)+RNA pool which would be reverse transcribed to the region of alternative splicing at low efficiency and may not be functionally important. None of the bands in the cDNA samples arose due to amplification of contaminating clones or genomic DNA because no bands were obtained after PCR from various controls including reaction mixes lacking template DNA, cDNA reaction mixes lacking reverse transcriptase (hence containing only RNA), an aliquot of reverse transcriptase enzyme mix used in cDNA synthesis and genomic DNA. To confirm the identity of the different bands amplified from cDNA, unlabelled PCR products were transferred to nylon filters after agarose gel electrophoresis and probed with the type—specific oligonucleotides (FIGS. 7*b*–7*g*). Probing with On63 for the 93 bp deletion of pm5.3, pm5.6 and pm5.10 (FIG. 7*d*) revealed a smear of bands from the position of the pm5.10 band to below the pm5.3 and pm5.6 bands. Probing within the 93 bp sequence with On46 showed a smear of several bands around the size of the pm5.1 band (FIG. 7*f*). Probing with On44 for the 42 bp sequence deleted in pm5.3 (FIG. 7*c*) detected several bands corresponding in size to the bands from the pm5.1, pm5.6 and pm5.10 clones. The On35 probe spanning the 42 bp deletion (FIG. 7*e*) also detected several bands including one of similar size to the pm5.3 band. The On45 probe which lies within the 37 bp deletion (FIG. 7*g*) detected several bands corresponding to pm5.1, pm5.3 and pm5.10. Each of these oligonucleotide probes confirmed the existence of RNA molecules in placenta that have the deletions identified in the CD46 cDNA clones however these probes detected with more PCR products amplified from cDNA than accounted for by amplification from the clones. This shows that several of the extra bands seen in FIG. 7A result from different combinations of the deleted segments contained in the clones.

Figure 8A:
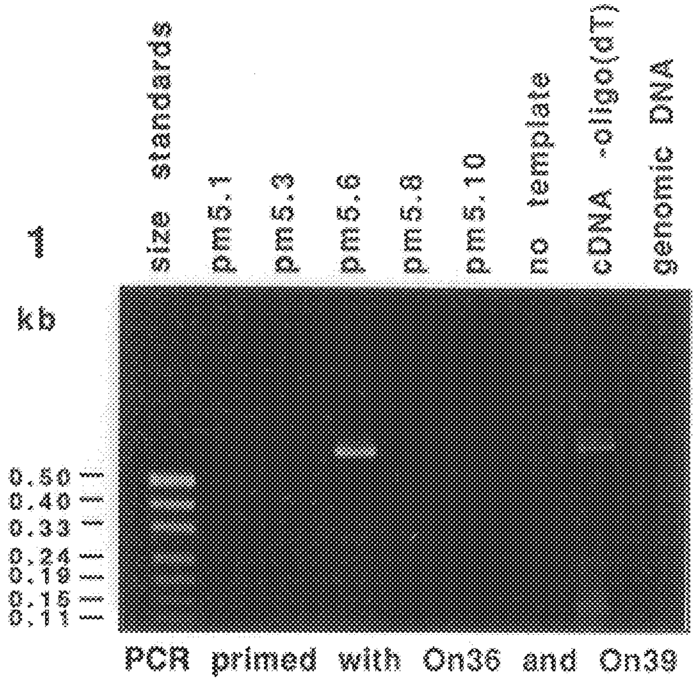
FIGS. 8*a*–8*b* Expression of pm5.6 and pm5.8 type transcripts in human placenta. The five clones (lanes a–e), placental cDNA from cytoplasmic RNA primed with oligo (dT) (1 lane g) or random hexamers (2 lane g) and placental genomic DNA (lanes h) were amplified with paris of primers including: (1) an oligonucleotide spanning the pm5.6 deletion (On36 and On39), or (2) on oligonucleotide in the new sequence of pm5.8 (On83 and On85), and electrophoresed on 1.5% agarose gels with Hpa 11 digested PUC19 DNA as a size marker (lanes s). Reaction mixes containing no template DNA were included as a control.
Figure 8B:
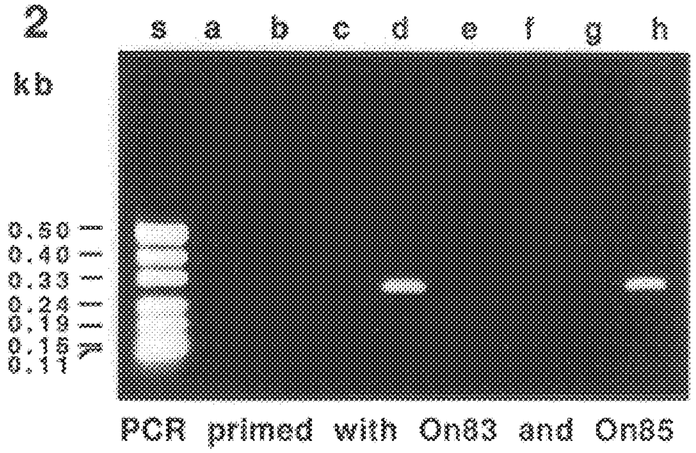

Because the On36 oligonucleotide which spans the site of the 37 bp deletion failed to discriminate pm5.6 from the other CD46 clones when used as a probe in hybridization studies, we used On35 as a primer to amplify placental cDNA prepared with oligo(dT) priming by PCR (FIG. 8*a*). A product of 756 bp was amplified from the pm5.6 clone and from placental cDNA but not from controls. Two larger bands of unknown identity were also obtained from the PCR with placental cDNA. These results show that the 37 bp deletion of the pm5.6 and pm5.2 clones is due to RNA with this structure and not due to cloning artifact. Further, PCR amplification reactions were performed on cDNA from cytoplasmic RNA and genomic DNA using primers at either side of the boundaries of the deleted segments and the regions separating these to locate the intron/exon junctions (Table 3). After PCR across their boundaries, the 42 and 93 bp deleted segments, and the 45 bp region between the site of the pm5.8 alteration and before the 42 bp deletion of pm5.3, were each found to be separate exons yielding larger or no bands with genomic DNA template compared with cDNA template. Introns were located within the 75 bp region between the 42 and 37 bp deletions and the 5' boundary of the 37 bp deletion site. By contrast, no intron was identified at the 3' boundary of the 37 bp deletion, but rather at the boundary of the adjacent 27 bp region and the 93 bp segment. This suggests that the 37 and 27 bp regions are combined to form a single exon. The existence of an intron at the position where the pm5.8 sequence differs from the other clones and the presence of a consensus splice donor sequence (AAGGTACAA) at the site of sequence divergence led us to examine if this clone resulted from the failure to splice this intron. Genomic DNA from placenta and cDNA made by priming poly (A)+ cytoplasmic RNA with random hexamers were used as template in PCR using On85 and On83 to amplify across the region of sequence difference (FIG. 8*b*). A band of 300 bp was produced from the pm5.8 control and from genomic DNA, but not from cDNA or other controls, showing the different sequence in pm5.8 is due to the failure of removal of this intron.

The technique of PCR has been applied to examine the alternative RNAs from different tissues using On85 prepared to a unique stretch of nucleotide sequence in the fourth SCR (Table 2) and On24 in the 3' intranslated region beyond the alternatively spliced region. These were used in PCR using single stranded cDNA template reverse transcribed from RNA from many cell types including several placenta, peripheral blood leukocytes, leukaemia cells from patients with several different malignancies, spleen from trauma, leukaemia and lymphoma patients and cell lines derived from lymphoid and solid tumours. This analysis has shown several interesting points; i) the serine/threonine rich region of CD46 is composed of three separate exons, the third of these was deleted from the pm5.3 clone of the CD46 the second is the 45 bp region between the sites of the pm5.3 and pm5.8 deletions and the first is another 45 bp segment that is not represented in any of our placental cDNA clones; ii) the first of the three Ser/Thr region exons is rarely included in spliced RNA in placenta; iii) the third Ser/Thr region exon is rarely included in spliced RNA from several cell-lines, but is commonly spliced from RNA from placentae; iv) the second Ser/Thr region exon is alternatively spliced in the RNA of most tissues examined to date; v) one 93 bp exon containing an inframe termination condon is alternately spliced to yield two different cytoplasmic tails corresponding to the two cytoplasmic tails found in our pm5.1 and pm5.10 clones, all cell types examined to date have alternately spliced this exon in the pool of RNAs encoding several CD46 isotypes; vi) a third type of cytoplasmic tail used in the pm5.6 clone arises is some cell types due to the use of a cryptic splice acceptor sequence within the second of two exons encoding the transmembrance domain, generating a potentially secreted from of CD46. The PCR technique has been useful in mapping the intron/exon boundaries and identifying that different spliced RNA species exist in different cell types, however most CD46 RNA splice variants are common to all cell types.

Synthetic peptides corresponding to the alternative carboxyl-terminal sequences were used to generate antiserum specific for CD46 isoforms. These CD46 isotype-specific antisera were used in conjunction with our E4.3 monodonal antibody which reacts with all isotypes of CD46 in an enzyme linked immunosorbant assay that specifically detects CD46 variants containing the alternative fragments of nucleic acid identified in the alternative cDNA clones (pm5.1, 5.3, 5.6 and 5.8).

As will be apparent from the foregoing, the presence of spliced RNAs encoding CD46 was totally unexpected.

The above described Examples and conclusions were consolidated to characterize the molecular events leading to the isoform heterogeneity and polymorphic expression of CD46. In particular CD46 and RNA from different tissues was examined. Fourteen alternatively spliced RNA transcripts (several of which correspond to pm.5 series clones described above) were found to be differently expressed, explaining the heterogenous nature of CD46 in tissue.

In the following Examples materials and methods are as follows:

Tissues. Heparinized blood from healthy donors or leukemic patients with chronic or acute leukemia was fractionated by centrifugation through Ficoll-Paque (Pharmacia, Uppsala, Sweden) or Mono-Poly Resolving Medium (ICN, Irvine, Calif.) according to manufacturers instructions, to obtain lymphocytes and granulocytes. The EBV-transformed B cell line was produced in the Research Center for Cancer and Transplantation, The University of Melbourne. Full term placentae, a resected colon tumor and adjacent normal colon were separately homogenized for RNA extraction or teased into single cell suspensions for protein extraction. Semen samples obtained from healthy volunteers were used unfractionated for RNA extraction; spermatozoa were isolated from protein analysis by liquefying for 30 min at room temperature, centrifuging for 10 min at 700 g and washing (×4) with phosphate buffered saline.

Western blot. Cell lysates were prepared at $5\times10^7$ cells/ml (or $5\times\mathbf{10}^8$ spermatozoa/ml) in 0.5% Nonidet-P40 in 10 mM Tris, 0.15 NaCl, pH 7.4 containing 1 mM EDTA and 1 mM phenylmethylsulfonyl fluoride. Cell lysates were acid/base dissociated by the techniques of Swack et al. (1987) Biotechniques, 5, 564–571 and 30 $\mu$g aliquots of protein (measured using the Biorad protein assay) were separated by SDS-PAGE under non-reducing conditions (see Laemmli (1970) Nature 227, 680–685). Proteins were electroblotted onto Immobilon P membrane (Millipore, Bedford, Mass.) and the remaining protein-binding sites were blocked with 2% casein. The CD46 isoforms were detected by the anti-CD46 monoclonal antibody, E4.3 described in Sparrow et al. (1983) Hum. Immunol. 7, 1–15, followed by incubation with horseradish peroxidase-conjugated anti-mouse IgG reagent (Dakopatts, Denmark) and visualisation with a cobalt-enhanced diaminobenzidine substrate.

cDNA synthesis and PCR amplification. Total RNA was prepared using the guanidinium isothiocyanate method (Chirgwin et al. (1979) Biochem. 18, 5294–5299). First strand cDNA was synthesized from 10 μg RNA in 25 μl using 200 U Murine Leukemia Virus reverse transcriptase (BRL, Gaithersburg, Md.), 0.25 mM dATP, dGTP, dTTP, dCTP (each) and 0.5 μg random hexamer oligonucleotides. PCR amplification was performed with 1 U 'Replinase' (NEN, Boston, Mass.), 5 μl first strand cDNA, 0.2 mM dATP, dGTP, dTTP, dCTP (each) and 1 μM each of primers P1 and P2 in 50 mM Tris-HCl (pH9.0), 20 mM $(NH_4)_2SO_4$, 1.5 mM $MgCl_2$, with or without 2.5 μCi α[$^{32}$P]dCTP. After 2 min at 95° C., 1 min), annealing (57° C., 2 min), and elongation (72° C., 2 min). Stringent precautions were taken to avoid cross-contamination between the RNA and cDNA samples, including their preparation in a laboratory in which CD46 clones and PCR products were never handled. Controls, including no cDNA and individual cDNA clones are templates, were included in each PCR to confirm that cross-contamination did not occur.

Analysis of PCR products. The amplified PCR product was extracted with chloroform, and 5 μl aliquots (5% of total product) were electrophoresed on 6% denaturing polyacrylamide gels and autoradiographed. For nucleotide sequencing, bands were excised and eluted in 0.5M $NH_4OAc$, 10 mM MgOAc, 1 mM EDTA, 0.1% SDS for 16 hrs at 4° C., then precipitated with ethanol. 25% of each sample was reamplified with the same primers, extracted with chloroform and purified using Elutip-d columns (Schleicher and Schuell, Dassel, Germany). The sample was denatured with 0.2M NaOH, neutralised, precipitated with ethanol and sequenced using [$^{32}$P]-labelled primers and T7 DNA polymerase (Amersham, Poole, UK). To assess the expression of each splice variant in different tissues, cDNA was amplified in the absence of α[$^{32}$P]dCTP and electrophoresed on 6% denaturing polyacrylamide gels, electroblotted onto nylon membranes in 45 mM Tris-borate, 2 mM EDTA, fixed with 0.25M NaOH, 1.5M NaCl, and probed with oligonucleotides specific for alternatively spliced exons or groups of exons (see FIG. 12 for location of exons).

EXAMPLE 4

Tissue Specific Expression of CD46 Protein Isoforms

Western blot analysis of the different $M_r$ forms of CD46 protein in 16 tissues demonstrated several important features of CD46 protein heterogeneity (FIG. 9). 1) A 76 kDa isoform (termed γ) was observed in EBV-transformed B cells (lane 5) and two of the three leukemic samples (lanes 8, 10). 2) Lymphocytes from healthy donors and cells from leukemic patients contained CD46 isoforms that resolves into two major clusters of bands at 66 and 56 kDa (termed α and β respectively, previously called upper and lower), whose relative abundance varied according to an autosomal codominant polymorphism (9). The three phenotypes are: α-predominant (lanes 1 and 8); α and β in equal proportions (lanes 2 and 9); and β-predominant (lanes 3 and 10). 3) Some placentae expressed an isoform of 63 kDa (termed ξ, lanes 14–16), not seen in the other tissues, in addition to the α and β isoforms (lanes 13–16). 4) Spermatozoa expressed a unique 35 kDa form of CD46 (termed δ, lanes 6 and 7) not found in the other tissues examined, they did not express the α and β isoforms. It was also noted that granulocytes showed isoforms up to 78 kDa (termed ζ) together with the typical α and β isoforms (lane 4). Both normal colon and colon carcinoma tissue from a single donor expressed predominantly α CD46 isoforms with no difference between malignant and normal tissue (lanes 11 and 12). Thus, there are two types of polymorphism apparent here: a) allelic differences in the proportions of α and β isoforms; and b) tissue differences in expression of the α, β, γ, δ, ξ and ζ isoforms.

EXAMPLE 5

Structure of CD46 RNA Transcripts

To investigate alternative splicing of CD46 mRNA, we first identified all alternatively spliced RNAs from the tissues described above, a number of placentae and lymphocyte samples, and from hemopoietic cell lines. RNA from these tissues was converted to cDNA and amplified, and all new splice variants identified were sequenced. No alternative splicing of RNA in the SCR region was observed (data not shown), thus excluding exon 1–6 (FIGS. 9, 12) from contributing to protein heterogeneity. Amplification and sequencing between the fourth SCR and the 3' untranslated region (primers P1 and P2, FIG. 10A), however, identified 14 differently spliced RNAs. Sequencing indicated that most transcripts were derived from the alternative splicing of exons 8, 9, 12 and 13 shown in FIG. 10B, FIG. 12, but other RNAs contained new sequence immediately downstream of the SCR region (FIG. 10C, SEQ ID NOS:11 and 12). This sequence was designated exon 7 (STP A) because of its position in CD46 mRNA and its derived amino acid sequence, and completes the description of the exons identified in genomic clones for CD46. The nucleotide sequence of exon 7 was homologous to the sequence of the two other STP-encoding exons, as there was 69% identity with exon 8, (SEQ ID NO:17), and 62% identity with exon 9. The splicing of exons 7, 8 and 9 (SEQ ID NO:19) did not change the reading frame but effected the number of potential O-glycosylation sites as this region is rich in Ser and Thr residues. Exon 10 is of unknown UK significance and its boundary with exon 11 not yet comprehensively delimited. Exon 13 encoded a cytoplasmic tail (FIG. 10, D3, SEQ ID NO:15) or all (FIG. 10, D4, SEQ ID NO:16) of exon 12 changed the reading frame, giving rise to a third cytoplasmic tail and removing part of the transmembrane region. Thus, alternative splicing of five exons (7, 8, 9, 12 and 13) results in CD46 RNAs encoding protein isoforms with three different cytoplasmic tails and with differences in the length of both the hydrophobic transmembrane region and the STP-rich region of the glycoprotein.

EXAMPLE 6

Tissue Distribution of Alternatively Spliced CD46 RNAs

Figure 9:
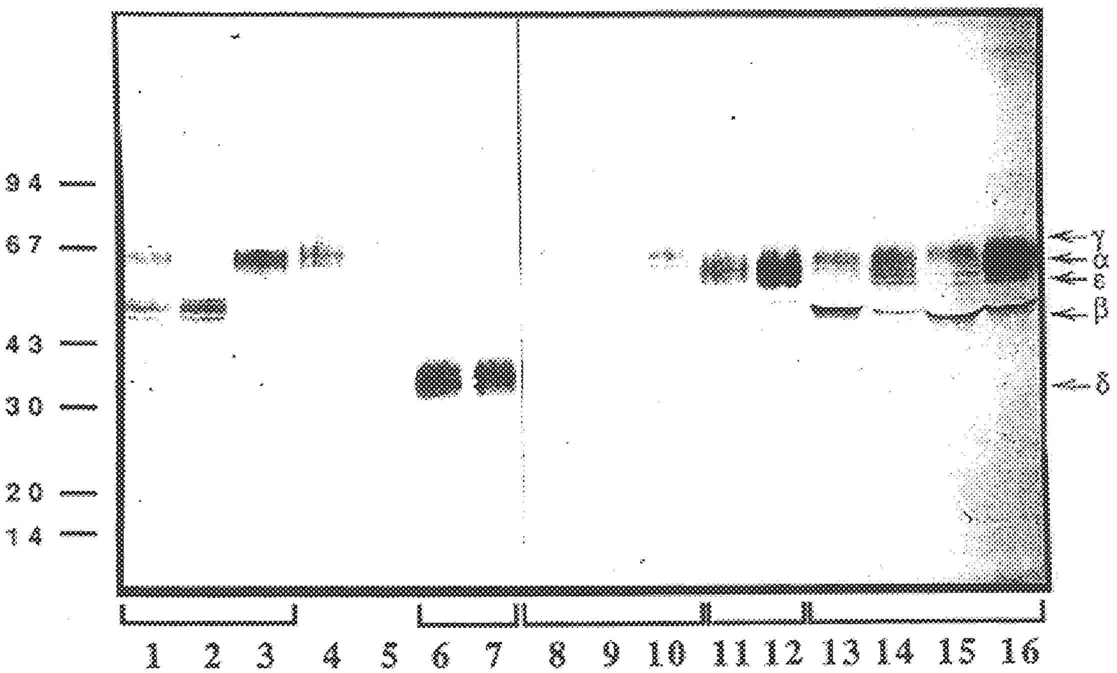
FIG. 9 Distribution of CD46 isoforms in various tissues. Western blot probed with E4.3 showing distribution of CD46 isoforms in lymphocytes (lanes 1–3), granulocytes (lane 4) and EBV-transformed B cells (lane 5), spermatozoa (lanes 6 and 7), leukemic cells (lanes 8–10), normal and malignant colon tissue from a patient with colon carcinoma (lanes 11 and 12 respectively), and full term placentae (lanes 13–16). Samples in lanes 3–6 are from the same donor as are samples in lanes 1 and 7. Relative molecular mass in kDa is shown at left and Greek letters at right indicate positions of isoforms.
Figure 10:
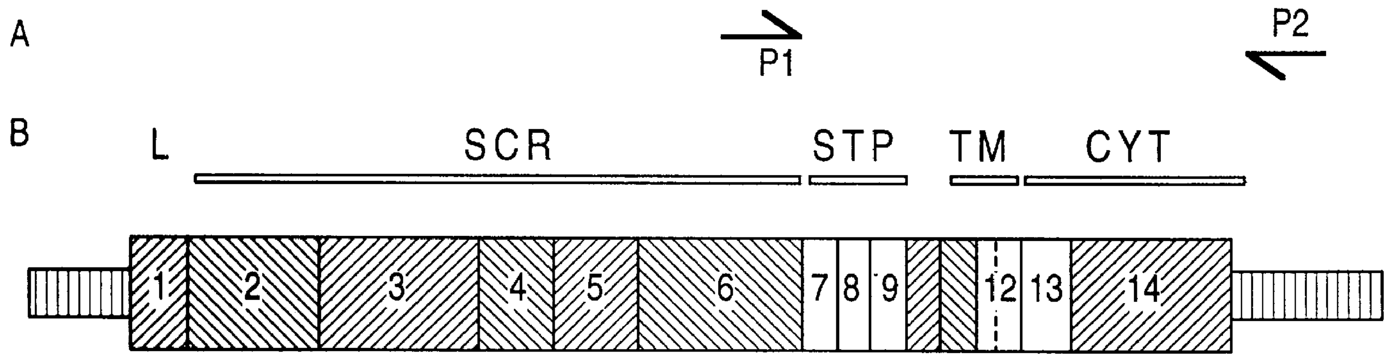
FIG. 10A Position of primers used to amplify the region of alternative splicing. Sequence of P1:-5'-GGCAGCGACACAATTGTC-3' (SEQ ID NO:31) and P2:-5'-CAGCCTCTCTGCTCTGCTG-3' (SEQ ID NO:32).
FIG. 10B Exon organization of the CD46 gene; exons numbers are shown in boxes and functional domains of the derived amino acid sequence is shown above. Shaded boxes indicate constitutively spliced exons and white boxes indicate exons which are alternatively spliced. Dashed line indicates cryptic splice acceptor site.
FIG. 10C Nucleotide and derived amino acid sequence of exon 7 (SEQ ID NOS:11 and 12 respectively).
FIG. 10D Derived amino acid sequence of the COOH-terminal region of the CD46 isoforms (SEQ ID NOS:13–16) encoded by the differential splicing of exons 12 and 13. Spaces in amino acid sequence indicate deletions of the exons shown above and * indicates stop codons.

To determine the relative expression of the 14 RNA transcripts in different tissues, RNA from each tissue examined in FIG. 9 was converted to cDNA and amplified by PCR using primers P1 and P2 (SEQ ID NOS:31 and 32, respectively), spanning the alternatively spliced region. Amplification of CD46 cDNA clones (FIG. 11A) and multiple analysis of RNA samples showed that, although amplification did not allow the estimation of the total amount of CD46 in the sample, it is provided an accurate and reproducible estimation of the relative proportions of the different CD46 RNA variants. We note that no additional splice patterns were produced by this procedure, indicating that homologous recombination during amplification did not occur in these experiments. When α[$^{32}$P]dCTP was incorporated into the PCR products, the 14 transcripts migrated as only 6 bands after electrophoresis (FIG. 11B) due to the similar size of some of the exons. To identify the distribution of each transcript, unlabelled PCR products were electrophoresed, transferred onto nylon filters and probed with oligonucleotides specific for each splice variant (see FIG. 12 for location of probes). Fifteen oligonucleotides were used to determine the distribution of the 14 RNAs (representative gels in FIGS. 11C–I).

Figures 11A, 11B, 11C, 11D, 11E, 11F, 11G, 11H, 11I:
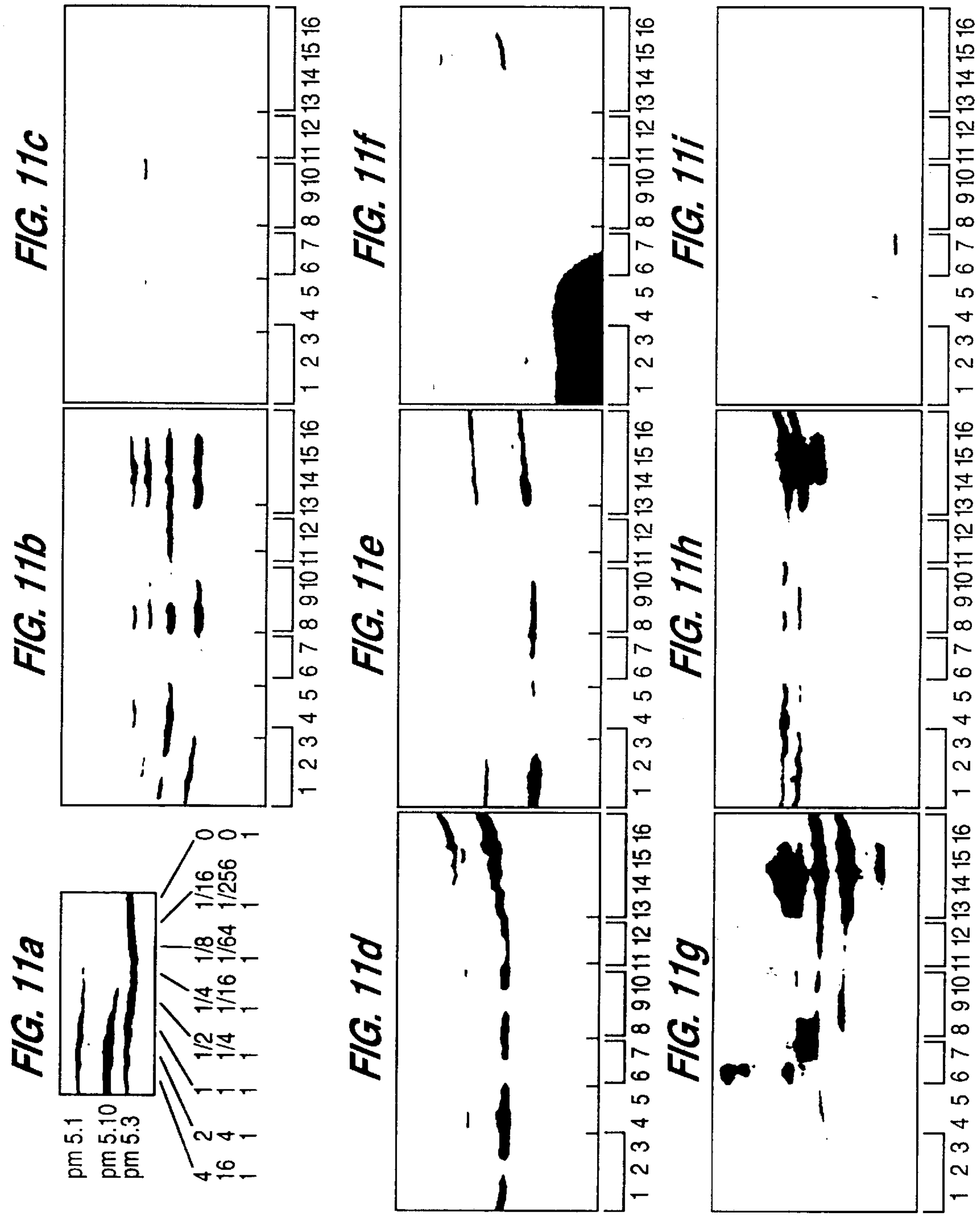
FIG. 11A Amplification of CD46 cDNA clones using PCR. CD46 cDNA clones, pm5.1, pm5.3 and pm5.10 were amplified together in the proportions indicated below each track. α[$^{32}$P]dCTP was incorporated into the PCR products and the samples were electrophoresed and autoradiographed.
FIG. 11B Electrophoresis of radiolabelled, amplified cDNA from lymphocytes (lanes 1–3), granulocytes (lane 4) and EBV-transformed B cells (lane 5), spermatozoa (lanes 6 and 7), leukemic cells (lanes 8–10), normal and malignant colon tissue from a patient with colon carcinoma (lanes 11 and 12 respectively), and full term placentae (lanes 13–16). samples 3–6 are from the same donor as are samples 1 and 7.

Five observations merit particular attention: 1) CD46 RNAs containing exon 7 (FIG. 11C) were preferentially expressed in EBV-transformed B cells (lane 5) and in two leukemic samples (lanes 8 and 10). RNAs containing exon 7 were also expressed in placentae, although to a lesser extent (lanes 13–16). 2) The ratio of the quantity of transcripts containing exon 8, to transcripts in which exon 8 have been deleted, was equivalent to the ratio of α and β isoforms detected on western blots in every tissue excepting sperm (FIGS. 9, 11D, 11E). This demonstrated that the α isoforms were derived from RNAs in which exon 8 had been inserted, and the β isoforms from RNAs in which exon 8 had been deleted. 3) Probing for the deletion of exon 9 demonstrated that RNA transcripts of this type occurred in 3 or the 4 placentae examined (FIG. 11F, lanes 14–16). 4) A transcript in which exons 12 and 13 were deleted occurred only in semen (FIG. 11I, lanes 6 and 7). 5) RNA transcripts both with and without exon 13 were present in every tissue and the ratio of these two groups of transcripts was similar in all tissues (FIG. 11G, 11H), Thus, each splice variant displayed a different distribution of expression, with tissue specific and allelic variations in splicing and with some RNAs expressed in every tissue.

EXAMPLE 7

Association of CD46 RNA Splice Variants with Protein Isoforms

Apart from three cases listed below, all of the different protein isoforms observed in each of the 16 tissues investigated (FIG. 9) correlated with the expression of a transcript with the appropriate sequence (FIGS. 11*a*–11*i*); all of this data is summarised in FIG. 12. FIGS. 13*a*–13*g* summarizes the nucleic acid sequence, amino acid assignments and exon assignments of exons 7 to 14.

FIG. 13-*a* includes SEQ ID NOS:11 and 12; FIG. 13-*b* includes SEQ ID NOS:17 and 18; FIG. 13-*c* includes SEQ ID NOS:19 and 20; FIG. 13-*d* includes SEQ ID NOS:21 and 22; FIG. 13-*e* includes SEQ ID NOS:23, 24 and 25; FIG. 13-*f* includes SEQ ID NOS:26 and 27; and FIG. 13-*g* includes SEQ ID NOS:28, 29 and 30.

Deletion of exons 12 and 13 would have little effect on protein $M_r$, as they code for few amino acids, but exons 7, 8 and 9, which encode STP rich protein, could be expected to significantly change the $M_r$ due to O-linked glycosylation of the mature protein. Transcript a has no deletions and gives rise to the γ isoform of 74 kDa seen in EBV-transformed and leukemic cells. Transcript c has deleted exon 7 and gives rise to an α isomer of CD46 (66 kDa). The deletion of exon 8 in transcript e gives rise to the β isoform of CD46 (56 kDa). Transcript g has deleted exon 9 and has only been found in low levels in some placentae. The expression of the corresponding protein was too low to be detected by western blot. Transcript i has deleted exons 7 and 9, is expressed by some placentae, and has a corresponding isoform of 63 kDa (ξ). Transcript k, in which all three STP-encoding exons (7–9) have been deleted, is expressed by some placentae at sufficiently high levels to encode detectable protein, however distortion in the gel at this site obscured detection. Transcripts b, d, f, h, j and l are similar to transcripts a, c, e, g, i and k respectively, but have also deleted exon 13, and so encode an alternative cytoplasmic tail. Neither transcript m (generated by the aberrant splicing of exon 12, described in 12), nor a corresponding protein isoform was detected in these tissues however this isoform may define a soluble form, as seen for instance in seminal fluid. Transcript n is expressed only in sperm and is derived from the deletion of exons 7, 8, 12 and 13, giving rise to a protein of 35 kDa (δ). Thus in almost all cases, the transcripts produced after the insertion or deletion of various exons were translated to produce the appropriate $M_r$ protein isoform.

Three cases in which the distribution of RNA transcripts did not correlate with the distribution of their corresponding protein isoforms were noted. (i) A unique higher $M_r$ protein isoform was found in granulocytes and no unique RNA transcript was observed, this possibly reflects cell-specific differences in glycosylation. (ii) Some RNA transcripts predicted to encode protein isoforms of lymphocytes were detected in semen, however these protein isoforms were not detected in isolated spermatozoa, indicating that semen RNA contains RNA from other cells. (iii) The 35 kDa protein isoform observed in spermatozoa was of slightly lower $M_r$ than that predicted from the RNA sequence. This could be due to the alternative usage of translational start sites previously suggested for other molecules in sperm, or possibly to different glycosylation patterns. These discrepancies suggest that, although the primary determinant of CD46 protein heterogeneity is the expression of alternatively spliced RNA, other factors can influence expression.

It will be apparent from Examples 4 to 7 describing tissues from a single donor and the same tissues from different donors that CD46 displays both a genetic polymorphism and an extensive tissue polymorphism, with 14 different mRNA transcripts, coding for different protein isoforms, identified in 16 tissues. In the genetic polymorphism, the difference in the two alleles determines the splicing of exon 8, which gives rise to variable proportions of the α (66 kDa) and β (56 kDa) chains with αα, αβ and ββ phenotypes. The second, and perhaps more interesting polymorphism, is that which occurs in different tissues and which gives rise to additional different protein isoforms of CD46 described in FIG. 12. These are: the γ isoform (74 kDa, transcripts a, b); the δ isoform of sperm 35 kDa, transcript n and the ξ isoform of placenta (63 kDa, transcripts i, j).

Tumour cells, such as EBV-transformed cells and leukemic cells, have the longest STP region, with no exons deleted (FIGS. 4*a*–4*e*). The reason for this is not apparent, but may extend the active part of the molecule above the more extensive glycocalyx of tumour cells. By contrast some placentae may have only a short stalk as exon 9 is deleted. The placenta-specific isoforms may be related to the allotypic reactivity of TLX.

There are also transcripts for three cytoplasmic tails, two of which appear to be present in all cells, and the third in spermatozoa. Example 8 below suggests that these tails generate different intracellular signals. The deletion of exons in the cytoplasmic region do not significantly change the $M_r$ of the protein and are not easily resolved by SDS-PAGE (FIG. 12), however the expression of each cytoplasmic tail has been confirmed using antipeptide antibodies. It is likely that more (native) protein isoforms exist in other tissues.

EXAMPLE 8

The sequences of the different CD46 variants were subjected to a computer analysis and homologies with sequences of known function were determined using "Prosearch": Lee F. Kolakowski's search of protein sequences against Amos Bairoch's PROSITE database. Sequences corresponding to known phosphorylation sites and nuclear localisation sites were identified.

(a) A sequence associated with cyclic AMP-dependent phosphorylation (KKGT) was identified in the "CYT1" cytoplasmic tail corresponding to the pm5.1 clone. This tail also contained the consensus sequence for Protein kinase C dependent phosphorylation (THR).

(b) Sequences associated with casein kinase 2 phosphorylation were identified in both the CYT 1 (pm5.1) and CYT 2 (pm5.3, pm5.10) cytoplasmic tails (THRE and TPAE respectively).

(c) The sequence KKKGK of the CYT 2 cytoplasmic tail has been identified as a nuclear localisation signal.

These results are suggestive of a signal role possibly phosphorylation based for portions of the CD46 molecule remote from the SCR domains active in the complement cascade. The activity status of the SCR domains could trigger this signal role through, for instance, conformation changes in the molecule. The signal is conceivably implicated in feedback or cascade enhancement roles.

EXAMPLE 9 complete cDNA and Amino Acid SequenceS

FIGS. 14*a*14–*d* depict a cDNA sequence and amino acid sequence for CD46 isoform PM5.3. The coding sequence is at nucleotides 83–1192. The signal polypeptide is encoded at nucleotides 83–184, and the mature polypeptide is encoded is encoded at nucleotides 185–1192. Nucleotides 939–983 encode exon 8 (STP-B). Nucleotides 1123–1247 encode exon 14 (CYT-2 and the 3' UT).

FIG. 15*a*–15*e* depict a cDNA sequence and amino acid sequence for CD46 isoform PM5.6. The coding sequence is at nucleotides 29–1147. The signal polypeptide is encoded at nucleotides 29–130, and the mature polypeptide is encoded at nucleotides 131–1147. Nucleotides 885–971 encode exons 8 and 9 (STP-BC). Exon 11 is intact, and ends at nucleotide 1046. A cryptic splice-site has led to loss of exon 12A, causing a frame-shift in translation of subsequent exons. Exon 12B (nucleotides 1047–73) is followed by exon 14 (nucleotides 1074–1986). Translation of exons 12B and 14 predicts a unique cytoplasmic tail of about 34 amino acids.

FIGS. 16*a*–16*d* depict a cDNA sequence and amino acid sequence for CD46 isoform PM5.8. The coding sequence is at nucleotides 94–1065. The signal polypeptide is encoded at nucleotides 94–195, and the mature polypeptide is encoded at nucleotides 196–1065. Exon 6 is intact, and ends at nucleotide 949. Intron 6 (413 nucleotides) has not been spliced out, and a read-through translation of the 353 nucleotide portion of intron 6 predicts a unique C-terminal sequence of 39 amino acids. PM5.8 includes 353 of the 413 nucleotides of intron 6 (85%).

It is to be understood that the description, specific examples and data, while indicating preferred embodiments, are given by way of illustration and exemplification and are not intended to limit the present invention. Various changes and modifications within the present invention will become apparent The drawings herewith are incorporated in this specification.

We claim:

1. An isolated polynucleotide encoding CD46 isoform PM5.3 (SEQ ID NO:42).

2. An isolated polynucleotide encoding CD46 isoform PM5.3 (SEQ ID NO:44).

3. An isolated polynucleotide encoding CD46 isoform PM5.8 (SEQ ID NO:46).

4. An isolated polynucleotide that encodes a CD46 isoform that comprises amino acids 1–336 of SEQ ID NO:42.

5. An isolated polynucleotide that encodes a CD46 isoform that comprises amino acids 1–339 of SEQ ID NO:44.

6. An isolated polynucleotide that encodes a CD46 isoform that comprises amino acids 1–290 of SEQ ID NO:46.

7. An isolated polynucleotide according to claim 4, wherein said polynucleotide comprises nucleotides 185–1192 of SEQ ID NO:41.

8. An isolated polynucleotide according to claim 5, wherein said polynucleotide comprises nucleotides 131–1147 of SEQ ID NO:43.

9. An isolated polynucleotide according to claim 6, wherein said polynucleotide comprises nucleotides 196–1065 SEQ ID NO:45.

10. method of identifying CD46 isoform PM5.3 present in a sample of mammalian tissue or fluid, comprising the steps of:

contacting said sample with a probe, wherein said probe comprises an oligonucleotide linked to a detectable marker, wherein said oligonucleotide comprises at least a 10-nucleotide fragment from a polynucleotide according to claim 1; and determining whether said probe hybridizes to DNA or RNA present within said sample.

11. A method of identifying CD46 isoform PM5.6 present in a sample of mammalian tissue or fluid, comprising the steps of:

contacting said sample with a probe, wherein said probe comprises an oligonucleotide linked to a detectable marker, wherein said oligonucleotide comprises at least a 10-nucleotide fragment from a polynucleotide according to claim 2; and determining whether said probe hybridizes to DNA or RNA present within said sample.

12. A method of identifying CD46 isoform PM5.8 present in a sample of mammalian tissue or fluid, comprising the steps of:

contacting said sample with a probe, wherein said probe comprises an oligonucleotide linked to a detectable marker, wherein said oligonucleotide comprises at least a 10 -nucleotide fragment from a polynucleotide according to claim 3; and determining whether said probe hybridizes to DNA or RNA present within said sample.

13. The method of claim 10 wherein said oligonucleotide further comprises part or all of exon 8.

* * * * *

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
( A ) LENGTH: 1659 base pairs
( B ) TYPE: nucleic acid
( C ) STRANDEDNESS: double
( D ) TOPOLOGY: linear ( i i ) MOLECULE TYPE: cDNA ( v i i ) IMMEDIATE SOURCE:
( B ) CLONE: pm5.1

( i x ) FEATURE:
( A ) NAME/KEY: CDS
( B ) LOCATION: 34..1167

( i x ) FEATURE:
( A ) NAME/KEY: sig_peptide
( B ) LOCATION: 34..135

( i x ) FEATURE:
( A ) NAME/KEY: mat_peptide
( B ) LOCATION: 136..1167

( x i ) SEQUENCE DESCRIPTION: SEQ ID NO:1:

```
AATTCGGGGA TAACAGCGTC TTCCGCGCCG CGC ATG GAG CCT CCC GGC CGC CGC      54
                                     Met Glu Pro Pro Gly Arg Arg
                                     -34             -30

GAG TGT CCC TTT CCT TCC TGG CGC TTT CCT GGG TTG CTT CTG GCG GCC     102
Glu Cys Pro Phe Pro Ser Trp Arg Phe Pro Gly Leu Leu Leu Ala Ala
        -25                 -20                 -15

ATG GTG TTG CTG CTG TAC TCC TTC TCC GAT GCC TGT GAG GAG CCA CCA     150
Met Val Leu Leu Leu Tyr Ser Phe Ser Asp Ala Cys Glu Glu Pro Pro
```

-continued

```
     -10                      -5                        1                    5

ACA TTT GAA GCT ATG GAG CTC ATT GGT AAA CCA AAA CCC TAC TAT GAG      198
Thr Phe Glu Ala Met Glu Leu Ile Gly Lys Pro Lys Pro Tyr Tyr Glu
                 10                  15                  20

ATT GGT GAA CGA GTA GAT TAT AAG TGT AAA AAA GGA TAC TTC TAT ATA      246
Ile Gly Glu Arg Val Asp Tyr Lys Cys Lys Lys Gly Tyr Phe Tyr Ile
             25                  30                  35

CCT CCT CTT GCC ACC CAT ACT ATT TGT GAT CGG AAT CAT ACA TGG CTA      294
Pro Pro Leu Ala Thr His Thr Ile Cys Asp Arg Asn His Thr Trp Leu
         40                  45                  50

CCT GTC TCA GAT GAC GCC TGT TAT AGA GAA ACA TGT CCA TAT ATA CGG      342
Pro Val Ser Asp Asp Ala Cys Tyr Arg Glu Thr Cys Pro Tyr Ile Arg
     55                  60                  65

GAT CCT TTA AAT GGC CAA GCA GTC CCT GCA AAT GGG ACT TAC GAG TTT      390
Asp Pro Leu Asn Gly Gln Ala Val Pro Ala Asn Gly Thr Tyr Glu Phe
 70                  75                  80                  85

GGT TAT CAG ATG CAC TTT ATT TGT AAT GAG GGT TAT TAC TTA ATT GGT      438
Gly Tyr Gln Met His Phe Ile Cys Asn Glu Gly Tyr Tyr Leu Ile Gly
                 90                  95                 100

GAA GAA ATT CTA TAT TGT GAA CTT AAA GGA TCA GTA GCA ATT TGG AGC      486
Glu Glu Ile Leu Tyr Cys Glu Leu Lys Gly Ser Val Ala Ile Trp Ser
            105                 110                 115

GGT AAG CCC CCA ATA TGT GAA AAG GTT TTG TGT ACA CCA CCT CCA AAA      534
Gly Lys Pro Pro Ile Cys Glu Lys Val Leu Cys Thr Pro Pro Pro Lys
        120                 125                 130

ATA AAA AAT GGA AAA CAC ACC TTT AGT GAA GTA GAA GTA TTT GAG TAT      582
Ile Lys Asn Gly Lys His Thr Phe Ser Glu Val Glu Val Phe Glu Tyr
    135                 140                 145

CTT GAT GCA GTA ACT TAT AGT TGT GAT CCT GCA CCT GGA CCA GAT CCA      630
Leu Asp Ala Val Thr Tyr Ser Cys Asp Pro Ala Pro Gly Pro Asp Pro
150                 155                 160                 165

TTT TCA CTT ATT GGA GAG AGC ACG ATT TAT TGT GGT GAC AAT TCA GTG      678
Phe Ser Leu Ile Gly Glu Ser Thr Ile Tyr Cys Gly Asp Asn Ser Val
                170                 175                 180

TGG AGT CGT GCT GCT CCA GAG TGT AAA GTG GTC AAA TGT CGA TTT CCA      726
Trp Ser Arg Ala Ala Pro Glu Cys Lys Val Val Lys Cys Arg Phe Pro
            185                 190                 195

GTA GTC GAA AAT GGA AAA CAG ATA TCA GGA TTT GGA AAA AAA TTT TAC      774
Val Val Glu Asn Gly Lys Gln Ile Ser Gly Phe Gly Lys Lys Phe Tyr
        200                 205                 210

TAC AAA GCA ACA GTT ATG TTT GAA TGC GAT AAG GGT TTT TAC CTC GAT      822
Tyr Lys Ala Thr Val Met Phe Glu Cys Asp Lys Gly Phe Tyr Leu Asp
    215                 220                 225

GGC AGC GAC ACA ATT GTC TGT GAC AGT AAC AGT ACT TGG GAT CCC CCA      870
Gly Ser Asp Thr Ile Val Cys Asp Ser Asn Ser Thr Trp Asp Pro Pro
230                 235                 240                 245

GTT CCA AAG TGT CTT AAA GTG TCG ACT TCT TCC ACT ACA AAA TCT CCA      918
Val Pro Lys Cys Leu Lys Val Ser Thr Ser Ser Thr Thr Lys Ser Pro
                250                 255                 260

GCG TCC AGT GCC TCA GGT CCT AGG CCT ACT TAC AAG CCT CCA GTC TCA      966
Ala Ser Ser Ala Ser Gly Pro Arg Pro Thr Tyr Lys Pro Pro Val Ser
            265                 270                 275

AAT TAT CCA GGA TAT CCT AAA CCT GAG GAA GGA ATA CTT GAC AGT TTG     1014
Asn Tyr Pro Gly Tyr Pro Lys Pro Glu Glu Gly Ile Leu Asp Ser Leu
        280                 285                 290

GAT GTT TGG GTC ATT GCT GTG ATT GTT ATT GCC ATA GTT GTT GGA GTT     1062
Asp Val Trp Val Ile Ala Val Ile Val Ile Ala Ile Val Val Gly Val
    295                 300                 305

GCA GTA ATT TGT GTT GTC CCG TAC AGA TAT CTT CAA AGG AGG AAG AAG     1110
Ala Val Ile Cys Val Val Pro Tyr Arg Tyr Leu Gln Arg Arg Lys Lys
```

-continued

```
310                      315                      320                      325

AAA GGC ACA TAC CTA ACT GAT GAG ACC CAC AGA GAA GTA AAA TTT ACT     1158
Lys Gly Thr Tyr Leu Thr Asp Glu Thr His Arg Glu Val Lys Phe Thr
                330                      335                      340

TCT CTC TGAGAAGGAG AGATGAGAGA AAGGTTTGAT TTTATCATTA AAAGGAAAGC      1214
Ser Leu

AGATGGTGGA GCTGAATATG CCACTTACCA GACTAAATCA ACCACTCCAG CAGAGCAGAG   1274

AGGCTGAATA GATTCCACAA CCTGGTTTGC CAGTTCATCT TTTGACTCTA TTAAAATCTT   1334

CAATAGTTGT TATTCTGTAG TTTCACTCTC ATGAGTGCAA CTGTGGCTTA GCTAATATTG   1394

CAATGTGGCT TGAATGTAGG TAGCATCCTT TGATGCTTCT TTGAAACTTG TATGAATTTG   1454

GGTATGAACA GATTGCCTGC TTTCCCTTAA ATAACACTTA GATTTATTGG ACCAGTCAGC   1514

ACAGCATGCC TGGTTGTATT AAAGCAGGGA TATGCTGTAT TTTATAAAAT TGGCAAAATT   1574

AGAGAAATAT AGTTCACAAT GAAATTATAT TTTCTTTGTA AAGAAAGTGG CTTGAAATCT   1634

TTTTTGTTCA AAGATTAATG CCCCG                                         1659
```

( 2 ) INFORMATION FOR SEQ ID NO:2:

( i ) SEQUENCE CHARACTERISTICS:
( A ) LENGTH: 377 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Pro Pro Gly Arg Arg Glu Cys Pro Phe Pro Ser Trp Arg Phe
-34             -30                 -25                 -20

Pro Gly Leu Leu Leu Ala Ala Met Val Leu Leu Leu Tyr Ser Phe Ser
            -15                 -10                 -5

Asp Ala Cys Glu Glu Pro Pro Thr Phe Glu Ala Met Glu Leu Ile Gly
         1                   5                  10

Lys Pro Lys Pro Tyr Tyr Glu Ile Gly Glu Arg Val Asp Tyr Lys Cys
 15                  20                  25                  30

Lys Lys Gly Tyr Phe Tyr Ile Pro Pro Leu Ala Thr His Thr Ile Cys
                 35                  40                  45

Asp Arg Asn His Thr Trp Leu Pro Val Ser Asp Asp Ala Cys Tyr Arg
             50                  55                  60

Glu Thr Cys Pro Tyr Ile Arg Asp Pro Leu Asn Gly Gln Ala Val Pro
         65                  70                  75

Ala Asn Gly Thr Tyr Glu Phe Gly Tyr Gln Met His Phe Ile Cys Asn
     80                  85                  90

Glu Gly Tyr Tyr Leu Ile Gly Glu Glu Ile Leu Tyr Cys Glu Leu Lys
 95                 100                 105                 110

Gly Ser Val Ala Ile Trp Ser Gly Lys Pro Pro Ile Cys Glu Lys Val
                115                 120                 125

Leu Cys Thr Pro Pro Pro Lys Ile Lys Asn Gly Lys His Thr Phe Ser
            130                 135                 140

Glu Val Glu Val Phe Glu Tyr Leu Asp Ala Val Thr Tyr Ser Cys Asp
        145                 150                 155

Pro Ala Pro Gly Pro Asp Pro Phe Ser Leu Ile Gly Glu Ser Thr Ile
    160                 165                 170

Tyr Cys Gly Asp Asn Ser Val Trp Ser Arg Ala Ala Pro Glu Cys Lys
175                 180                 185                 190

Val Val Lys Cys Arg Phe Pro Val Val Glu Asn Gly Lys Gln Ile Ser
```

| | | | | | | | | | | | | | | | |
|---|---|---|---|---|---|---|---|---|---|---|---|---|---|---|---|
| | | | | 195 | | | | | 200 | | | | | 205 | |
| Gly | Phe | Gly | Lys | Lys | Phe | Tyr | Tyr | Lys | Ala | Thr | Val | Met | Phe | Glu | Cys |
| | | | 210 | | | | | 215 | | | | | 220 | | |
| Asp | Lys | Gly | Phe | Tyr | Leu | Asp | Gly | Ser | Asp | Thr | Ile | Val | Cys | Asp | Ser |
| | | 225 | | | | | 230 | | | | | 235 | | | |
| Asn | Ser | Thr | Trp | Asp | Pro | Pro | Val | Pro | Lys | Cys | Leu | Lys | Val | Ser | Thr |
| | 240 | | | | | 245 | | | | | 250 | | | | |
| Ser | Ser | Thr | Thr | Lys | Ser | Pro | Ala | Ser | Ser | Ala | Ser | Gly | Pro | Arg | Pro |
| 255 | | | | | 260 | | | | | 265 | | | | | 270 |
| Thr | Tyr | Lys | Pro | Pro | Val | Ser | Asn | Tyr | Pro | Gly | Tyr | Pro | Lys | Pro | Glu |
| | | | | 275 | | | | | 280 | | | | | 285 | |
| Glu | Gly | Ile | Leu | Asp | Ser | Leu | Asp | Val | Trp | Val | Ile | Ala | Val | Ile | Val |
| | | | 290 | | | | | 295 | | | | | 300 | | |
| Ile | Ala | Ile | Val | Val | Gly | Val | Ala | Val | Ile | Cys | Val | Val | Pro | Tyr | Arg |
| | | 305 | | | | | 310 | | | | | 315 | | | |
| Tyr | Leu | Gln | Arg | Arg | Lys | Lys | Lys | Gly | Thr | Tyr | Leu | Thr | Asp | Glu | Thr |
| | 320 | | | | | 325 | | | | | 330 | | | | |
| His | Arg | Glu | Val | Lys | Phe | Thr | Ser | Leu | | | | | | | |
| 335 | | | | | 340 | | | | | | | | | | |

( 2 ) INFORMATION FOR SEQ ID NO:3:

( i ) SEQUENCE CHARACTERISTICS:
( A ) LENGTH: 483 base pairs
( B ) TYPE: nucleic acid
( C ) STRANDEDNESS: single
( D ) TOPOLOGY: linear ( i i ) MOLECULE TYPE: cDNA ( v i i ) IMMEDIATE SOURCE:
( A ) LIBRARY: pm5.6

( x i ) SEQUENCE DESCRIPTION: SEQ ID NO:3:

```
TGTTCAAAGA TTAATGCCAA CTCTTAAGAT TATTCTTTCA CCAACTATAG AATGTATTTT    60
ATATATCGTT CATTGTAAAA AGCCCTTAAA AATATGTGTA TACTACTTTG GCTCTTGTGC   120
ATAAAAACAA GAACACTGAA AATTGGGAAT ATGCACAAAC TTGGCTTCTT TAACCAAGAA   180
TATTATTGGA AAAGTTCTCT AAAAGTTAAT AGGGTAAATT CTCTATTTTT TGTAATGTGT   240
TCGGTGATTT CAGAAAGCTA GAAAGTGTAT GTGTGGCATT TGTTTTCACT TTTTAAAACA   300
TCCCTAACTG ATCGAATATA TCAGTAATTT CAGAATCAGA TGCATCCTTT CATAAGAAGT   360
GAGAGGACTC TGACAGCCAT AACAGGAGTG CCACTTCATG GTGCGAAGTG AACACTGTAG   420
TCTTGTTGTT TTCCCAAAGA GAACTCCGTA TGTTCTCTTA GGTTGAGTAA CCCACTCTGC   480
CCG                                                                 483
```

( 2 ) INFORMATION FOR SEQ ID NO:4:

( i ) SEQUENCE CHARACTERISTICS:
( A ) LENGTH: 420 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:4:

```
GTGTCGACTT CTTCCACTAC AAAATCTCCA GCGTCCAGTG CCTCAGGTCC TAGGCCTACT    60
TACAAGCCTC CAGTCTCAAA TTATCCAGGA TATCCTAAAC CTGAGGAAGG AATACTTGAC   120
```

-continued

| | | | | | | |
|---|---|---|---|---|---|---|
| AGTTTGGATG | TTTGGGTCAT | TGCTGTGATT | GTTATTGCCA | TAGTTGTTGG | AGTTGCAGTA | 180 |
| ATTTGTGTTG | TCCCGTACAG | ATATCTTCAA | AGGAGGAAGA | AGAAAGGCAC | ATACCTAACT | 240 |
| GATGAGACCC | ACAGAGAAGT | AAAATTTACT | TCTCTCTGAG | AAGGAGAGAT | GAGAGAAAGG | 300 |
| TTTGATTTTA | TCATTAAAAG | GAAAGCAGAT | GGTGGAGCTG | AATATGCCAC | TTACCAGACT | 360 |
| AAATCAACCA | CTCCAGCAGA | GCAGAGAGGC | TGAATAGATT | CCACAACCTG | GTTTGCCAGT | 420 |

( 2 ) INFORMATION FOR SEQ ID NO:5:

( i ) SEQUENCE CHARACTERISTICS:
( A ) LENGTH: 92 amino acids
( B ) TYPE: amino acid
( D ) TOPOLOGY: linear ( v i i ) IMMEDIATE SOURCE:
( B ) CLONE: pm5.1

( x i ) SEQUENCE DESCRIPTION: SEQ ID NO:5:

Val Ser Thr Ser Ser Thr Thr Lys Ser Pro Ala Ser Ser Ala Ser Gly
1 5 10 15

Pro Arg Pro Thr Tyr Lys Pro Pro Val Ser Asn Tyr Pro Gly Tyr Pro
20 25 30

Lys Pro Glu Glu Gly Ile Leu Asp Ser Leu Asp Val Trp Val Ile Ala
35 40 45

Val Ile Val Ile Ala Ile Val Val Gly Val Ala Val Ile Cys Val Val
50 55 60

Pro Tyr Arg Tyr Leu Gln Arg Arg Lys Lys Lys Gly Thr Tyr Leu Thr
65 70 75 80

Asp Glu Thr His Arg Glu Val Lys Phe Thr Ser Leu
85 90

( 2 ) INFORMATION FOR SEQ ID NO:6:

( i ) SEQUENCE CHARACTERISTICS:
( A ) LENGTH: 88 amino acids
( B ) TYPE: amino acid
( D ) TOPOLOGY: linear ( v i i ) IMMEDIATE SOURCE:
( B ) CLONE: pm5.6

( x i ) SEQUENCE DESCRIPTION: SEQ ID NO:6:

Val Ser Thr Ser Ser Thr Thr Lys Ser Pro Ala Ser Ser Ala Ser Gly
1 5 10 15

Pro Arg Pro Thr Tyr Lys Pro Pro Val Ser Asn Tyr Pro Gly Tyr Pro
20 25 30

Lys Pro Glu Glu Gly Ile Leu Asp Ser Leu Asp Val Trp Val Ile Ala
35 40 45

Val Ile Val Ile Ala Ile Asp Ile Phe Lys Gly Gly Arg Arg Lys Gly
50 55 60

Lys Gln Met Val Glu Leu Asn Met Pro Leu Thr Arg Leu Asn Gln Pro
65 70 75 80

Leu Gln Gln Ser Arg Glu Ala Glu
85

( 2 ) INFORMATION FOR SEQ ID NO:7:

( i ) SEQUENCE CHARACTERISTICS:
( A ) LENGTH: 99 amino acids
( B ) TYPE: amino acid
( D ) TOPOLOGY: linear -continued ( v i i ) IMMEDIATE SOURCE:
( B ) CLONE: pm5.10

( x i ) SEQUENCE DESCRIPTION: SEQ ID NO:7:

Val Ser Thr Ser Ser Thr Thr Lys Ser Pro Ala Ser Ser Ala Ser Gly
1 5 10 15

Pro Arg Pro Thr Tyr Lys Pro Pro Val Ser Asn Tyr Pro Gly Tyr Pro
20 25 30

Lys Pro Glu Glu Gly Ile Leu Asp Ser Leu Asp Val Trp Val Ile Ala
35 40 45

Val Ile Val Ile Ala Ile Val Val Gly Val Ala Val Ile Cys Val Val
50 55 60

Pro Tyr Arg Tyr Leu Gln Arg Arg Lys Lys Lys Gly Lys Ala Asp Gly
65 70 75 80

Gly Ala Glu Tyr Ala Thr Tyr Gln Thr Lys Ser Thr Thr Pro Ala Glu
85 90 95

Gln Arg Gly ( 2 ) INFORMATION FOR SEQ ID NO:8:

( i ) SEQUENCE CHARACTERISTICS:
( A ) LENGTH: 85 amino acids
( B ) TYPE: amino acid
( D ) TOPOLOGY: linear ( v i i ) IMMEDIATE SOURCE:
( B ) CLONE: pm5.3

( x i ) SEQUENCE DESCRIPTION: SEQ ID NO:8:

Val Ser Thr Ser Ser Thr Thr Lys Ser Pro Ala Ser Ser Ala Ser Gly
1 5 10 15

Tyr Pro Lys Pro Glu Glu Gly Ile Leu Asp Ser Leu Asp Val Trp Val
20 25 30

Ile Ala Val Ile Val Ile Ala Ile Val Val Gly Val Ala Val Ile Cys
35 40 45

Val Val Pro Tyr Arg Tyr Leu Gln Arg Arg Lys Lys Lys Gly Lys Ala
50 55 60

Asp Gly Gly Ala Glu Tyr Ala Thr Tyr Gln Thr Lys Ser Thr Thr Pro
65 70 75 80

Ala Glu Gln Arg Gly
85

( 2 ) INFORMATION FOR SEQ ID NO:9:

( i ) SEQUENCE CHARACTERISTICS:
( A ) LENGTH: 356 base pairs
( B ) TYPE: nucleic acid
( C ) STRANDEDNESS: double
( D ) TOPOLOGY: linear ( i i ) MOLECULE TYPE: cDNA ( v i i ) IMMEDIATE SOURCE:
( B ) CLONE: pm5.8

( i x ) FEATURE:
( A ) NAME/KEY: CDS
( B ) LOCATION: 1..120

( x i ) SEQUENCE DESCRIPTION: SEQ ID NO:9:

GGT ACA AAG GTT ATC TTT TTT CTG TCT TGG TTT GTT ATT GTT GTT GCT 48
Gly Thr Lys Val Ile Phe Phe Leu Ser Trp Phe Val Ile Val Val Ala
1 5 10 15

-continued

```
GTT CAT TTT AGA CTT TAT TTC TTT GAT ATT AAC TAT CAG TCA TAC AAA          96
Val His Phe Arg Leu Tyr Phe Phe Asp Ile Asn Tyr Gln Ser Tyr Lys
                20                  25                  30

ATA ACT GAA AAG AAA CAA TTT TAGTATTTAA CTCTGTCTTG TATTCATTTC           147
Ile Thr Glu Lys Lys Gln Phe
            35                  40

TATGCCAGAT GAATGACACG AAATTCACAT AAAATTCTGC TGTTGTGATT TTTTGTGCTT      207

TTCCAGGGTT CTTAGCACGT TATGTACATT GCATGGGTAT ATGCTTTTAA TATTTTTATG      267

TATAAAAAGT GAATTACAAC AACTTTTTGG AATTGAAACA TGGGCATTTT TATCTAAGTA      327

AGTCAACAAT GGCATAATTC ATATACCCG                                        356
```

( 2 ) INFORMATION FOR SEQ ID NO:10:

( i ) SEQUENCE CHARACTERISTICS:
( A ) LENGTH: 39 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Gly Thr Lys Val Ile Phe Phe Leu Ser Trp Phe Val Ile Val Val Ala
  1               5                  10                  15

Val His Phe Arg Leu Tyr Phe Phe Asp Ile Asn Tyr Gln Ser Tyr Lys
                20                  25                  30

Ile Thr Glu Lys Lys Gln Phe
            35
```

( 2 ) INFORMATION FOR SEQ ID NO:11:

( i ) SEQUENCE CHARACTERISTICS:
( A ) LENGTH: 45 base pairs
( B ) TYPE: nucleic acid
( C ) STRANDEDNESS: double
( D ) TOPOLOGY: linear ( v i i ) IMMEDIATE SOURCE:
( B ) CLONE: exon 7

( x i ) SEQUENCE DESCRIPTION: SEQ ID NO:11:

```
TGCTGCCTCC ATCTAGTACA AAACCTCCAG CTTTGAGTCA TTCAG                       45
```

( 2 ) INFORMATION FOR SEQ ID NO:12:

( i ) SEQUENCE CHARACTERISTICS:
( A ) LENGTH: 16 amino acids
( B ) TYPE: amino acid
( D ) TOPOLOGY: linear ( x i ) SEQUENCE DESCRIPTION: SEQ ID NO:12:

```
Val Leu Pro Pro Ser Ser Thr Lys Pro Pro Ala Ser Ser His Ser Val
1               5                   10                  15
```

( 2 ) INFORMATION FOR SEQ ID NO:13:

( i ) SEQUENCE CHARACTERISTICS:
( A ) LENGTH: 38 amino acids
( B ) TYPE: amino acid
( D ) TOPOLOGY: linear ( x i ) SEQUENCE DESCRIPTION: SEQ ID NO:13:

```
Val Val Gly Val Ala Val Ile Cys Val Val Pro Tyr Arg Tyr Leu Gln
1               5                   10                  15

Arg Arg Lys Lys Lys Gly Thr Tyr Leu Thr Asp Glu Thr His Arg Glu
```

-continued 20 25 30

Val Lys Phe Thr Ser Leu
35

( 2 ) INFORMATION FOR SEQ ID NO:14:

( i ) SEQUENCE CHARACTERISTICS:
( A ) LENGTH: 45 amino acids
( B ) TYPE: amino acid
( D ) TOPOLOGY: linear ( x i ) SEQUENCE DESCRIPTION: SEQ ID NO:14:

Val Val Gly Val Ala Val Ile Cys Val Val Pro Tyr Arg Tyr Leu Gln
1 5 10 15

Arg Arg Lys Lys Lys Gly Lys Ala Asp Gly Gly Ala Glu Tyr Ala Thr
20 25 30

Tyr Gln Thr Lys Ser Thr Thr Pro Ala Glu Gln Arg Gly
35 40 45

( 2 ) INFORMATION FOR SEQ ID NO:15:

( i ) SEQUENCE CHARACTERISTICS:
( A ) LENGTH: 34 amino acids
( B ) TYPE: amino acid
( D ) TOPOLOGY: linear ( x i ) SEQUENCE DESCRIPTION: SEQ ID NO:15:

Asp Ile Phe Lys Gly Gly Arg Arg Lys Gly Lys Gln Met Val Glu Leu
1 5 10 15

Asn Met Pro Leu Thr Arg Leu Asn Gln Pro Leu Gln Gln Ser Arg Glu
20 25 30

Ala Glu ( 2 ) INFORMATION FOR SEQ ID NO:16:

( i ) SEQUENCE CHARACTERISTICS:
( A ) LENGTH: 25 amino acids
( B ) TYPE: amino acid
( D ) TOPOLOGY: linear ( x i ) SEQUENCE DESCRIPTION: SEQ ID NO:16:

Gly Lys Gln Met Val Glu Leu Asn Met Pro Leu Thr Arg Leu Asn Gln
1 5 10 15

Pro Leu Gln Gln Ser Arg Glu Ala Glu
20 25

( 2 ) INFORMATION FOR SEQ ID NO:17:

( i ) SEQUENCE CHARACTERISTICS:
( A ) LENGTH: 45 base pairs
( B ) TYPE: nucleic acid
( C ) STRANDEDNESS: double
( D ) TOPOLOGY: linear ( v i i ) IMMEDIATE SOURCE:
( B ) CLONE: exon 8

( x i ) SEQUENCE DESCRIPTION: SEQ ID NO:17:

TGTCGACTTC TTCCACTACA AAATCTCCAG CGTCCAGTGC CTCAG 45

( 2 ) INFORMATION FOR SEQ ID NO:18:

( i ) SEQUENCE CHARACTERISTICS:
( A ) LENGTH: 15 amino acids
( B ) TYPE: amino acid -continued ( D ) TOPOLOGY: linear ( x i ) SEQUENCE DESCRIPTION: SEQ ID NO:18:

Val Ser Thr Ser Ser Thr Thr Lys Ser Pro Ala Ser Ser Ala Ser
1 5 10 15

( 2 ) INFORMATION FOR SEQ ID NO:19:

( i ) SEQUENCE CHARACTERISTICS:
( A ) LENGTH: 42 base pairs
( B ) TYPE: nucleic acid
( C ) STRANDEDNESS: double
( D ) TOPOLOGY: linear ( v i i ) IMMEDIATE SOURCE:
( B ) CLONE: exon 9

( x i ) SEQUENCE DESCRIPTION: SEQ ID NO:19:

GTCCTAGGCC TACTTACAAG CCTCCAGTCT CAAATTATCC AG 42

( 2 ) INFORMATION FOR SEQ ID NO:20:

( i ) SEQUENCE CHARACTERISTICS:
( A ) LENGTH: 14 amino acids
( B ) TYPE: amino acid
( D ) TOPOLOGY: linear ( x i ) SEQUENCE DESCRIPTION: SEQ ID NO:20:

Gly Pro Arg Pro Thr Tyr Lys Pro Pro Val Ser Asn Tyr Pro
1 5 10

( 2 ) INFORMATION FOR SEQ ID NO:21:

( i ) SEQUENCE CHARACTERISTICS:
( A ) LENGTH: 74 base pairs
( B ) TYPE: nucleic acid
( C ) STRANDEDNESS: double
( D ) TOPOLOGY: linear ( v i i ) IMMEDIATE SOURCE:
( B ) CLONE: exons 10/11

( x i ) SEQUENCE DESCRIPTION: SEQ ID NO:21:

GATATCCTAA ACCTGAGGAA GGAATACTTG ACAGTTTGGA TGTTTGGGTC ATTGCTGTGA 60

TTGTTATTGC CATA 74

( 2 ) INFORMATION FOR SEQ ID NO:22:

( i ) SEQUENCE CHARACTERISTICS:
( A ) LENGTH: 25 amino acids
( B ) TYPE: amino acid
( D ) TOPOLOGY: linear ( x i ) SEQUENCE DESCRIPTION: SEQ ID NO:22:

Gly Tyr Pro Lys Pro Glu Glu Gly Ile Leu Asp Ser Leu Asp Val Trp
1 5 10 15

Val Ile Ala Val Ile Val Ile Ala Ile
20 25

( 2 ) INFORMATION FOR SEQ ID NO:23:

( i ) SEQUENCE CHARACTERISTICS:
( A ) LENGTH: 65 base pairs
( B ) TYPE: nucleic acid
( C ) STRANDEDNESS: double
( D ) TOPOLOGY: linear ( v i i ) IMMEDIATE SOURCE:

( B ) CLONE: exon 12

( x i ) SEQUENCE DESCRIPTION: SEQ ID NO:23:

GTTGTTGGAG TTGCAGTAAT TTGTGTTGTC CCGTACAGAT ATCTTCAAAG GAGGAAGAAG 60

AAAGG 65

( 2 ) INFORMATION FOR SEQ ID NO:24:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:24:

Val Val Gly Val Ala Val Ile Cys Val Val Pro Tyr Arg Tyr Leu Gln
1 5 10 15

Arg Arg Lys Lys Lys Gly
20

( 2 ) INFORMATION FOR SEQ ID NO:25:

( i ) SEQUENCE CHARACTERISTICS:
( A ) LENGTH: 9 amino acids
( B ) TYPE: amino acid
( D ) TOPOLOGY: linear ( x i ) SEQUENCE DESCRIPTION: SEQ ID NO:25:

Asp Ile Phe Lys Gly Gly Arg Arg Lys
1 5

( 2 ) INFORMATION FOR SEQ ID NO:26:

( i ) SEQUENCE CHARACTERISTICS:
( A ) LENGTH: 58 base pairs
( B ) TYPE: nucleic acid
( C ) STRANDEDNESS: double
( D ) TOPOLOGY: linear ( v i i ) IMMEDIATE SOURCE:
( B ) CLONE: exon 13

( i x ) FEATURE:
( A ) NAME/KEY: CDS
( B ) LOCATION: 2..49

( x i ) SEQUENCE DESCRIPTION: SEQ ID NO:26:

C ACA TAC CTA ACT GAT GAG ACC CAC AGA GAA GTA AAA TTT ACT TCT 46
Thr Tyr Leu Thr Asp Glu Thr His Arg Glu Val Lys Phe Thr Ser
1 5 10 15

CTC TGAGAAGGA 58
Leu ( 2 ) INFORMATION FOR SEQ ID NO:27:

( i ) SEQUENCE CHARACTERISTICS:
( A ) LENGTH: 16 amino acids
( B ) TYPE: amino acid
( D ) TOPOLOGY: linear ( i i ) MOLECULE TYPE: protein ( x i ) SEQUENCE DESCRIPTION: SEQ ID NO:27:

Thr Tyr Leu Thr Asp Glu Thr His Arg Glu Val Lys Phe Thr Ser Leu
1 5 10 15

( 2 ) INFORMATION FOR SEQ ID NO:28:

-continued ( i ) SEQUENCE CHARACTERISTICS:
( A ) LENGTH: 84 base pairs
( B ) TYPE: nucleic acid
( C ) STRANDEDNESS: double
( D ) TOPOLOGY: linear ( v i i ) IMMEDIATE SOURCE:
( B ) CLONE: exon 14

( i x ) FEATURE:
( A ) NAME/KEY: CDS
( B ) LOCATION: 2..73

( x i ) SEQUENCE DESCRIPTION: SEQ ID NO:28:

```
G AAA GCA GAT GGT GGA GCT GAA TAT GCC ACT TAC CAG ACT AAA TCA        46
  Lys Ala Asp Gly Gly Ala Glu Tyr Ala Thr Tyr Gln Thr Lys Ser
   1               5                  10                  15

ACC ACT CCA GCA GAG CAG AGA GGC TGAATAGATT CCAC                      84
Thr Thr Pro Ala Glu Gln Arg Gly
                20
```

( 2 ) INFORMATION FOR SEQ ID NO:29:

( i ) SEQUENCE CHARACTERISTICS:
( A ) LENGTH: 23 amino acids
( B ) TYPE: amino acid
( D ) TOPOLOGY: linear ( i i ) MOLECULE TYPE: protein ( x i ) SEQUENCE DESCRIPTION: SEQ ID NO:29:

```
Lys Ala Asp Gly Gly Ala Glu Tyr Ala Thr Tyr Gln Thr Lys Ser Thr
 1               5                  10                  15

Thr Pro Ala Glu Gln Arg Gly
            20
```

( 2 ) INFORMATION FOR SEQ ID NO:30:

( i ) SEQUENCE CHARACTERISTICS:
( A ) LENGTH: 25 amino acids
( B ) TYPE: amino acid
( D ) TOPOLOGY: linear ( x i ) SEQUENCE DESCRIPTION: SEQ ID NO:30:

```
Gly Lys Gln Met Val Glu Leu Asn Met Pro Leu Thr Arg Leu Asn Gln
1               5                   10                  15

Pro Leu Gln Gln Ser Arg Glu Ala Glu
            20                  25
```

( 2 ) INFORMATION FOR SEQ ID NO:31:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( v i i ) IMMEDIATE SOURCE:
( B ) CLONE: p1

( x i ) SEQUENCE DESCRIPTION: SEQ ID NO:31:

```
GGCAGCGACA CAATTGTC                                                  18
```

( 2 ) INFORMATION FOR SEQ ID NO:32:

( i ) SEQUENCE CHARACTERISTICS:
( A ) LENGTH: 19 base pairs
( B ) TYPE: nucleic acid
( C ) STRANDEDNESS: single ( D ) TOPOLOGY: linear ( v i i ) IMMEDIATE SOURCE:
( B ) CLONE: p2

( x i ) SEQUENCE DESCRIPTION: SEQ ID NO:32:

CAGCCTCTCT GCTCTGCTG 19

( 2 ) INFORMATION FOR SEQ ID NO:33:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( v i i ) IMMEDIATE SOURCE:
( B ) CLONE: exons 6-7

( x i ) SEQUENCE DESCRIPTION: SEQ ID NO:33:

CTAGATGGAG GCAGCACTTT AAGACACTTT GG 32

( 2 ) INFORMATION FOR SEQ ID NO:34:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( v i i ) IMMEDIATE SOURCE:
( B ) CLONE: exons 8-9

( x i ) SEQUENCE DESCRIPTION: SEQ ID NO:34:

AAGTAGGCCT AGGACCTGAG GCACTGGACG 30

( 2 ) INFORMATION FOR SEQ ID NO:35:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( v i i ) IMMEDIATE SOURCE:
( B ) CLONE: exons 6-9

( x i ) SEQUENCE DESCRIPTION: SEQ ID NO:35:

TAAGTAGGCC TAGGACCTTT AAGACACTTT G 31

( 2 ) INFORMATION FOR SEQ ID NO:36:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( v i i ) IMMEDIATE SOURCE:
( B ) CLONE: exons 8-10

( x i ) SEQUENCE DESCRIPTION: SEQ ID NO:36:

CAGGTTTAGG ATATCCTGAG GCACTGGACG 30

( 2 ) INFORMATION FOR SEQ ID NO:37:

( i ) SEQUENCE CHARACTERISTICS:
( A ) LENGTH: 36 base pairs
( B ) TYPE: nucleic acid
( C ) STRANDEDNESS: single ( D ) TOPOLOGY: linear ( v i i ) IMMEDIATE SOURCE:
( B ) CLONE: exon 13

( x i ) SEQUENCE DESCRIPTION: SEQ ID NO:37:

CCTTCTCAGA GAGAAGTAAA TTTTACTTCT CTGTGG 36

( 2 ) INFORMATION FOR SEQ ID NO:38:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( v i i ) IMMEDIATE SOURCE:
( B ) CLONE: exons 12-14

( x i ) SEQUENCE DESCRIPTION: SEQ ID NO:38:

CCACCATCTG CTTTCCCTTT CTTCTTCCTC C 31

( 2 ) INFORMATION FOR SEQ ID NO:39:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( v i i ) IMMEDIATE SOURCE:
( B ) CLONE: exons 11-14

( x i ) SEQUENCE DESCRIPTION: SEQ ID NO:39:

CCACCATCTG CTTTCCTATG GCAATAACAA TC 32

( 2 ) INFORMATION FOR SEQ ID NO:40:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:40:

TGTTGTCCCG TACAG 15

( 2 ) INFORMATION FOR SEQ ID NO:41:

( i ) SEQUENCE CHARACTERISTICS:
( A ) LENGTH: 1247 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 83..1192

( i x ) FEATURE:
( A ) NAME/KEY: mat_peptide
( B ) LOCATION: 185..1192

( x i ) SEQUENCE DESCRIPTION: SEQ ID NO:41:

```
AATTCGGGGG ACTTCCCTGC TCGGCTGGCT CTCGGTTTCT CTGCTTTCCT CCGGAGAAAT   60

AACAGCGTCT TCCGCGCCGC GC ATG GAG CCT CCC GGC CGC CGC GAG TGT CCC   112
                         Met Glu Pro Pro Gly Arg Arg Glu Cys Pro
                         -34             -30                 -25
```

-continued

TTT CCT TCC TGG CGC TTT CCT GGG TTG CTT CTG GCG GCC ATG GTG TTG 160
Phe Pro Ser Trp Arg Phe Pro Gly Leu Leu Leu Ala Ala Met Val Leu
-20 -15 -10

CTG CTG TAC TCC TTC TCC GAT GCC TGT GAG GAG CCA CCA ACA TTT GAA 208
Leu Leu Tyr Ser Phe Ser Asp Ala Cys Glu Glu Pro Pro Thr Phe Glu
-5 1 5

GCT ATG GAG CTC ATT GGT AAA CCA AAA CCC TAC TAT GAG ATT GGT GAA 256
Ala Met Glu Leu Ile Gly Lys Pro Lys Pro Tyr Tyr Glu Ile Gly Glu
10 15 20

CGA GTA GAT TAT AAG TGT AAA AAA GGA TAC TTC TAT ATA CCT CCT CTT 304
Arg Val Asp Tyr Lys Cys Lys Lys Gly Tyr Phe Tyr Ile Pro Pro Leu
25 30 35 40

GCC ACC CAT ACT ATT TGT GAT CGG AAT CAT ACA TGG CTA CCT GTC TCA 352
Ala Thr His Thr Ile Cys Asp Arg Asn His Thr Trp Leu Pro Val Ser
45 50 55

GAT GAC GCC TGT TAT AGA GAA ACA TGT CCA TAT ATA CGG GAT CCT TTA 400
Asp Asp Ala Cys Tyr Arg Glu Thr Cys Pro Tyr Ile Arg Asp Pro Leu
60 65 70

AAT GGC CAA GCA GTC CCT GCA AAT GGG ACT TAC GAG TTT GGT TAT CAG 448
Asn Gly Gln Ala Val Pro Ala Asn Gly Thr Tyr Glu Phe Gly Tyr Gln
75 80 85

ATG CAC TTT ATT TGT AAT GAG GGT TAT TAC TTA ATT GGT GAA GAA ATT 496
Met His Phe Ile Cys Asn Glu Gly Tyr Tyr Leu Ile Gly Glu Glu Ile
90 95 100

CTA TAT TGT GAA CTT AAA GGA TCA GTA GCA ATT TGG AGC GGT AAG CCC 544
Leu Tyr Cys Glu Leu Lys Gly Ser Val Ala Ile Trp Ser Gly Lys Pro
105 110 115 120

CCA ATA TGT GAA AAG GTT TTG TGT ACA CCA CCT CCA AAA ATA AAA AAT 592
Pro Ile Cys Glu Lys Val Leu Cys Thr Pro Pro Pro Lys Ile Lys Asn
125 130 135

GGA AAA CAC ACC TTT AGT GAA GTA GAA GTA TTT GAG TAT CTT GAT GCA 640
Gly Lys His Thr Phe Ser Glu Val Glu Val Phe Glu Tyr Leu Asp Ala
140 145 150

GTA ACT TAT AGT TGT GAT CCT GCA CCT GGA CCA GAT CCA TTT TCA CTT 688
Val Thr Tyr Ser Cys Asp Pro Ala Pro Gly Pro Asp Pro Phe Ser Leu
155 160 165

ATT GGA GAG AGC ACG ATT TAT TGT GGT GAC AAT TCA GTG TGG AGT CGT 736
Ile Gly Glu Ser Thr Ile Tyr Cys Gly Asp Asn Ser Val Trp Ser Arg
170 175 180

GCT GCT CCA GAG TGT AAA GTG GTC AAA TGT CGA TTT CCA GTA GTC GAA 784
Ala Ala Pro Glu Cys Lys Val Val Lys Cys Arg Phe Pro Val Val Glu
185 190 195 200

AAT GGA AAA CAG ATA TCA GGA TTT GGA AAA AAA TTT TAC TAC AAA GCA 832
Asn Gly Lys Gln Ile Ser Gly Phe Gly Lys Lys Phe Tyr Tyr Lys Ala
205 210 215

ACA GTT ATG TTT GAA TGC GAT AAG GGT TTT TAC CTC GAT GGC AGC GAC 880
Thr Val Met Phe Glu Cys Asp Lys Gly Phe Tyr Leu Asp Gly Ser Asp
220 225 230

ACA ATT GTC TGT GAC AGT AAC AGT ACT TGG GAT CCC CCA GTT CCA AAG 928
Thr Ile Val Cys Asp Ser Asn Ser Thr Trp Asp Pro Pro Val Pro Lys
235 240 245

TGT CTT AAA GTG TCG ACT TCT TCC ACT ACA AAA TCT CCA GCG TCC AGT 976
Cys Leu Lys Val Ser Thr Ser Ser Thr Thr Lys Ser Pro Ala Ser Ser
250 255 260

GCC TCA GGA TAT CCT AAA CCT GAG GAA GGA ATA CTT GAC AGT TTG GAT 1024
Ala Ser Gly Tyr Pro Lys Pro Glu Glu Gly Ile Leu Asp Ser Leu Asp
265 270 275 280

GTT TGG GTC ATT GCT GTG ATT GTT ATT GCC ATA GTT GTT GGA GTT GCA 1072
Val Trp Val Ile Ala Val Ile Val Ile Ala Ile Val Val Gly Val Ala
285 290 295

```
GTA ATT TGT GTT GTC CCG TAC AGA TAT CTT CAA AGG AGG AAG AAG AAA        1120
Val Ile Cys Val Val Pro Tyr Arg Tyr Leu Gln Arg Arg Lys Lys Lys
            300                 305                 310

GGG AAA GCA GAT GGT GGA GCT GAA TAT GCC ACT TAC CAG ACT AAA TCA        1168
Gly Lys Ala Asp Gly Gly Ala Glu Tyr Ala Thr Tyr Gln Thr Lys Ser
        315                 320                 325

ACC ACT CCA GCA GAG CAG AGA GGC TGAATAGATT CCACAACCTG GTTTGCCAGT       1222
Thr Thr Pro Ala Glu Gln Arg Gly
    330                 335

TCATCTTTTG ACTCTATCCC GCCCG                                            1247
```

( 2 ) INFORMATION FOR SEQ ID NO:42:

( i ) SEQUENCE CHARACTERISTICS:
( A ) LENGTH: 370 amino acids
( B ) TYPE: amino acid
( D ) TOPOLOGY: linear ( i i ) MOLECULE TYPE: protein ( x i ) SEQUENCE DESCRIPTION: SEQ ID NO:42:

```
Met Glu Pro Pro Gly Arg Arg Glu Cys Pro Phe Pro Ser Trp Arg Phe
-34                 -30                 -25                 -20

Pro Gly Leu Leu Leu Ala Ala Met Val Leu Leu Leu Tyr Ser Phe Ser
            -15                 -10                 -5

Asp Ala Cys Glu Glu Pro Pro Thr Phe Glu Ala Met Glu Leu Ile Gly
        1               5                   10

Lys Pro Lys Pro Tyr Tyr Glu Ile Gly Glu Arg Val Asp Tyr Lys Cys
 15                  20                  25                  30

Lys Lys Gly Tyr Phe Tyr Ile Pro Pro Leu Ala Thr His Thr Ile Cys
                35                  40                  45

Asp Arg Asn His Thr Trp Leu Pro Val Ser Asp Asp Ala Cys Tyr Arg
            50                  55                  60

Glu Thr Cys Pro Tyr Ile Arg Asp Pro Leu Asn Gly Gln Ala Val Pro
        65                  70                  75

Ala Asn Gly Thr Tyr Glu Phe Gly Tyr Gln Met His Phe Ile Cys Asn
    80                  85                  90

Glu Gly Tyr Tyr Leu Ile Gly Glu Glu Ile Leu Tyr Cys Glu Leu Lys
 95                 100                 105                 110

Gly Ser Val Ala Ile Trp Ser Gly Lys Pro Pro Ile Cys Glu Lys Val
                115                 120                 125

Leu Cys Thr Pro Pro Pro Lys Ile Lys Asn Gly Lys His Thr Phe Ser
            130                 135                 140

Glu Val Glu Val Phe Glu Tyr Leu Asp Ala Val Thr Tyr Ser Cys Asp
        145                 150                 155

Pro Ala Pro Gly Pro Asp Pro Phe Ser Leu Ile Gly Glu Ser Thr Ile
    160                 165                 170

Tyr Cys Gly Asp Asn Ser Val Trp Ser Arg Ala Ala Pro Glu Cys Lys
175                 180                 185                 190

Val Val Lys Cys Arg Phe Pro Val Val Glu Asn Gly Lys Gln Ile Ser
                195                 200                 205

Gly Phe Gly Lys Lys Phe Tyr Tyr Lys Ala Thr Val Met Phe Glu Cys
            210                 215                 220

Asp Lys Gly Phe Tyr Leu Asp Gly Ser Asp Thr Ile Val Cys Asp Ser
        225                 230                 235

Asn Ser Thr Trp Asp Pro Pro Val Pro Lys Cys Leu Lys Val Ser Thr
    240                 245                 250
```

-continued

Ser Ser Thr Thr Lys Ser Pro Ala Ser Ser Ala Ser Gly Tyr Pro Lys
255 260 265 270

Pro Glu Glu Gly Ile Leu Asp Ser Leu Asp Val Trp Val Ile Ala Val
275 280 285

Ile Val Ile Ala Ile Val Val Gly Val Ala Val Ile Cys Val Val Pro
290 295 300

Tyr Arg Tyr Leu Gln Arg Arg Lys Lys Lys Gly Lys Ala Asp Gly Gly
305 310 315

Ala Glu Tyr Ala Thr Tyr Gln Thr Lys Ser Thr Thr Pro Ala Glu Gln
320 325 330

Arg Gly
335

( 2 ) INFORMATION FOR SEQ ID NO:43:

( i ) SEQUENCE CHARACTERISTICS:
( A ) LENGTH: 1986 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 29..1147

( i x ) FEATURE:
( A ) NAME/KEY: mat_peptide
( B ) LOCATION: 131..1147

( x i ) SEQUENCE DESCRIPTION: SEQ ID NO:43:

AATTCGGGCG GGGTCTTCCG CGCCGCGC ATG GAG CCT CCC GGC CGC CGC GAG 52
Met Glu Pro Pro Gly Arg Arg Glu
-34 -30

TGT CCC TTT CCT TCC TGG CGC TTT CCT GGG TTG CTT CTG GCG GCC ATG 100
Cys Pro Phe Pro Ser Trp Arg Phe Pro Gly Leu Leu Leu Ala Ala Met
-25 -20 -15

GTG TTG CTG CTG TAC TCC TTC TCC GAT GCC TGT GAG GAG CCA CCA ACA 148
Val Leu Leu Leu Tyr Ser Phe Ser Asp Ala Cys Glu Glu Pro Pro Thr
-10 -5 1 5

TTT GAA GCT ATG GAG CTC ATT GGT AAA CCA AAA CCC TAC TAT GAG ATT 196
Phe Glu Ala Met Glu Leu Ile Gly Lys Pro Lys Pro Tyr Tyr Glu Ile
10 15 20

GGT GAA CGA GTA GAT TAT AAG TGT AAA AAA GGA TAC TTC TAT ATA CCT 244
Gly Glu Arg Val Asp Tyr Lys Cys Lys Lys Gly Tyr Phe Tyr Ile Pro
25 30 35

CCT CTT GCC ACC CAT ACT ATT TGT GAT CGG AAT CAT ACA TGG CTA CCT 292
Pro Leu Ala Thr His Thr Ile Cys Asp Arg Asn His Thr Trp Leu Pro
40 45 50

GTC TCA GAT GAC GCC TGT TAT AGA GAA ACA TGT CCA TAT ATA CGG GAT 340
Val Ser Asp Asp Ala Cys Tyr Arg Glu Thr Cys Pro Tyr Ile Arg Asp
55 60 65 70

CCT TTA AAT GGC CAA GCA GTC CCT GCA AAT GGG ACT TAC GAG TTT GGT 388
Pro Leu Asn Gly Gln Ala Val Pro Ala Asn Gly Thr Tyr Glu Phe Gly
75 80 85

TAT CAG ATG CAC TTT ATT TGT AAT GAG GGT TAT TAC TTA ATT GGT GAA 436
Tyr Gln Met His Phe Ile Cys Asn Glu Gly Tyr Tyr Leu Ile Gly Glu
90 95 100

GAA ATT CTA TAT TGT GAA CTT AAA GGA TCA GTA GCA ATT TGG AGC GGT 484
Glu Ile Leu Tyr Cys Glu Leu Lys Gly Ser Val Ala Ile Trp Ser Gly
105 110 115

-continued

```
AAG CCC CCA ATA TGT GAA AAG GTT TTG TGT ACA CCA CCT CCA AAA ATA      532
Lys Pro Pro Ile Cys Glu Lys Val Leu Cys Thr Pro Pro Pro Lys Ile
    120                 125                 130

AAA AAT GGA AAA CAC ACC TTT AGT GAA GTA GAA GTA TTT GAG TAT CTT      580
Lys Asn Gly Lys His Thr Phe Ser Glu Val Glu Val Phe Glu Tyr Leu
135                 140                 145                 150

GAT GCA GTA ACT TAT AGT TGT GAT CCT GCA CCT GGA CCA GAT CCA TTT      628
Asp Ala Val Thr Tyr Ser Cys Asp Pro Ala Pro Gly Pro Asp Pro Phe
                155                 160                 165

TCA CTT ATT GGA GAG AGC ACG ATT TAT TGT GGT GAC AAT TCA GTG TGG      676
Ser Leu Ile Gly Glu Ser Thr Ile Tyr Cys Gly Asp Asn Ser Val Trp
            170                 175                 180

AGT CGT GCT GCT CCA GAG TGT AAA GTG GTC AAA TGT CGA TTT CCA GTA      724
Ser Arg Ala Ala Pro Glu Cys Lys Val Val Lys Cys Arg Phe Pro Val
        185                 190                 195

GTC GAA AAT GGA AAA CAG ATA TCA GGA TTT GGA AAA AAA TTT TAC TAC      772
Val Glu Asn Gly Lys Gln Ile Ser Gly Phe Gly Lys Lys Phe Tyr Tyr
    200                 205                 210

AAA GCA ACA GTT ATG TTT GAA TGC GAT AAG GGT TTT TAC CTC GAT GGC      820
Lys Ala Thr Val Met Phe Glu Cys Asp Lys Gly Phe Tyr Leu Asp Gly
215                 220                 225                 230

AGC GAC ACA ATT GTC TGT GAC AGT AAC AGT ACT TGG GAT CCC CCA GTT      868
Ser Asp Thr Ile Val Cys Asp Ser Asn Ser Thr Trp Asp Pro Pro Val
                235                 240                 245

CCA AAG TGT CTT AAA GTG TCG ACT TCT TCC ACT ACA AAA TCT CCA GCG      916
Pro Lys Cys Leu Lys Val Ser Thr Ser Ser Thr Thr Lys Ser Pro Ala
            250                 255                 260

TCC AGT GCC TCA GGT CCT AGG CCT ACT TAC AAG CCT CCA GTC TCA AAT      964
Ser Ser Ala Ser Gly Pro Arg Pro Thr Tyr Lys Pro Pro Val Ser Asn
        265                 270                 275

TAT CCA GGA TAT CCT AAA CCT GAG GAA GGA ATA CTT GAC AGT TTG GAT     1012
Tyr Pro Gly Tyr Pro Lys Pro Glu Glu Gly Ile Leu Asp Ser Leu Asp
    280                 285                 290

GTT TGG GTC ATT GCT GTG ATT GTT ATT GCC ATA GAT ATC TTC AAA GGA     1060
Val Trp Val Ile Ala Val Ile Val Ile Ala Ile Asp Ile Phe Lys Gly
295                 300                 305                 310

GGA AGA AGA AAG GGA AAG CAG ATG GTG GAG CTG AAT ATG CCA CTT ACC     1108
Gly Arg Arg Lys Gly Lys Gln Met Val Glu Leu Asn Met Pro Leu Thr
                315                 320                 325

AGA CTA AAT CAA CCA CTC CAG CAG AGC AGA GAG GCT GAA TAGATTCCAC      1157
Arg Leu Asn Gln Pro Leu Gln Gln Ser Arg Glu Ala Glu
            330                 335

AACCTGGTTT GCCAGTTCAT CTTTTGACTC TATTAAAATC TTCAATAGTT GTTATTCTGT   1217

AGTTTCACTC TCATGAGTGC AACTGTGGCT TAGCTAATAT TGCAATGTGG CTTGAATGTA   1277

GGTAGCATCC TTTGATGCTT CTTTGAAACT TGTATGAATT TGGGTATGAA CAGATTGCCT   1337

GCTTTCCCTT AAATAACACT TAGATTTATT GGACCAGTCA GCACAGCATG CCTGGTTGTA   1397

TTAAAGCAGG GATATGCTGT ATTTTATAAA ATTGGCAAAA TTAGAGAAAT ATAGTTCACA   1457

ATGAAATTAT ATTTTCTTTG TAAAGAAAGT GGCTTGAAAT CTTTTTTGTT CAAAGATTAA   1517

TGCCAACTCT TAAGATTATT CTTTCACCAA CTATAGAATG TATTTTATAT ATCGTTCATT   1577

GTAAAAAGCC CTTAAAAATA TGTGTATACT ACTTTGGCTC TTGTGCATAA AAACAAGAAC   1637

ACTGAAAATT GGGAATATGC ACAAACTTGG CTTCTTTAAC CAAGAATATT ATTGGAAAAG   1697

TTCTCTAAAA GTTAATAGGG TAAATTCTCT ATTTTTTGTA ATGTGTTCGG TGATTTCAGA   1757

AAGCTAGAAA GTGTATGTGT GGCATTTGTT TTCACTTTTT AAAACATCCC TAACTGATCG   1817

AATATATCAG TAATTTCAGA ATCAGATGCA TCCTTTCATA AGAAGTGAGA GGACTCTGAC   1877
```

```
AGCCATAACA GGAGTGCCAC TTCATGGTGC GAAGTGAACA CTGTAGTCTT GTTGTTTTCC    1937

CAAAGAGAAC TCCGTATGTT CTCTTAGGTT GAGTAACCCA CTCTGCCCG                1986
```

( 2 ) INFORMATION FOR SEQ ID NO:44:

( i ) SEQUENCE CHARACTERISTICS:
( A ) LENGTH: 373 amino acids
( B ) TYPE: amino acid
( D ) TOPOLOGY: linear ( i i ) MOLECULE TYPE: protein ( x i ) SEQUENCE DESCRIPTION: SEQ ID NO:44:

```
Met Glu Pro Pro Gly Arg Arg Glu Cys Pro Phe Pro Ser Trp Arg Phe
-34             -30                 -25                 -20

Pro Gly Leu Leu Leu Ala Ala Met Val Leu Leu Leu Tyr Ser Phe Ser
            -15                 -10                 -5

Asp Ala Cys Glu Glu Pro Pro Thr Phe Glu Ala Met Glu Leu Ile Gly
         1                   5                  10

Lys Pro Lys Pro Tyr Tyr Glu Ile Gly Glu Arg Val Asp Tyr Lys Cys
 15                  20                  25                  30

Lys Lys Gly Tyr Phe Tyr Ile Pro Pro Leu Ala Thr His Thr Ile Cys
                 35                  40                  45

Asp Arg Asn His Thr Trp Leu Pro Val Ser Asp Asp Ala Cys Tyr Arg
             50                  55                  60

Glu Thr Cys Pro Tyr Ile Arg Asp Pro Leu Asn Gly Gln Ala Val Pro
         65                  70                  75

Ala Asn Gly Thr Tyr Glu Phe Gly Tyr Gln Met His Phe Ile Cys Asn
     80                  85                  90

Glu Gly Tyr Tyr Leu Ile Gly Glu Glu Ile Leu Tyr Cys Glu Leu Lys
 95                 100                 105                 110

Gly Ser Val Ala Ile Trp Ser Gly Lys Pro Pro Ile Cys Glu Lys Val
                115                 120                 125

Leu Cys Thr Pro Pro Pro Lys Ile Lys Asn Gly Lys His Thr Phe Ser
            130                 135                 140

Glu Val Glu Val Phe Glu Tyr Leu Asp Ala Val Thr Tyr Ser Cys Asp
        145                 150                 155

Pro Ala Pro Gly Pro Asp Pro Phe Ser Leu Ile Gly Glu Ser Thr Ile
    160                 165                 170

Tyr Cys Gly Asp Asn Ser Val Trp Ser Arg Ala Ala Pro Glu Cys Lys
175                 180                 185                 190

Val Val Lys Cys Arg Phe Pro Val Val Glu Asn Gly Lys Gln Ile Ser
                195                 200                 205

Gly Phe Gly Lys Lys Phe Tyr Tyr Lys Ala Thr Val Met Phe Glu Cys
            210                 215                 220

Asp Lys Gly Phe Tyr Leu Asp Gly Ser Asp Thr Ile Val Cys Asp Ser
        225                 230                 235

Asn Ser Thr Trp Asp Pro Pro Val Pro Lys Cys Leu Lys Val Ser Thr
    240                 245                 250

Ser Ser Thr Thr Lys Ser Pro Ala Ser Ser Ala Ser Gly Pro Arg Pro
255                 260                 265                 270

Thr Tyr Lys Pro Pro Val Ser Asn Tyr Pro Gly Tyr Pro Lys Pro Glu
                275                 280                 285

Glu Gly Ile Leu Asp Ser Leu Asp Val Trp Val Ile Ala Val Ile Val
            290                 295                 300

Ile Ala Ile Asp Ile Phe Lys Gly Gly Arg Arg Lys Gly Lys Gln Met
```

```
            305                         310                         315

Val Glu Leu Asn Met Pro Leu Thr Arg Leu Asn Gln Pro Leu Gln Gln
    320                     325                     330

Ser Arg Glu Ala Glu
335
```

( 2 ) INFORMATION FOR SEQ ID NO:45:

( i ) SEQUENCE CHARACTERISTICS:
( A ) LENGTH: 1304 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 94..1065

( i x ) FEATURE:
( A ) NAME/KEY: mat_peptide
( B ) LOCATION: 196..1065

( x i ) SEQUENCE DESCRIPTION: SEQ ID NO:45:

```
AATTCGGTGG ACCCAGAAGG GACTTCCCTG CTCGGCTGGC TCTCGGTTTC TCTGCTTTCC      60

TCCGGAGAAA TAACAGCGTC TTCCGCGCCG CGC ATG GAG CCT CCC GGC CGC CGC      114
                                     Met Glu Pro Pro Gly Arg Arg
                                     -34                 -30

GAG TGT CCC TTT CCT TCC TGG CGC TTT CCT GGG TTG CTT CTG GCG GCC      162
Glu Cys Pro Phe Pro Ser Trp Arg Phe Pro Gly Leu Leu Leu Ala Ala
        -25                 -20                 -15

ATG GTG TTG CTG CTG TAC TCC TTC TCC GAT GCC TGT GAG GAG CCA CCA      210
Met Val Leu Leu Leu Tyr Ser Phe Ser Asp Ala Cys Glu Glu Pro Pro
    -10                  -5                   1                   5

ACA TTT GAA GCT ATG GAG CTC ATT GGT AAA CCA AAA CCC TAC TAT GAG      258
Thr Phe Glu Ala Met Glu Leu Ile Gly Lys Pro Lys Pro Tyr Tyr Glu
                 10                  15                  20

ATT GGT GAA CGA GTA GAT TAT AAG TGT AAA AAA GGA TAC TTC TAT ATA      306
Ile Gly Glu Arg Val Asp Tyr Lys Cys Lys Lys Gly Tyr Phe Tyr Ile
             25                  30                  35

CCT CCT CTT GCC ACC CAT ACT ATT TGT GAT CGG AAT CAT ACA TGG CTA      354
Pro Pro Leu Ala Thr His Thr Ile Cys Asp Arg Asn His Thr Trp Leu
         40                  45                  50

CCT GTC TCA GAT GAC GCC TGT TAT AGA GAA ACA TGT CCA TAT ATA CGG      402
Pro Val Ser Asp Asp Ala Cys Tyr Arg Glu Thr Cys Pro Tyr Ile Arg
     55                  60                  65

GAT CCT TTA AAT GGC CAA GCA GTC CCT GCA AAT GGG ACT TAC GAG TTT      450
Asp Pro Leu Asn Gly Gln Ala Val Pro Ala Asn Gly Thr Tyr Glu Phe
 70                  75                  80                  85

GGT TAT CAG ATG CAC TTT ATT TGT AAT GAG GGT TAT TAC TTA ATT GGT      498
Gly Tyr Gln Met His Phe Ile Cys Asn Glu Gly Tyr Tyr Leu Ile Gly
                 90                  95                 100

GAA GAA ATT CTA TAT TGT GAA CTT AAA GGA TCA GTA GCA ATT TGG AGC      546
Glu Glu Ile Leu Tyr Cys Glu Leu Lys Gly Ser Val Ala Ile Trp Ser
            105                 110                 115

GGT AAG CCC CCA ATA TGT GAA AAG GTT TTG TGT ACA CCA CCT CCA AAA      594
Gly Lys Pro Pro Ile Cys Glu Lys Val Leu Cys Thr Pro Pro Pro Lys
        120                 125                 130

ATA AAA AAT GGA AAA CAC ACC TTT AGT GAA GTA GAA GTA TTT GAG TAT      642
Ile Lys Asn Gly Lys His Thr Phe Ser Glu Val Glu Val Phe Glu Tyr
    135                 140                 145

CTT GAT GCA GTA ACT TAT AGT TGT GAT CCT GCA CCT GGA CCA GAT CCA      690
```

-continued

Leu Asp Ala Val Thr Tyr Ser Cys Asp Pro Ala Pro Gly Pro Asp Pro
150 155 160 165

TTT TCA CTT ATT GGA GAG AGC ACG ATT TAT TGT GGT GAC AAT TCA GTG 738
Phe Ser Leu Ile Gly Glu Ser Thr Ile Tyr Cys Gly Asp Asn Ser Val
170 175 180

TGG AGT CGT GCT GCT CCA GAG TGT AAA GTG GTC AAA TGT CGA TTT CCA 786
Trp Ser Arg Ala Ala Pro Glu Cys Lys Val Val Lys Cys Arg Phe Pro
185 190 195

GTA GTC GAA AAT GGA AAA CAG ATA TCA GGA TTT GGA AAA AAA TTT TAC 834
Val Val Glu Asn Gly Lys Gln Ile Ser Gly Phe Gly Lys Lys Phe Tyr
200 205 210

TAC AAA GCA ACA GTT ATG TTT GAA TGC GAT AAG GGT TTT TAC CTC GAT 882
Tyr Lys Ala Thr Val Met Phe Glu Cys Asp Lys Gly Phe Tyr Leu Asp
215 220 225

GGC AGC GAC ACA ATT GTC TGT GAC AGT AAC AGT ACT TGG GAT CCC CCA 930
Gly Ser Asp Thr Ile Val Cys Asp Ser Asn Ser Thr Trp Asp Pro Pro
230 235 240 245

GTT CCA AAG TGT CTT AAA GGT ACA AAG GTT ATC TTT TTT CTG TCT TGG 978
Val Pro Lys Cys Leu Lys Gly Thr Lys Val Ile Phe Phe Leu Ser Trp
250 255 260

TTT GTT ATT GTT GTT GCT GTT CAT TTT AGA CTT TAT TTC TTT GAT ATT 1026
Phe Val Ile Val Val Ala Val His Phe Arg Leu Tyr Phe Phe Asp Ile
265 270 275

AAC TAT CAG TCA TAC AAA ATA ACT GAA AAG AAA CAA TTT TAGTATTTAA 1075
Asn Tyr Gln Ser Tyr Lys Ile Thr Glu Lys Lys Gln Phe
280 285 290

CTCTGTCTTG TATTCATTTC TATGCCAGAT GAATGACACG AAATTCACAT AAAATTCTGC 1135

TGTTGTGATT TTTTGTGCTT TTCCAGGGTT CTTAGCACGT TATGTACATT GCATGGGTAT 1195

ATGCTTTTAA TATTTTTATG TATAAAAAGT GAATTACAAC AACTTTTTGG AATTGAAACA 1255

TGGGCATTTT TATCTAAGTA AGTCAACAAT GGCATAATTC ATATACCCG 1304

( 2 ) INFORMATION FOR SEQ ID NO:46:

( i ) SEQUENCE CHARACTERISTICS:
( A ) LENGTH: 324 amino acids
( B ) TYPE: amino acid
( D ) TOPOLOGY: linear ( i i ) MOLECULE TYPE: protein ( x i ) SEQUENCE DESCRIPTION: SEQ ID NO:46:

Met Glu Pro Pro Gly Arg Arg Glu Cys Pro Phe Pro Ser Trp Arg Phe
-34 -30 -25 -20

Pro Gly Leu Leu Leu Ala Ala Met Val Leu Leu Leu Tyr Ser Phe Ser
-15 -10 -5

Asp Ala Cys Glu Glu Pro Pro Thr Phe Glu Ala Met Glu Leu Ile Gly
1 5 10

Lys Pro Lys Pro Tyr Tyr Glu Ile Gly Glu Arg Val Asp Tyr Lys Cys
15 20 25 30

Lys Lys Gly Tyr Phe Tyr Ile Pro Pro Leu Ala Thr His Thr Ile Cys
35 40 45

Asp Arg Asn His Thr Trp Leu Pro Val Ser Asp Asp Ala Cys Tyr Arg
50 55 60

Glu Thr Cys Pro Tyr Ile Arg Asp Pro Leu Asn Gly Gln Ala Val Pro
65 70 75

Ala Asn Gly Thr Tyr Glu Phe Gly Tyr Gln Met His Phe Ile Cys Asn
80 85 90

Glu Gly Tyr Tyr Leu Ile Gly Glu Glu Ile Leu Tyr Cys Glu Leu Lys

-continued

| | | | | | | | | | | | | | | | |
|---|---|---|---|---|---|---|---|---|---|---|---|---|---|---|---|
| 95 | | | | | 100 | | | | | 105 | | | | | 110 |
| Gly | Ser | Val | Ala | Ile | Trp | Ser | Gly | Lys | Pro | Pro | Ile | Cys | Glu | Lys | Val |
| | | | | 115 | | | | | 120 | | | | | 125 | |
| Leu | Cys | Thr | Pro | Pro | Pro | Lys | Ile | Lys | Asn | Gly | Lys | His | Thr | Phe | Ser |
| | | | 130 | | | | | 135 | | | | | 140 | | |
| Glu | Val | Glu | Val | Phe | Glu | Tyr | Leu | Asp | Ala | Val | Thr | Tyr | Ser | Cys | Asp |
| | | 145 | | | | | 150 | | | | | 155 | | | |
| Pro | Ala | Pro | Gly | Pro | Asp | Pro | Phe | Ser | Leu | Ile | Gly | Glu | Ser | Thr | Ile |
| | 160 | | | | | 165 | | | | | 170 | | | | |
| Tyr | Cys | Gly | Asp | Asn | Ser | Val | Trp | Ser | Arg | Ala | Ala | Pro | Glu | Cys | Lys |
| 175 | | | | | 180 | | | | | 185 | | | | | 190 |
| Val | Val | Lys | Cys | Arg | Phe | Pro | Val | Val | Glu | Asn | Gly | Lys | Gln | Ile | Ser |
| | | | | 195 | | | | | 200 | | | | | 205 | |
| Gly | Phe | Gly | Lys | Lys | Phe | Tyr | Tyr | Lys | Ala | Thr | Val | Met | Phe | Glu | Cys |
| | | | 210 | | | | | 215 | | | | | 220 | | |
| Asp | Lys | Gly | Phe | Tyr | Leu | Asp | Gly | Ser | Asp | Thr | Ile | Val | Cys | Asp | Ser |
| | | 225 | | | | | 230 | | | | | 235 | | | |
| Asn | Ser | Thr | Trp | Asp | Pro | Pro | Val | Pro | Lys | Cys | Leu | Lys | Gly | Thr | Lys |
| | 240 | | | | | 245 | | | | | 250 | | | | |
| Val | Ile | Phe | Phe | Leu | Ser | Trp | Phe | Val | Ile | Val | Val | Ala | Val | His | Phe |
| 255 | | | | | 260 | | | | | 265 | | | | | 270 |
| Arg | Leu | Tyr | Phe | Phe | Asp | Ile | Asn | Tyr | Gln | Ser | Tyr | Lys | Ile | Thr | Glu |
| | | | | 275 | | | | | 280 | | | | | 285 | |
| Lys | Lys | Gln | Phe | | | | | | | | | | | | |
| | | | 290 | | | | | | | | | | | | |